US011654042B2

(12) United States Patent
Hughett, Sr.

(10) Patent No.: US 11,654,042 B2
(45) Date of Patent: May 23, 2023

(54) URINE OUTPUT COLLECTION AND MONITORING SYSTEM

(71) Applicant: MEDIVANCE INCORPORATED, Louisville, CO (US)

(72) Inventor: James David Hughett, Sr., Monroe, GA (US)

(73) Assignee: Medivance Incorporated, Louisville, CO (US)

( * ) Notice: Subject to any disclaimer, the term of this patent is extended or adjusted under 35 U.S.C. 154(b) by 661 days.

(21) Appl. No.: 15/748,107

(22) PCT Filed: Jul. 29, 2016

(86) PCT No.: PCT/US2016/044835
§ 371 (c)(1),
(2) Date: Jan. 26, 2018

(87) PCT Pub. No.: WO2017/023794
PCT Pub. Date: Feb. 9, 2017

(65) Prior Publication Data
US 2018/0214297 A1    Aug. 2, 2018

Related U.S. Application Data

(60) Provisional application No. 62/199,817, filed on Jul. 31, 2015.

(51) Int. Cl.
*A61F 5/44* (2006.01)
*A61B 5/00* (2006.01)
(Continued)

(52) U.S. Cl.
CPC ................ *A61F 5/44* (2013.01); *A61B 5/00* (2013.01); *A61B 5/208* (2013.01); *A61B 5/743* (2013.01);
(Continued)

(58) Field of Classification Search
None
See application file for complete search history.

(56) References Cited

U.S. PATENT DOCUMENTS 3,919,455 A    11/1975   Sigdell et al.
4,276,889 A     7/1981   Kuntz et al.
(Continued)

FOREIGN PATENT DOCUMENTS

CA      2882654 A1    10/2007
CN    112426156 A     3/2021
(Continued)

OTHER PUBLICATIONS

Biometrix, Urimetrix, 4 pages, www.biometrixmedical.com/Products/56/Urimetrix%E2%84%A2 Oct. 29, 2014.
(Continued)

*Primary Examiner* — Jacqueline Cheng
*Assistant Examiner* — Jairo H Portillo
(74) *Attorney, Agent, or Firm* — Rutan & Tucker LLP

(57) ABSTRACT

Improved urine output collection apparatus and monitoring device features are provided. The disposable urine collection apparatus includes a collection reservoir and a diverter for controlling the flow of urine to a first passageway of the diverter in a first position and to a second passageway of the diverter in a second position, wherein the first passageway is fluidly interconnected to the collection reservoir. The disposable urine collection apparatus may include a cartridge having an internal chamber and inlet and outlet members interconnected to the cartridge, wherein the inlet member is selectively, fluidly interconnectable to the second passageway of the diverter, and wherein the outlet member is selectively, fluidly interconnectable to the collection reservoir. The monitoring device is interconnectable with the cartridge and operable to monitor a volume and/or level of (Continued)

urine collected within the cartridge. The cartridge may include a front portion and a reduced-width projecting portion extending rearwardly from the front portion. The projecting portion of the cartridge may be received within a recessed portion of the monitoring device. The monitoring device may include at least light source (e.g. a laser diode) for emitting a fan beam light signal into the projecting portion and a light detector array (e.g. a charge coupled device) for detection of the fan beam light signal and output of signals employable to determine a volume and/or level of collected urine.

19 Claims, 27 Drawing Sheets

(51) Int. Cl.
*A61B 5/20* (2006.01)
*A61B 10/00* (2006.01)
*A61M 25/00* (2006.01)

(52) U.S. Cl.
CPC .......... *A61B 5/7425* (2013.01); *A61B 5/7435* (2013.01); *A61B 5/7445* (2013.01); *A61B 10/007* (2013.01); *A61F 5/4404* (2013.01); *A61F 5/4405* (2013.01); *A61M 25/0017* (2013.01); *A61M 25/0097* (2013.01); *A61B 2562/0233* (2013.01); *A61F 2005/4402* (2013.01); *A61M 2202/0496* (2013.01); *A61M 2205/123* (2013.01); *A61M 2205/3306* (2013.01); *A61M 2205/3334* (2013.01); *A61M 2205/3389* (2013.01); *A61M 2205/505* (2013.01)

(56) References Cited

U.S. PATENT DOCUMENTS

| | | | |
|---|---|---|---|
| 4,296,749 A * | 10/1981 | Pontifex | A61F 5/445 |
| | | | 604/344 |
| 4,305,405 A | 12/1981 | Meisch | |
| 4,312,352 A | 1/1982 | Meisch et al. | |
| 4,343,316 A | 8/1982 | Jespersen | |
| 4,443,219 A | 4/1984 | Meisch et al. | |
| 4,448,207 A | 5/1984 | Parrish | |
| 4,532,936 A | 8/1985 | LeVeen et al. | |
| 4,658,834 A | 4/1987 | Blankenship et al. | |
| 4,723,950 A | 2/1988 | Lee | |
| 4,850,375 A | 7/1989 | Rosenberg | |
| 4,889,532 A * | 12/1989 | Metz | A61F 5/455 |
| | | | 604/330 |
| 5,002,541 A * | 3/1991 | Conkling | A61F 5/44 |
| | | | 604/319 |
| 5,409,014 A * | 4/1995 | Napoli | A61B 5/20 |
| | | | 600/575 |
| 5,725,515 A | 3/1998 | Propp | |
| 5,733,319 A | 3/1998 | Neilson et al. | |
| 5,747,824 A | 5/1998 | Jung et al. | |
| 5,769,087 A * | 6/1998 | Westphal | A61B 5/14507 |
| | | | 600/573 |
| 5,807,278 A | 9/1998 | McRae | |
| 5,823,972 A | 10/1998 | McRae | |
| 5,891,051 A | 4/1999 | Han et al. | |
| 5,911,786 A | 6/1999 | Nielsen et al. | |
| 6,129,684 A | 10/2000 | Sippel et al. | |
| 6,132,407 A | 10/2000 | Genese et al. | |
| 6,261,254 B1 | 7/2001 | Baron et al. | |
| 6,592,612 B1 | 7/2003 | Samson et al. | |
| 6,709,420 B1 | 3/2004 | Lincoln et al. | |
| 6,716,200 B2 | 4/2004 | Bracken et al. | |
| 7,011,634 B2 | 3/2006 | Paasch et al. | |
| 7,871,385 B2 | 1/2011 | Levinson | |
| 7,931,630 B2 | 4/2011 | Nishtala et al. | |
| 7,998,126 B1 * | 8/2011 | Fernandez | A61F 5/4556 |
| | | | 604/329 |
| 8,328,733 B2 | 12/2012 | Forte et al. | |
| 8,328,734 B2 | 12/2012 | Salvadori et al. | |
| 8,337,476 B2 | 12/2012 | Greenwald et al. | |
| 8,403,884 B2 | 3/2013 | Nishtala | |
| 8,471,231 B2 | 6/2013 | Paz | |
| 8,663,128 B2 | 3/2014 | Paz et al. | |
| 8,773,259 B2 | 7/2014 | Judy et al. | |
| 8,790,277 B2 | 7/2014 | Elliott et al. | |
| 8,790,320 B2 | 7/2014 | Christensen | |
| 8,790,577 B2 | 7/2014 | Mizumoto et al. | |
| 8,813,551 B2 | 8/2014 | Boiarski | |
| 8,827,924 B2 | 9/2014 | Paz et al. | |
| 8,832,558 B2 | 9/2014 | Cardarelli et al. | |
| 9,050,046 B2 | 6/2015 | Elliott et al. | |
| 9,074,920 B2 | 7/2015 | Mendels et al. | |
| 9,216,242 B2 | 12/2015 | Nishtala et al. | |
| 9,895,095 B2 | 2/2018 | Chen | |
| 10,182,747 B2 | 1/2019 | Charlez et al. | |
| 10,245,008 B2 | 4/2019 | Paige | |
| 10,362,981 B2 | 7/2019 | Paz et al. | |
| 10,448,875 B2 | 10/2019 | Holt et al. | |
| 2001/0056226 A1 | 12/2001 | Zodnik et al. | |
| 2002/0161314 A1 | 10/2002 | Sarajarvi | |
| 2002/0193760 A1 | 12/2002 | Thompson | |
| 2003/0163183 A1 | 8/2003 | Carson | |
| 2004/0267086 A1 | 12/2004 | Anstadt et al. | |
| 2005/0020958 A1 | 1/2005 | Paolini et al. | |
| 2005/0065583 A1 | 3/2005 | Voorhees et al. | |
| 2005/0247121 A1 * | 11/2005 | Pelster | G01F 11/125 |
| | | | 73/223 |
| 2006/0100743 A1 | 5/2006 | Townsend et al. | |
| 2007/0010797 A1 | 1/2007 | Nishtala et al. | |
| 2007/0145137 A1 | 6/2007 | Mrowiec | |
| 2007/0252714 A1 * | 11/2007 | Rondoni | A61B 5/0002 |
| | | | 340/573.5 |
| 2009/0099629 A1 | 4/2009 | Carson et al. | |
| 2009/0157430 A1 | 6/2009 | Rule et al. | |
| 2009/0287170 A1 | 11/2009 | Otto | |
| 2010/0094204 A1 | 4/2010 | Nishtala | |
| 2010/0137743 A1 | 6/2010 | Nishtala et al. | |
| 2011/0178425 A1 | 7/2011 | Nishtala et al. | |
| 2011/0238042 A1 | 9/2011 | Davis et al. | |
| 2011/0251572 A1 | 10/2011 | Nishtala et al. | |
| 2012/0029408 A1 | 2/2012 | Beaudin | |
| 2012/0078137 A1 * | 3/2012 | Mendels | G01F 23/2921 |
| | | | 600/584 |
| 2012/0078235 A1 | 3/2012 | Martin et al. | |
| 2012/0095304 A1 | 4/2012 | Biondi | |
| 2012/0109008 A1 | 5/2012 | Charlez et al. | |
| 2012/0127103 A1 | 5/2012 | Qualey et al. | |
| 2012/0226196 A1 | 9/2012 | DiMino et al. | |
| 2012/0302917 A1 | 11/2012 | Fitzgerald et al. | |
| 2012/0323502 A1 | 12/2012 | Tanoura et al. | |
| 2013/0109927 A1 | 5/2013 | Menzel | |
| 2013/0109928 A1 | 5/2013 | Menzel | |
| 2013/0131610 A1 * | 5/2013 | Dewaele | A61B 5/0215 |
| | | | 604/264 |
| 2013/0218106 A1 | 8/2013 | Coston et al. | |
| 2013/0267871 A1 | 10/2013 | Delaney et al. | |
| 2014/0039348 A1 | 2/2014 | Bullington et al. | |
| 2014/0155781 A1 | 6/2014 | Bullington et al. | |
| 2014/0155782 A1 | 6/2014 | Bullington et al. | |
| 2014/0159921 A1 | 6/2014 | Qualey et al. | |
| 2014/0207085 A1 | 7/2014 | Brandt et al. | |
| 2015/0343173 A1 | 12/2015 | Tobescu et al. | |
| 2015/0359522 A1 * | 12/2015 | Recht | G01N 21/255 |
| | | | 600/573 |
| 2015/0362351 A1 * | 12/2015 | Joshi | A61B 10/007 |
| | | | 700/282 |
| 2017/0196478 A1 | 7/2017 | Hunter | |
| 2018/0344234 A1 | 12/2018 | McKinney et al. | |
| 2019/0046102 A1 | 2/2019 | Kushnir et al. | |
| 2019/0069830 A1 | 3/2019 | Holt et al. | |
| 2019/0223844 A1 | 7/2019 | Aboagye et al. | |
| 2019/0247236 A1 | 8/2019 | Sides et al. | |
| 2019/0321588 A1 | 10/2019 | Burnett et al. | |

(56) References Cited

U.S. PATENT DOCUMENTS

| | | |
|---|---|---|
| 2019/0328945 A1 | 10/2019 | Analytis et al. |
| 2019/0365308 A1 | 12/2019 | Laing et al. |
| 2020/0085378 A1 | 3/2020 | Burnett et al. |
| 2020/0289749 A1 | 9/2020 | Odashima et al. |
| 2021/0077007 A1 | 3/2021 | Jouret et al. |
| 2022/0018692 A1 | 1/2022 | Tourchak et al. |
| 2022/0192564 A1 | 6/2022 | Kriscovich et al. |
| 2022/0192565 A1 | 6/2022 | Cheng et al. |
| 2022/0192566 A1 | 6/2022 | Cheng et al. |
| 2022/0193375 A1 | 6/2022 | Rehm et al. |
| 2022/0296140 A1 | 9/2022 | Nguyen et al. |
| 2022/0386917 A1 | 12/2022 | Mann et al. |
| 2023/0022547 A1 | 1/2023 | Cho et al. |
| 2023/0025333 A1 | 1/2023 | Patel et al. |
| 2023/0028966 A1 | 1/2023 | Franano |
| 2023/0035669 A1 | 2/2023 | Raja et al. |
| 2023/0040915 A1 | 2/2023 | Compton et al. |

FOREIGN PATENT DOCUMENTS

| | | |
|---|---|---|
| GB | 2576743 A | 3/2020 |
| WO | 2014108690 A1 | 7/2014 |
| WO | 2014/135856 A1 | 9/2014 |
| WO | 2014/151068 A2 | 9/2014 |
| WO | 2014135856 A1 | 9/2014 |

OTHER PUBLICATIONS

Observe Medical, sippi, 3 pages, www.observemedical.com/products.html Oct. 29, 2014.

Bard Medical, Criticore Monitor, 11 pages, www.bardmedical.com/products/patient-monitoring-systems/criticore®-monitor/ Jan. 30, 2015.

Bard Medical, Urine Meters, 3 pages, www.bardmedical.com/products/urological-drainage/urine-collection/urine-meters/ Jan. 30, 2015.

Bard Medical, Criticore Disposables—Non I.C., 3 pages, www.bardmedical.com/products/patient-monitoring-systems/criticore®-system/criticore®-disposables-non-ic/ Jan. 30, 2015.

Bard Medical, Criticore Infection Control Disposables, 3 pages, www.bardmedical.com/patient-monitoring-systems/criticore®-system/criticore®-infection-control-disposables/ Jan. 30, 2015.

U.S. Appl. No. 17/373,535, filed Jul. 12, 2021 Non-Final Office Action dated Nov. 9, 2022.

U.S. Appl. No. 17/054,493, filed Nov. 10, 2020 Final Office Action dated May 31, 2022.

U.S. Appl. No. 17/054,493, filed Nov. 10, 2020 Non-Final Office Action dated Jan. 27, 2023.

U.S. Appl. No. 17/3026,821, filed May 3, 2021 Non-Final Office Action dated Jan. 10, 2023.

\* cited by examiner

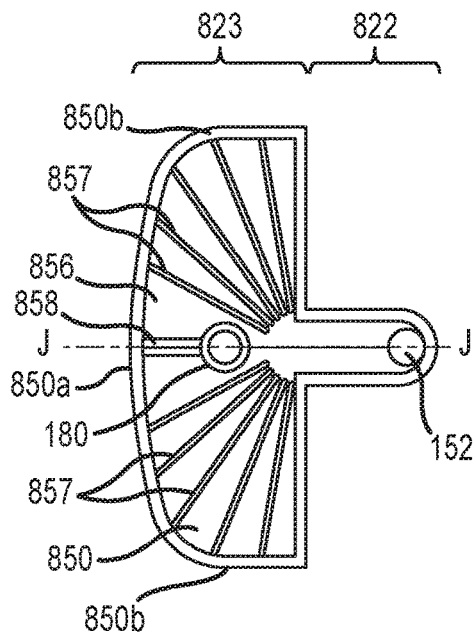
FIG.26
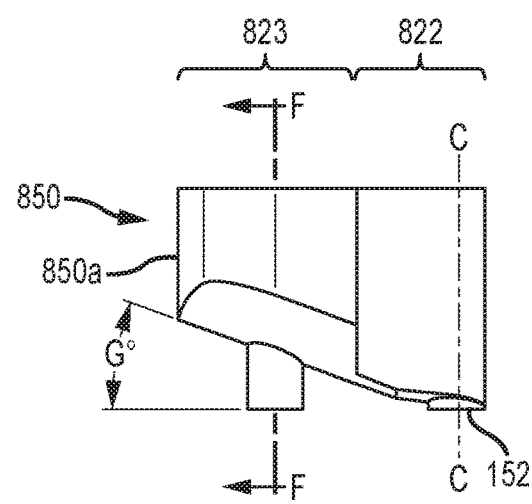
FIG.27
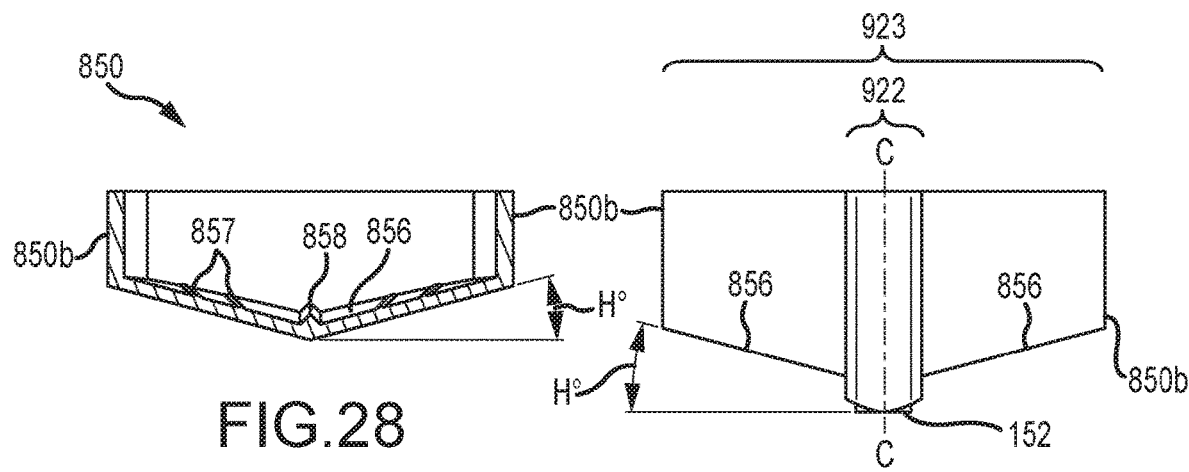
FIG.28
FIG.29

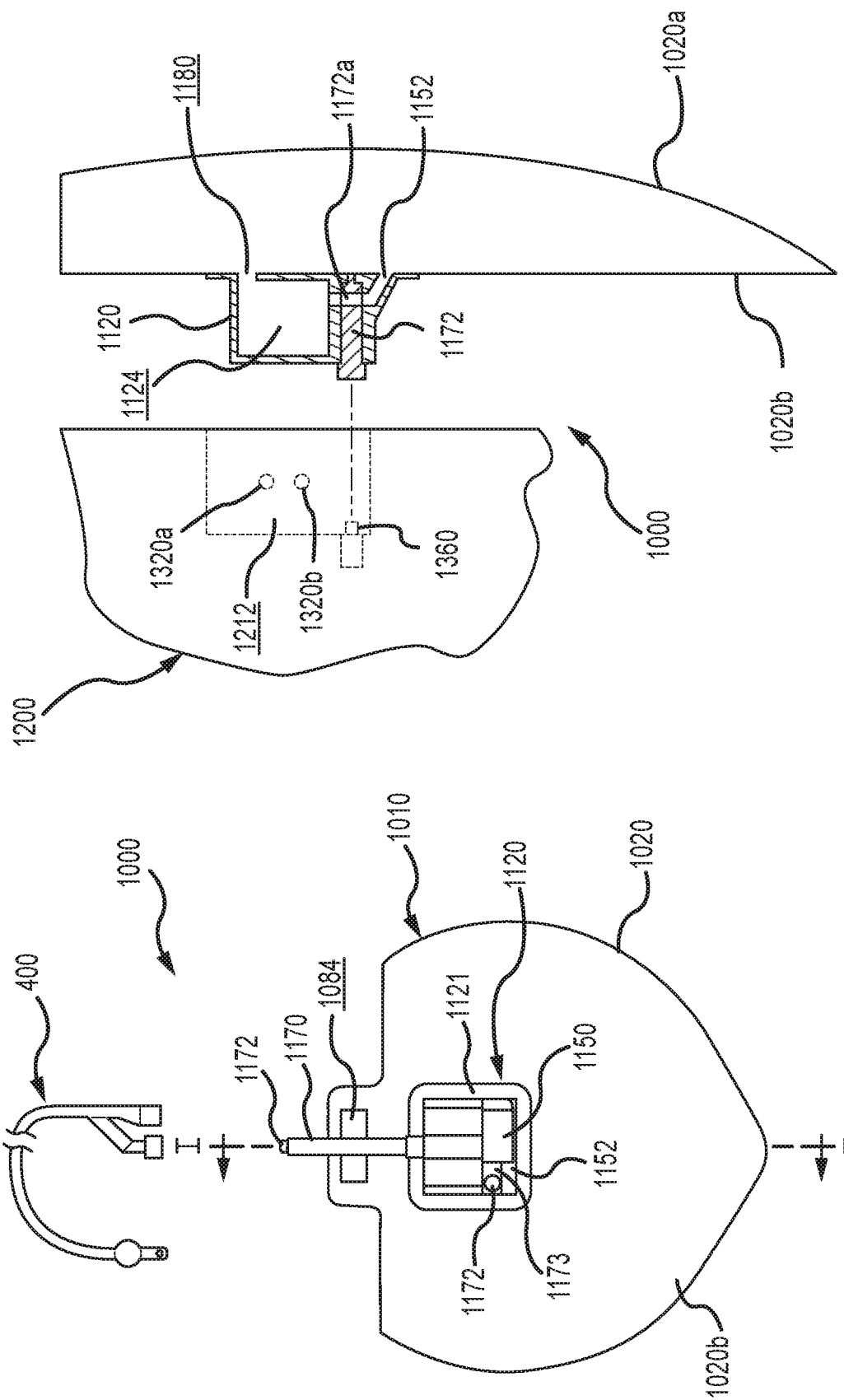

URINE OUTPUT COLLECTION AND MONITORING SYSTEM

RELATED APPLICATIONS

This application is a U.S. national stage application of International Application No. PCT/US2016/044835, filed Jul. 29, 2016, which claims priority to U.S. Provisional Patent Application No. 62/199,817, filed Jul. 31, 2015, and titled "URINE OUTPUT COLLECTION AND MONITORING SYSTEM", each of which is hereby incorporated by reference in its entirety into this application.

FIELD OF THE INVENTION

The present invention relates to apparatus and systems for handling patient urine output, and more particularly, to improved urine output collection apparatus and monitoring system features.

BACKGROUND OF THE INVENTION

Patient urine output is increasingly recognized as a vital indicator of patient health. In that regard, fluid imbalances in at-risk patients can yield significant adverse complications, both in relation to insufficient bodily fluid and excess bodily fluid. Therefore, monitoring patient urine output is often crucial in order to identify risk conditions requiring remedial action.

In many instances, diuretics are employed at acute care facilities as a mechanism to manage fluid imbalance. Diuretics promote the production of urine by increasing the excretion of water. Conversely, anti-diuretics may be employed to reduce the excretion of water. In each case, proper dosing may be dependent upon a determined level of patient urine output, including for example a determined rate of urine output after administration of a prior dose. As such, the accuracy of urine output determinations may directly impact the efficacy of diuretic and anti-diuretic dosing therapies.

Obtaining accurate urine output data can present a number of challenges. Currently, in many patient care facilities, an in-dwelling urinary catheter may be utilized with certain patients at the outset of acute care (e.g. at the time of hospital admission) in order to allow urine to drain freely from a patient's bladder. Typically, such in-dwelling urinary catheters may be fluidly interconnected to a urine collection reservoir, e.g. via a length flexible tubing. While such reservoirs typically include visible volumetric markings, or gradations, they fail to provide urine output flow rate data. Further, manual determinations and ongoing maintenance of urine output flow rate data is problematic.

As such, urine output monitoring systems are often employed, wherein such systems typically include a monitor and associated disposable assemblies. Such monitors utilize various automated or semi-automated approaches to measure urine output through a component of the disposable assembly, typically upstream from a urine collection reservoir of the disposable assembly. In various implementations, it is necessary to interconnect the given disposable assembly to an in-dwelling urinary catheter at the time of catheterization. In turn, in such implementations, if the disposable assembly for monitoring is not interconnected at the beginning of acute care, patient recatheterization may be required at a later time when monitoring is desired. Recatheterization is undesirable from the standpoint of both added infection risk, patient discomfort and cost.

In addition to the foregoing, known urine output monitoring systems often fail to adequately accommodate situations in which a disposable assembly needs to be temporarily disassociated and then reassociated with a monitor while maintaining patient catheterization. By way of example, such situations may arise when a given patient requires movement for imaging or other similar procedures.

Further, in many urine output monitoring arrangements, the disposable assemblies and/or monitors may be difficult for medical personnel to utilize and may otherwise fail to provide sufficiently accurate urine output data.

SUMMARY OF THE INVENTION

In view of the foregoing, an objective of the present invention is to provide urine output collection apparatus and/or monitoring system features that provide for increased flexibility in use.

Another objective is to provide urine output collection apparatus and/or monitoring system features that provide for increased accuracy in urine output data.

Yet another objective is to provide urine output collection apparatus and monitoring system features that provide for enhanced ease-of-use by medical personnel.

Such objectives and additional advantages are addressed in various embodiments of the present disclosure. For example, embodiments are disclosed that are directed to improved disposable urine collection apparatus and/or an improved monitoring device for interfacing with disposable urine collection apparatus to monitor urine output. In some embodiments, a disposable urine collection apparatus may include a first urine collection device that may be utilized in a stand-alone manner, and a second urine collection device that may be selectively, fluidly interconnectable to the first urine collection device for interconnected use. In some implementations, the disposable urine collection apparatus may interface with a monitoring device that monitors a volume of urine output and/or successive volumes of urine output collected in the disposable urine collection apparatus. For example, the disposable urine collection apparatus may be selectively, physically interconnected to and disconnected from the monitoring device.

In one embodiment, an improved disposable urine collection apparatus includes a collection reservoir having an internal volume, and a diverter having an inlet port and a first flow control member for fluidly interconnecting the inlet port to a first passageway of the diverter in a first position, and for fluidly interconnecting the inlet port to a second passageway of the diverter in a second position. The disposable urine collection device may further include a reservoir interface fixedly and fluidly interconnected to the collection reservoir, and fluidly interconnectable to the first passageway of the diverter, wherein when the first flow control member is in the first position the inlet port of the diverter is fluidly interconnected to the collection reservoir via the first passageway of the diverter and the reservoir interface. In some implementations, the reservoir interface may include a second flow control member for closing the passageway to the reservoir interface in a first position. By way of example, the collection reservoir may comprise a flexible bag, while the diverter and reservoir interface may be of rigid or semi-rigid construction.

In some implementations, the disposable urine collection apparatus may include a cartridge having an internal chamber, a tubular inlet member having an inlet port at a first end and a second end fluidly interconnected to the internal chamber of the cartridge, and at least one tubular outlet member having a first end fluidly interconnected to the internal chamber of the cartridge and outlet port at a second end. The inlet port of the inlet member may be selectively interconnectable to an outlet port of the second passageway of the diverter. Further, the outlet port of the outlet member may be selectively interconnectable to an inlet port of a passageway of the reservoir interface. By way of example, the cartridge and inlet and outlet members may be of rigid or semi-rigid construction.

In some arrangements, the collection reservoir, diverter and reservoir interface may be interconnected or interconnectable to define a unit that may be referred to as a first urine collection device. Additionally, the cartridge, tubular inlet member and tubular outlet member(s) may be interconnected or interconnectable to define a unit that may be referred to as a second urine collection device.

The diverter may be provided so that the inlet port and the second passageway of the diverter are blocked from being fluidly interconnected by the first control member when the first control member is in the first position. Further, the diverter may be provided so that the inlet port and the first passageway of the diverter are blocked from being fluidly interconnected by the first control member when the first control member is in the second position.

In some arrangements, the first control member of the diverter may comprise a first channel that is configured to fluidly interconnect the inlet port and the first passageway of the diverter when the first control member is in the first position. The first control member may also include a second channel that is configured to fluidly interconnect the inlet port and the second passageway of the diverter when the first control member is in the second position.

In some implementations, the diverter and the inlet port of the inlet member may be configured so that, upon interconnection of the inlet port of the inlet member and outlet port of the second passageway of the diverter, the first control member is mechanically moved from the first position to the second position. Similarly, in some arrangements, the reservoir interface and outlet port of the outlet member may be configured so that, upon interconnection of the outlet port of the outlet member and inlet port of the passageway of the reservoir interface, the second control member is mechanically moved from the first position to a second position in which the passageway is fluidly interconnected to the collection reservoir.

In some embodiments, the disposable urine collection apparatus may be provided so that the inlet port of the inlet member and the outlet port of the second passageway of the diverter are not disconnectable after interconnection. Similarly, the disposable urine collection apparatus may be provided so that the outlet port of the outlet member and the inlet port of the passageway of the reservoir interface are not disconnectable after interconnection. As may be appreciated, such one way interconnection features advantageously restrict undesired disconnection of the referenced components after their initial interconnection.

In one approach, the disposable urine collection apparatus may include a first interconnection member provided at the inlet port of the inlet member and configured for locking engagement with the outlet port of the second passageway of the diverter. Further, a second interconnection may be provided at the outlet port of the outlet member and configured for locking engagement with the inlet port of the passageway of the reservoir interface.

In some arrangements, the outlet port of the second passageway of the diverter and the inlet port of the inlet member may have first complementary configurations for mating engagement. Further, the outlet port of the outlet member and the inlet port of the passageway of the reservoir interface may have second complementary configurations for mating engagement. The first and second complementary configurations may be different so as to physically preclude mating engagement of the outlet port of the second passageway of the diverter with the outlet port of the outlet member, and to physically preclude mating engagement of the inlet port of the inlet member with the inlet port of the passageway of the reservoir interface. As may be appreciated, the provision of differing mating engagement configurations precludes undesired interconnections of the referenced components.

In contemplated embodiments, a urinary catheter (e.g. an in-dwelling, or Foley, catheter) may be interconnected at a proximal end to the inlet port of the diverter so as to define a first closed fluid pathway from the distal end of the urinary catheter through the diverter and the reservoir interface, and in to the internal volume of the collection reservoir when the flow control member is in the first position. When the first flow control member is in the second position, a second closed fluid pathway may be defined from the distal end of the urinary catheter, through the diverter, the cartridge and the reservoir interface, and in to the internal volume of the collection reservoir.

In some implementations, a disposable urine collection apparatus may be provided that includes a cartridge member, wherein the cartridge includes a front portion having a first width and a projecting portion that extends rearwardly from the front portion and has a second width that is less than the first width (e.g. the front portion and projecting portion may define a T-shaped cartridge configuration). As will be further described, the projecting portion may be interconnected to and inserted into a recessed portion of a monitoring device adapted to determine a volume of urine collected in the cartridge by monitoring a surface position of the accumulated urine in the projecting portion. The disposable urine collection apparatus may further comprise a discharge port located within the projecting portion of the cartridge, a valve member positionable to close and open the discharge port, and a biasing member to mechanically bias the valve member to a closed position at the discharge port. As will be further described, the monitoring device referenced above may be adapted to open the valve member when interconnected to the cartridge (e.g. to provide for gravity discharge of urine from the cartridge to the collection reservoir).

In some embodiments, the projecting portion of the cartridge may include a first sidewall, and a second sidewall that faces the first sidewall with a portion of the internal volume of the cartridge located therebetween. At least opposing sidewall portions of the first and second sidewalls may be light transmissive. In that regard, and as will further be described, in some embodiments the monitoring device referenced above may provide for the emission and detection of light signals through the projecting portion of the cartridge to determine a volume of urine collected in the cartridge by monitoring a surface position of the accumulated urine in the projecting portion.

In some arrangements, the opposing sidewall portions of the first sidewall and the second sidewall of the projecting portion may be substantially parallel so as to define a substantially constant width therebetween. In turn, the cartridge and monitoring device may be provided so that the first and second sidewalls of the projecting portion are disposed substantially vertical when the cartridge is interconnected to the monitoring device.

In some implementations, internal surfaces of at least opposing sidewall portions of the first and second sidewalls may be hydrophobic to reduce condensation accumulation thereupon, thereby facilitating urine accumulation detection. In one approach, such surfaces may have a hydrophobic coating applied thereto.

In some embodiments, the cartridge may include one or a plurality of nucleation members that project downward from an upper surface of the internal volume of the cartridge and upon which condensation droplets may form to reduce condensation accumulation on inner sidewall surfaces of the cartridge (e.g. inner surfaces of the first and second sidewalls of the projecting portion noted above), thereby facilitating urine accumulation detection. For example, a plurality of nucleation members may project downward from a top surface of the internal volume within the front portion of the cartridge. In some arrangements, the nucleation member(s) may be tubular to enhance droplet formation and/or tapered from top to bottom (e.g. to define a stalactite configuration) to enhance droplet release for accumulation within the cartridge.

In some implementations, the disposable urine collection apparatus may include an overflow port defined by an upstanding tubular member located within the internal volume of the cartridge. In that regard, the upstanding tubular member may be provided to extend upwards from a bottom surface of the internal volume within the front portion of the cartridge.

In some embodiments, at least a portion of a bottom surface of the internal volume of the cartridge may be of a planar configuration and may be oriented to extend rearward and downward from a front face of the front portion of the cartridge to the projecting portion of the cartridge. At least a portion of the bottom surface may extend rearward and downward from the front face of the front portion of the cartridge to the projecting portion, and optionally within the projecting portion, at an angle of at least about 11°, and in some implementations at least 15°, relative to a reference plane that extends perpendicular to a longitudinal axis extending through the discharge port.

In some implementations, at least a portion of a bottom surface of the internal volume of the cartridge may extend rearward and downward from a front face of the front portion of the cartridge to the projecting portion of the cartridge with a downward step provided in the bottom surface at an interface between the front portion and projecting portion of the cartridge, thereby enhancing urine flow along the bottom surface in to the projecting portion. Further, the downward step defines a well in the projecting portion that may function to retain small volumes of urine in the projecting portion if the cartridge is tilted. In the front portion, and optionally the projecting portion, at least a portion of the bottom surface may extend rearward and downward at an angle of at least about 11°, and in some implementations at least 15°, relative to a reference plane that extends perpendicular to a longitudinal axis extending through the discharge port. At the downward step, the bottom surface may extend downward at an angle of at least 45°, and in some implementations at least 75°, or 90°, relative to such reference plane.

In some embodiments, the cartridge may include a tubular inlet member that extends through an upper surface (e.g. a top surface) of the internal volume of the cartridge in the front portion of the cartridge and that is configured to direct urine flow toward the projecting portion and away from an overflow port provided in the internal volume (e.g. away from a top end of an upstanding tubular member comprising the overflow port and located in the front portion). In one approach, the tubular inlet member may include an external portion that extends upward and away from the cartridge (e.g. at an acute angle) to an inlet port at a first end, and an adjoined internal portion that extends within the internal volume in the front portion to an outlet port at a second end. In some arrangements, the internal portion of the inlet member may extend along a top surface of the internal volume of the cartridge in the front portion with the outlet end located at or adjacent to an interface between the front portion and the projecting portion of the cartridge.

In some implementations, at least a portion of a bottom surface of the internal volume of the cartridge may extend rearward and downward from a front face of the front portion of the cartridge to the projecting portion of the cartridge and may include a plurality of grooves or upstanding landings that extend along the bottom surface in the front portion toward the projecting portion to facilitate urine flow along the bottom surface to the projecting portion. The grooves and/or landings may extend along the bottom surface toward the projecting portion in a converging manner, e.g. to define a spoke-like pattern centered upon a bottom surface interface region between the front portion and projecting portion. In the front portion, and optionally the projecting portion, at least a portion of the bottom surface may extend rearward and downward at an angle of at least about 11°, and in some implementations at least 15°, relative to a reference plane that extends perpendicular to a longitudinal axis extending through the discharge port.

In some embodiments, at least a portion of a bottom surface of the internal volume of the cartridge may extend rearward and downward from a front face of the front portion of the cartridge to the projecting portion of the cartridge with a raised surface portion extending between the front face and an overflow port located in the front portion, e.g. a base of an upstanding tubular member, so as to direct urine flow around the outlet port to the projecting portion. For example, the raised surface portion having an inverted V-shaped configuration and may extend along a center axis of the bottom surface of the cartridge that extends through the front portion and projecting portion, and along which the outlet port is located.

In some arrangements, at least a portion of a bottom surface of the internal volume of the cartridge in the front portion thereof may extend rearward and downward from a front face of the front portion to the projecting portion of the cartridge, wherein such bottom surface portion may also extend downward toward a center axis of the bottom surface that extends through the front portion and projection portion. For example, such bottom surface portion may have V-shaped configuration that slopes downward from the front face of the front portion to the projecting portion, wherein the bottom surface may optionally also extend rearward and downward in the projecting portion.

In some implementations, the disposable urine collection apparatus may include a piston member having a bottom end interconnected to a valve member within the internal volume of the cartridge, and a top end located outside of the internal volume of the cartridge. Further, a biasing member may comprise a spring that is disposed about at least a portion of the piston member located within the internal volume of the cartridge. In one approach, the spring member may be disposed about and along at least a portion of the position member within the projecting portion of the cartridge.

In some embodiments, a top end of the piston member may be displaceable upward against the bias provided by the biasing member and relative to the cartridge so as to displace the valve member to an open position relative to the discharge port. In some approaches, a top end member may be provided at the top end of the piston member, outside of the internal volume of the cartridge, wherein the top member is provided for upwardly displacing the interconnected piston member and valve member. As will be further described, such upward displacement may be achieved manually when the disposable urine collection apparatus is not interconnected to a monitoring device, and in an automated manner when the disposable urine collection apparatus is operatively interconnected to the monitoring device. In the later regard, the top end member may include an arm that extends laterally beyond a rear wall of the projecting portion of the cartridge for interfacing with the monitoring device.

In some embodiments, the top end member may be provided so that, upon upward displacement of the top member to at least a predetermined height relative to the cartridge, the top end member is selectively retainable at the predetermined height to maintain the valve in an open position at the discharge port. In one approach, upon upward displacement of the top end member to at least a predetermined height, and rotation of the top member to a rotated position, the top end member is retainable at the predetermined height by engagement with said cartridge (e.g. via spring-loaded engagement against a surface of the cartridge) so as to maintain the valve in the open position at the discharge port, free from manual retention of the top end member. In that regard, a body portion of the top end member may be slidably disposed in a recessed portion of the cartridge, wherein one of the body portion and the recessed portion comprises at least one projecting rib and the other one of the body portion and the recessed portion comprises at least one groove sized to receive the at least projecting rib. In turn, when the top end member is in the elevated, rotated position, the rib(s) is operable to retain the top end member at the predetermined height (e.g. via abutment between the top end member and a surface of the cartridge at the end of the rib(s)). In some implementations, the disposable urine collection apparatus and monitoring device may be configured so that, when the top end member is retained at the predetermined height, the disposable urine collection apparatus cannot be interconnected to the monitoring device, thereby requiring manual repositioning of the top end member from the rotated position to allow the spring-loaded valve to return to the closed position before interconnection to the monitoring device.

In some arrangements, the disposable urine collection apparatus may further include a tubular second outlet member fluidly interconnected at a first end thereof to the overflow port located in the cartridge. In turn, a second end of the second outlet member and the second end of the first outlet member may be interconnected at a tubular Y-member that further defines a common outlet port.

As noted above, a monitoring device may be provided to interface (e.g. interconnect) with a disposable urine collection apparatus to monitor urine output. In one embodiment, the monitoring device may include a recessed portion for receiving a projecting portion of the cartridge of a disposable urine collection apparatus, and first and second light sources disposed on a first side of the recessed portion, wherein the first and second light sources are operable to emit first and second light signals across the recessed portion. For example, first and second laser diodes may be utilized to emit first and second fan beam light signals. Further, the monitoring device may include a light detector array, e.g. a charged coupled device (CCD) array, located on a second side of the recessed portion, opposite to the first side, wherein the first and second light signals may be provided to be detectable along a height of the light detector array. In turn, the light detector array may be operable to provide light detection output signals indicative of magnitudes of light detected at each of a plurality of different pixel locations along at least a portion of the height of the light detector array. Further, the monitoring device may include at least one processor for processing the light detection output signals, wherein when the projecting portion of the cartridge of the disposable urine collection apparatus is located in the recessed portion, the processor(s) is operable to process the light detection output signals to determine a volume and/or level of urine collected within an internal volume of the cartridge of the disposable urine collection apparatus. Further, prior to volume and/or level determinations, the output signals may be initially processed to confirm and/or otherwise register the position of the cartridge relative to a predetermined reference datum.

The monitoring device and disposable urine collection apparatus may be provided so that successive amounts of urine output may be accumulated and discharged from the cartridge over a time interval. In turn, the total volume of such amounts and/or a flow rate corresponding therewith may be determined on an ongoing basis during a time interval and stored for output by the monitoring device. Such output may be provided and updated on an ongoing, periodic basis at a user interface of the monitoring device (e.g. during patient care) and/or to an electronic medical records (EMR) system (e.g. an EMR system of a health care provider).

In contemplated embodiments a first light source (e.g. laser diode) and a second light source (e.g. laser diode) may located at different heights on the first side of the recessed portion (e.g. in vertical offset relation). Further, the first light source and second light source may be provided so that first and second fan beam light signals are detectable along corresponding, at least partially overlapping first and second regions of a height of the light detector array.

In some arrangements, the first light source and second light source may be provided so that, when a projecting portion of a cartridge of a disposable urine collection apparatus is located in the recessed portion, the overlapping first and second regions may combinatively encompass a predetermined height of an internal volume of the projecting portion. Such predetermined height may be greater than a predetermined maximum height of contemplated urine collection within the cartridge of the disposable urine collection apparatus. In some arrangements, the predetermined height may be at least as great as a height of an overflow port provided in the disposable urine collection apparatus.

The first light source may be disposed so that the first center axis of the first fan beam light signal extends at a non-normal angle relative to a longitudinal axis (e.g. a center axis) extending through the recessed portion, and/or the second light source may be disposed so that the second center axis of the second fan beam light signal extends at a non-normal angle relative to such longitudinal axis. In some embodiments, the first light source may be located lower than the light source diode, wherein the first light source may be angled upward and/or the second light source may be angled downward. For example, the first light source e may be angled so that a first center axis of the first fan beam light signal extends at an upward acute angle relative to a first lateral reference plane, and/or wherein the second light source may be angled so that a second center axis of the second fan beam light signal extends from the second light source at a downward acute angle relative to a second lateral reference plane (e.g. wherein the first and second lateral reference planes are parallel). Angulation of the first light source and/or second light source as described above provides for angular passage of the first fan beam light signal and/or second fan beam light signal through the surface of urine collected within the projecting portion of the cartridge throughout urine accumulation, thereby enhancing detection at the light detector array.

In various implementations, the processor(s) may be provided so that, when a projecting portion of a cartridge of a disposable urine collection apparatus is located in the recessed portion, the processor(s) is operable to process the light detection output signals to determine a surface position of collected urine within the projecting portion and to utilize the determined surface position to determine the volume and/or level of urine collected. In one approach, the processor(s) may be operable to process the light detection output signals to obtain values indicative of the magnitudes of light detected at each of the plurality of different pixel locations, and to compare the values to at least one predetermined reference value to identify at least one pixel location at which the detected magnitude is less than the predetermined reference value, thereby indicating a surface position of collected urine. In turn, the processor(s) may be operable to utilize the identified pixel location(s) to determine the volume and/or level of collected urine (e.g. based on predetermined correlations). For example, each of the plurality of pixel locations along the height of the light detector array may have a corresponding predetermined volume and/or level value associated therewith and stored in memory (e.g. a lookup table), wherein the predetermined volume and/or level values increase in corresponding relation to the height of the predetermined pixel locations, and wherein at least one of the predetermined volume values may be utilized to establish the collected urine volume for a given identified pixel location(s).

In some implementations, the urine output monitoring device may include a tilt sensor for sensing an orientation of the monitoring device (e.g. relative to a vertical axis) and for providing a tilt sensor output signal indicative of the sensed orientation. In turn, the processor(s) may be operable to utilize the identified pixel location(s) referenced above and the tilt sensor output signal to determine the surface position of the collected urine and a corresponding volume and/or level associated therewith. For example, the processor(s) may utilize the identified pixel location(s) and tilt sensor output signal, together with one or more predetermined algorithm or lookup table, to determine the volume and/or level of collected urine. In one arrangement, the processor(s) may utilize the tilt sensor output signal and the identified pixel location(s) to generate an initial volume and/or level determination, and may utilize at least one predetermined tilt correction algorithm to determine a tilt correction value that is applied to the initial volume and/or level determination to obtain a determined volume and/or level of urine collected.

In another approach, the processor(s) may utilize the identified pixel location(s) and the tilt sensor output signal together to access a stored lookup table to obtain the determined volume and/or level of urine collected. For example, the tilt sensor output signal may comprise signal components that indicate a direction and an amount, or degree, of angular tilt, (e.g. relative to vertical axis), wherein such signal components may be utilized with the identified pixel location(s) to access a lookup table comprising predetermined values to obtain the determined volume and/or level of urine collected. In one approach, the directional indication component may be an indication of a determined one of a plurality of predetermined angular ranges (e.g. at least four different angular ranges) of a predetermined 360° polar grid (e.g. angular ranges about a vertical axis).

In some implementations, the first and/or second light sources (e.g. laser diodes) may be angled so that an upward acute angle of the first center axis and/or a downward acute angle of the second center axis may be greater than a predetermined acceptable tilt angle (e.g. greater than 10° relative to a vertical axis). In the later regard, in arrangements which include a tilt sensor, the processor(s) may be provided to utilize the tilt sensor output signal to determine whether the monitoring device is physically oriented in an acceptable orientation for operation (e.g. in an orientation having a tilt angle equal to or less than a predetermined acceptable tilt angle).

In contemplated implementations, the processor(s) may be operable to provide control signals to control the operation of the first light source (e.g. laser diode) and/or second light source (e.g. laser diode). In that regard, the processor(s) may be operable to utilize the light detection output signals to generate the control signals. In some embodiments, the control signals may be provided so that only one of the first and second light sources operates at any given time. In one approach, the first light source may be operated for primary urine output monitoring, wherein the second light source is operated only when the processor(s) is unable to determine a collected urine output volume and/or level utilizing light detection output signals generated during operation of the first light source.

In some embodiments, the processor(s) may be operable to provide control signals to cause the first and second light sources (e.g. laser diodes) to emit corresponding first and second fan beam light signals during non-overlapping first and second time periods, respectively. In turn, the processor(s) may be operable to process the light detection output signals corresponding with each of the first and second time periods to obtain corresponding first and second collected urine volume and/or level determinations which may be employed to verify the accuracy of one of the volume and/or level determinations. For example, the two volume and/or level determinations may be compared to obtain a value indicative of any difference therebetween, wherein such value may be utilized by the processor for verification (e.g. when the value is no more than a predetermined acceptable value), and/or to indicate a need for further volume and/or level determination (e.g. when the value is more than a predetermined acceptable value).

In one implementation, the processor(s) may be operable to process the light detection output signals corresponding with one of the first and second time periods noted above to obtain a first determined volume and/or level of collected urine for use, and to compare the first determined volume and/or level to a predetermined value. In turn, if/when the processor determines that the first determined volume and/or level is greater than the predetermined value the processor(s) may be operable to process the light detection output signals corresponding with the other one of the first and second time periods to obtain a second determined volume and/or level of collected urine for use. In conjunction with this approach, it may be appreciated that light detection output signals corresponding with the operation of a lower first light source (e.g. laser diode) may be utilized to determine the volume and/or level of collected urine up to and until the first determined volume exceeds a predetermined value, and thereafter light detection output signals corresponding with the operation of an upper second light source (e.g. laser diode) may be utilized to determine the volume of collected urine.

In some embodiments, the urine output monitoring device may include at least one imaging device that is provided to have an imaging field that encompasses at least a portion of the recessed portion of the monitoring device and is operable to output digital image data of the imaging field, wherein when the projecting portion of the disposable urine collection apparatus is located in the recessed portion, the processor(s) is operable to process the digital image data to determine a volume and/or level of urine collected within the internal volume of the cartridge of the disposable urine collection apparatus. In that regard, the digital image data may be processed to determine a location of the surface of the accumulated urine relative to a predetermined reference datum (e.g. a level and an angle of the surface relative to the reference datum). In turn, a corresponding surface location indicator value (e.g. indicative of the level and an angle of the surface relative to the reference datum) may be generated and utilized by the processor(s) to determine a volume and/or level of urine collected, wherein such volume and/or level determination may be outputted and stored by the monitoring device as otherwise described. Further, based upon a comparison of the urine surface location indicator and one or more predetermined values, the processor(s) may provide control signals to affect the automated discharge and accumulation of urine from the disposable urine collection apparatus, as otherwise described.

In contemplated implementations, a first imaging device may be disposed on a first side of the recess portion of the monitoring device and a second imaging device may be disposed at the back of the recessed portion of the monitoring device (e.g. oriented orthogonal to the first imaging device), wherein the first and second imaging devices have corresponding imaging fields that each encompass at least a portion of the recessed region and are each operable to output corresponding digital imaging data of their respective imaging fields for processing to obtain corresponding first and second surface location indicator values that may be combinatively utilized to determine a volume and/or level of urine collected. The digital imaging data may comprise a series of digital image data frames that are outputted by the first and second imaging devices on a continuous basis (e.g. a video data stream) or predetermined periodic basis during operational use of the monitoring device.

As may be appreciated, the processor(s) of the monitoring device may be configured to provide the above-noted operative functionalities via one or more software modules stored at the monitoring device (e.g. stored in non-transitory memory devices). Such software modules may comprise pre-programmed instructions, algorithms and/or look-up tables.

As noted above, the present disclosure includes embodiments in which a disposable urine collection apparatus may interface with a monitoring device. In that regard, an embodiment of a urine output monitoring system may include a disposable urine collection apparatus that comprises a cartridge having an internal chamber defining an internal volume for collecting urine therein, and a monitoring device to which the disposable urine collection apparatus may be selectively interconnected and disconnected. In some embodiments, the cartridge may include a front portion having a first width, and a projecting portion that extends rearwardly from the front portion and has a second width that is less than the first width.

The monitoring device may include a recessed portion for receiving at least a portion of the cartridge of the disposable urine collection apparatus. For example, for disposable urine collection apparatus having a cartridge that includes a front portion and a projecting portion, as described above, the recessed portion of the monitoring device may be sized to receive all or at least a portion of the projecting portion.

The monitoring device may also include first and second light sources (e.g. laser diodes) disposed at different heights on a first side of the recessed portion, wherein the first and second light sources are operable to emit corresponding first and second light signals in to the received portion of the cartridge of the disposable urine collection apparatus (e.g. a projecting portion). Further, the monitoring device may include a light detector array located along a second side of the recessed portion, opposite to the first side, wherein the first and second light signals are provided to be detectable along the light detector array. In turn, the output signals may be employable by the monitoring device to determine a volume of urine output collected within the internal chamber of the cartridge of the disposable urine collection apparatus.

In some implementations, the disposable urine collection apparatus may comprise a first urine collection device that includes a collection reservoir, as described above, and a separate second urine collection device that includes the cartridge, wherein the second urine collection device is selectively interconnectable to the first urine collection device for discharging accumulated urine from the cartridge to the collection reservoir, as described above. In other implementations, the disposable urine collection apparatus may comprise a collection reservoir fixedly and fluidly interconnected to the cartridge to receive urine accumulated within and/or otherwise flowing through the cartridge.

The monitoring device may include an actuator (e.g. a motor) for providing a first mechanical output. In some embodiments, the monitoring device may also include an actuation member displaceable from a first position to a second position in response to the first mechanical output. Further, the monitoring device may comprise at least one processor operable to process the output signals from the light detector array to determine the volume and/or level of collected urine, as described above, and to provide a first control signal to the actuator when the determined volume and/or level of collected urine is equal to or greater than a first predetermined accumulation amount (e.g. based upon a comparison of the determined volume and/or level of collected urine and the first predetermined accumulation amount), wherein the actuator (e.g. motor) provides the first mechanical output in response to the first control signal. In contemplated embodiments, the disposable urine collection apparatus may further comprise a discharge port, and a valve member positionable to open and close the discharge port. The disposable urine collection apparatus may be provided so that the valve member is displaced from a closed position to an open position in response to the first mechanical output, e.g. displacement of the actuation member from the first position to the second position.

In some arrangements, the processor(s) may be operable to provide a second control signal to the actuator, wherein the actuator provides a second mechanical output in response to the second control signal, and wherein the first and second mechanical outputs are different. The valve member of the disposable urine collection apparatus may be operable to return to the closed position when the actuator provides the second mechanical output. In that regard, the disposable urine collection apparatus may further comprise a biasing member to mechanically bias the valve member to the closed position at the discharge port.

In some arrangements, the processor(s) may be operable to provide the second control signal upon the expiration of a first predetermined time period after the provision of the first control signal. For example, the first predetermined time period may be an amount of time that has been determined to be sufficient to allow for gravity discharge of the accumulated urine volume (e.g. as determined in the manner described herein) from the internal volume of the cartridge. In other arrangements, the processor(s) may provide the second control signal in response to processing of the light detection output signals and a determination that the collected urine has been discharged from the cartridge to at least a predetermined minimum amount (e.g. a predetermined minimum volume and/or level).

In some embodiments, the processor(s) may be operable to provide first control signals, and optionally second control signals, in corresponding relation to each of a predetermined sequence of sets of urine accumulation and discharge operations, wherein for each one of the predetermined sequence of sets of urine accumulation and discharge operations the first predetermined accumulation amount may be different. For example, the first predetermined accumulation amount for at least one set of urine accumulation and discharge operations may be greater than the first predetermined accumulation amount for at least one other set of urine accumulation and discharge operations, e.g. thereby facilitating automatic wash down of condensation accumulation on internal sidewalls of the cartridge. Correspondingly, for each one of the predetermined sequence of sets of urine accumulation and discharge operations, the first predetermined time period may be different. For example, the first predetermined time period of said at least one set of urine accumulation and discharge operations may be greater than the first predetermined time period for said at least one other set of urine accumulation and discharge operations.

As may be appreciated, the processor(s) of the monitoring device may be configured to provide the above-noted operative functionalities via one or more software modules stored at the monitoring device (e.g. stored in non-transitory memory devices. Such software modules may comprise pre-programmed instructions, algorithms and/or lookup tables.

In some embodiments, the monitoring device may be provided so that, when the actuator provides the second mechanical output, the actuation member may return from said second position to said first position. In that regard, the monitoring device may further comprise a biasing member to mechanically bias the actuation member to the first position.

In some arrangements, the actuator of the monitoring device may comprise a motor having an output shaft, wherein the first and second mechanical outputs may comprise rotation and counter rotation of the output shaft, respectively. In turn, the monitoring device may further comprise a cam member, interconnected to the output shaft of the motor, and having a cam surface for engaging an actuation member to move the actuation member from the first position to the second position in response to rotation of the output shaft. In turn, the cam surface may engage the actuation member so as to allow the actuation member to move from the second position to the first position in response to the counter rotation of the output shaft. In some arrangements, such functionality may be provided by a peripheral cam surface having a spiral configuration (e.g. relative to center axis of the output shaft). In conjunction with the utilization of a cam member, the monitoring device may comprise at least one support member, separate from the cam member and output shaft, disposed to supportably engage and thereby provide a load bearing surface for at least one of the cam member and the output shaft.

In some embodiments, the disposable urine collection apparatus of the monitoring system may include a piston member having a bottom end interconnected to the valve member within the internal volume of the cartridge and a top end located outside of the internal volume of the cartridge. A top end member may be interconnected to the top end of the piston member outside of the internal volume of the cartridge, wherein an actuation member of the monitoring device may engage the top end member to lift the top end member, and interconnected piston member and valve member when the actuation member is displaced from the first position to the second position in response to the first mechanical output of the motor.

In contemplated arrangements, the monitoring device may include a support member having a frame portion that defines a recess at the recess portion, wherein the first and second light sources are supportably interconnected to the support member on the first side of the recessed portion, and wherein the light detector array is located by the support member on the second side of the recessed portion. Further, an actuation member of the monitoring device may be located by and moveable between the first and second positions relative to the support member.

In some implementations, the cartridge of the disposable urine collection apparatus may include a hook member that extends rearwardly from a rear face of the projecting portion. In turn, the monitoring device may comprise a latch member that is mechanically biased by a biasing member to an unlatched position, and that is engageable by the hook member of the cartridge to move from the unlatched position into latching engagement with the hook member in a latched position, e.g. thereby interconnecting the disposable urine collection apparatus to the monitoring device. In that regard, the latch member may be located by and moveable between the unlatched and latched positions relative to the support member.

In contemplated embodiments, the latch member of the monitoring device may comprise an exposed top end that is manually engageable by a user to move the latch member from a latched position to an unlatched position so as to permit manual disconnection of the disposable urine collection apparatus from the monitoring device. As may be appreciated, in such embodiments the top end of the latch member may be readily utilized by a user for manual disconnection of the disposable urine collection apparatus when desired, including disconnection to permit ambulatory movement of the patient while maintaining a closed urine collection system between the patient and the disposable urine collection device.

As noted above, in some implementations, a disposable urine collection apparatus may include a first urine collection device and a second urine collection device. The first urine collection device may comprise the collection reservoir, diverter, and reservoir interface as a unit. The second urine collection device may include the cartridge, tubular inlet member, and tubular outlet member(s) as a unit. The second urine collection device may be selectively interconnected to the first urine collection device utilizing interconnection features described above.

In that regard, an embodiment of a urine collection system may comprise a disposable first urine collection device, fluidly interconnectable to a urinal catheter to receive a urine stream, for collecting urine from the urine stream in a collection reservoir of the first urine collection device. The system may further include a disposable second urine collection device, selectively, fluidly interconnectable to the first urine collection device, for collecting urine from the urine stream in a cartridge of the second urine collection device. Further, the system may include a monitoring device, to which the second urine collection device may be selectively interconnectable, for determining a volume of patient urine collected in the cartridge of the second urine collection device.

In a first mode of operation, the first urine collection device may be utilized for collection of urine free from interconnection with either the second urine collection device or the monitoring device. In a second mode of operation, the second urine collection device may be interconnected to the first urine collection device and to the monitoring device for the collection and volume monitoring of urine in the cartridge of the second urine collection device.

The first and second urine collection devices and monitoring device may be provided so that, in the second mode of operation, successive portions of the urine stream are collected in the cartridge of the second urine collection device and discharged to the reservoir of the disposable first urine collection device. In turn, the monitoring device may be provided to determine a total volume of the urine output collected in the cartridge of the second urine collection device over an extend time interval, and/or to determine a flow rate of the urine output.

In some implementations, the disposable second urine collection device of the system may include a discharge port and a valve positionable to close and open the discharge port. In turn, the monitoring device may include an actuation member operable to position the valve member in the open position and to allow the valve member to close in a closed position, as described above. As may be appreciated, additional features of the first urine collection device, second urine collection device and monitoring device may be as described above and further addressed hereinbelow.

As noted, the present disclosure includes various embodiments comprising a monitoring device for interfacing with a disposable urine collection apparatus to determine a volume of urine output collected within the disposable urine collection apparatus, e.g. from a given patient during a time interval. In that regard, an embodiment of a monitoring device may include a processor operable to determine the volume of urine collected during the time interval and/or to determine a urine output flow rate. Further, the monitoring device may include a user interface, operatively interconnected to the processor, and including a user input and a display region to provide one or more screens for displaying a plurality of types of clinical data, e.g. measured clinical parameters. Such plurality may include a first type of clinical data that indicates the volume of urine output collected during a time interval, a second type of clinical data that indicates the urine output flow rate, and/or a third type of clinical data that indicates a measured patient temperature (e.g. a patient temperature obtained utilizing a temperature sensor included with a Foley catheter and operatively interconnected to the monitoring device to provide a temperature output signal).

For at least one screen or a plurality of screens, the display region may comprise a primary display region for displaying one of the plurality of types of clinical data in a primary display size, and at least one secondary display region for displaying additional ones of the plurality of types of clinical data in a secondary display size that is less than the primary display size. For example, the primary display size may be at least 150% of the secondary display size, and in some embodiments, at least 200%.

The user interface may be provided for user selection of the clinical data type to be displayed in the primary display region. In particular, in contemplated embodiments the user input and display region may be defined by a touch panel display, wherein a user may simply touch a selected secondary display region to have the corresponding, displayed clinical data type displayed in the primary display region, wherein the clinical data type previously displayed in the primary display region is displayed in a secondary display region.

In contemplated arrangements, all or at least a portion of the plurality of types of clinical data may be presented as human-readable characters that indicate a magnitude of the given clinical data. By way of example, human-readable characters may be indicative of a volume measure, a patient temperature measure and/or a flow rate measure. For said portion of the plurality of types of clinical data, the primary display size of the human readable characters for the primary display region may be at least 150% of the secondary display size of the human readable characters for the secondary display region.

In some embodiments, for said at least one screen the display region may further include an icon display region for displaying a graphics icon, wherein the user interface may be provided for user selection, using the user input, of the graphics icon, wherein upon said selection at least one of the plurality of types of clinical data may be displayed graphically as a function of time by a corresponding screen in the display region.

In some implementations, for said at least one screen the display region may further comprise a first plurality of icon display regions for displaying a first plurality of different icons corresponding with a plurality of different data input or output functions, wherein the user interface may be provided for user selection, utilizing said user input, of any one of the first plurality of icons, and wherein upon selection of any one of the first plurality of icons, the corresponding data input or output function is enabled by the display of a corresponding screen in the display region. By way of example, each of the first plurality of different icons may be presented free from inclusion of human-readable characters. In some arrangements, the first plurality of different icons may include one or more of the following: a first icon corresponding with a patient information input function; a second icon corresponding with a patient information output function; and, a third icon corresponding with an event marker input function for inclusion of events into a given patient's timeline history during use of the monitoring device. In some embodiments, an icon corresponding with a patient information output function may be provided in the display region for said at least one screen, or in a display region of another screen accessible therefrom (e.g. via touch panel input at the primary display region), wherein upon touch panel selection of such icon a patient data history screen may be accessed that provides historical, time period-based data (e.g. hourly data) for a given patient and parameter type (e.g. any of said plurality of types of clinical data).

In some embodiments, for said at least one screen the display region may further comprise a second plurality of icon display regions for displaying a second plurality of different icons corresponding with a plurality of different status conditions. For example, the second plurality of different icons may include one or more of the following: a first icon corresponding with charge status of at least one rechargeable battery utilized to power the monitoring device; and, a second icon corresponding with a status of connectivity between the processor and an external electronic medical records system.

Additional features and advantages of the present invention will become apparent upon consideration of the further description that follows.

BRIEF DESCRIPTION OF THE DRAWINGS

FIG. 26 is a top view of the embodiment of the bottom member of FIG. 25.

FIG. 27 is a side view of the embodiment of the bottom member of FIG. 25.

FIG. 28 is a back cross-sectional view of the embodiment of the bottom member of FIG. 25 at plane FF shown in FIG. 27.

FIG. 29 is a back view of the embodiment of the bottom member of FIG. 25.

FIG. 30 illustrates another embodiment of a disposable urine collection apparatus.

FIG. 31 illustrates another embodiment of a urine output collection and monitoring system comprising the embodiment of the disposable urine collection apparatus of FIG. 30.

DETAILED DESCRIPTION

Figure 1:
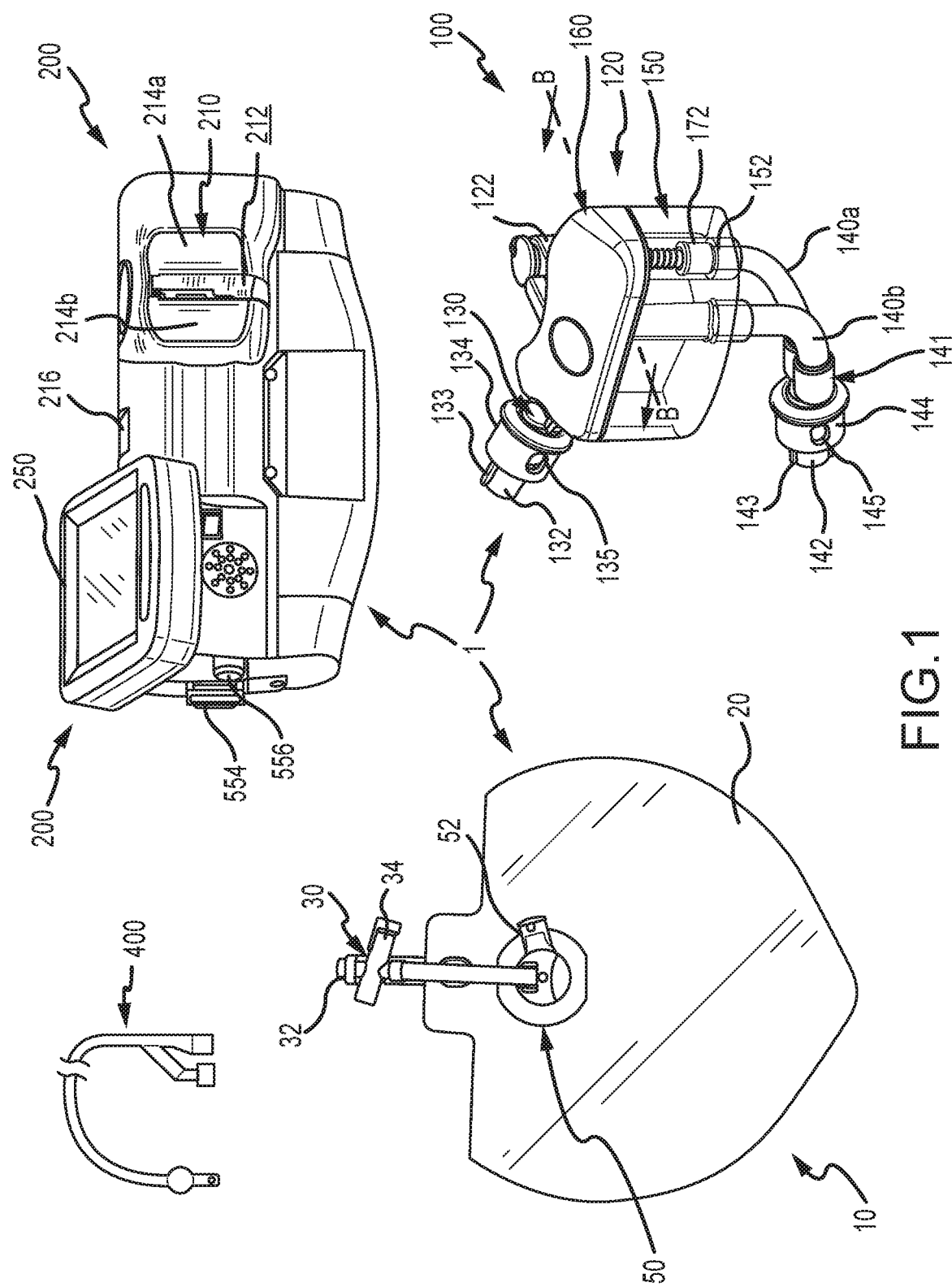
FIG. 1 illustrates one embodiment of a urine output collection and monitoring system that includes interconnectable first and second urine collection devices, and a monitoring device to which the second urine collection device may be interconnected for urine output monitoring.

In the embodiment shown in FIG. 1, a urine output collection and monitoring system 1 may include a urine collection apparatus comprising a first urine collection device 10, and a second urine collection device 100 selectively, fluidly interconnectable to the first urine collection device 10. The urine output collection and monitoring system may further include a monitoring device 200 to which the second urine collection device 100 may be selectively, physically interconnected and disconnected. The first urine collection device 10 and second urine collection device 100 may each be of a disposable nature, i.e. disposable after use with a given patient, while monitoring device 200 may be provided for repeated use with successive patients for urine output volume monitoring. As will be further described, the first urine collection device 10 may be utilized to accumulate urine from a patient for subsequent disposal, e.g. via interconnection to and use of a urinal catheter 400 (e.g. a Foley catheter).

Various features of the embodiment of FIG. 1 may be employed in modified arrangements, including for example arrangements in which features of the first urine collection device 10 and second urine collection device 100 are integrated in a single assembly and/or in arrangements in which the second urine collection device is directly interconnectable to the urinal catheter 400. As such, it should be understood that the descriptions of the embodiments specifically addressed herein are not intended to be limiting.

With respect to the embodiment of FIG. 1, in a first mode of operation, first urine collection device 10 may be utilized in a stand-alone manner to continuously collect urine from a patient. In a second mode of operation, the second urine collection device 100 may be selectively interconnected to the first urine collection device 10 and utilized to collect and discharge successive amounts of patient urine for collection in the first urine collection device 100. In the second mode of operation the monitoring device 200 may be utilized to determine the volume of a patient urine amount(s) successively collected and discharged at the second urine collection device 100 and to provide an output indicative of such amount(s). By way of example, the monitoring device 200 may provide an output indicative of a total volume of patient urine collected and discharged at the second urine collection device 100 over a given interval of time, as well as a urine output flow rate.

Of note, urine output collection and monitoring system 1 allows a given patient to be catheterized for urine collection initially using only first urine collection device 10 in a stand-alone, first mode of operation. Then, if subsequently desired by medical personnel, the first urine collection device 10 may be fluidly interconnected to the second urine collection device 100 and the second urine collection device 100 may be physically interconnected to the monitoring device 200 for urine output volume monitoring in a second mode of operation, free from any need to recatheterize the patient.

The first urine collection device 10 may comprise a collection reservoir 20 having an internal volume sized to facilitate the accumulation of urine from a catheterized patient over an extended time period. For example, the collection reservoir 20 may have an internal volume that may accumulate a urine volume of at least about 1000 ml, and in contemplated embodiments at least about 2000 ml. As may be appreciated, the collection reservoir 20 may be of a flexible construction, e.g. to facilitate packaging and storage prior to use. Further, the collection reservoir may be at least partially light transmissive to facilitate visual observation of the quantity of urine accumulated therein. Optionally, volumetric gradation markings may be provided on the collection reservoir 20.

In the illustrated embodiment, the first urine collection device 10 may further include a diverter 30 and a reservoir interface 50, each of which may be of a rigid or semi-rigid construction. The diverter 30 may include an inlet port 32 and an internal first control member (not shown in FIG. 1) for fluidly interconnecting the inlet port 32 to a first passageway of the diverter 30 in a first position, and for fluidly interconnecting the inlet port 32 to a second passageway of the diverter 30 in a second position, wherein the second passageway extends to an outlet port 34 of the diverter 30.

As will be further described, first urine collection device 10 may be provided so that in the first mode of operation noted above the first flow control member of diverter 30 is in the first position so that the inlet port 32 and first passageway of the diverter 30 are fluidly interconnected to the reservoir interface 50 and internal volume of the collection reservoir 20 via a discharge port of reservoir interface 50 (not shown in FIG. 1). In that regard, the first mode operation provides for stand-alone use of the first urine collection device 10 to accumulate urine from a patient, free from interconnection with second urine collection device 100.

The second urine collection device 100 may comprise a rigid or semi-rigid cartridge 120 having an internal chamber defining an internal volume 124, as shown and described in relation to FIG. 6 below, and a tubular inlet member 130 having an inlet port 132 at a first end and a second end fluidly interconnected to the internal chamber of the cartridge 120. A first interconnection member 134 may be provided at the inlet port 132 for selective interconnection at the outlet port 34 of diverter 30. The second urine collection device 100 may further comprise at least one, and in the illustrated embodiment, two tubular outlet members 140a and 140b. A corresponding first end of each of the tubular outlet members 140a, 140b may be fluidly interconnected to the internal chamber of the cartridge 120. Each of the tubular outlet members 140a, 140b may have a corresponding second end fluidly interconnected to an outlet port 142, e.g. via first and second legs of a tubular Y-member 141. A second interconnection member 144 may be provided at the outlet port 142 for selective interconnection at an inlet port 52 of a passageway of reservoir interface 50.

The reservoir interface 50 may include a second flow control member (not shown in FIG. 1) for closing the passageway of reservoir interface 50 in a first position for operation in the first mode noted above. As will be further described, the second flow control member may be positioned in a second position for operation in the second mode noted above, wherein the passageway of reservoir interface 50 may be fluidly interconnected to collection reservoir 20.

Figure 2:
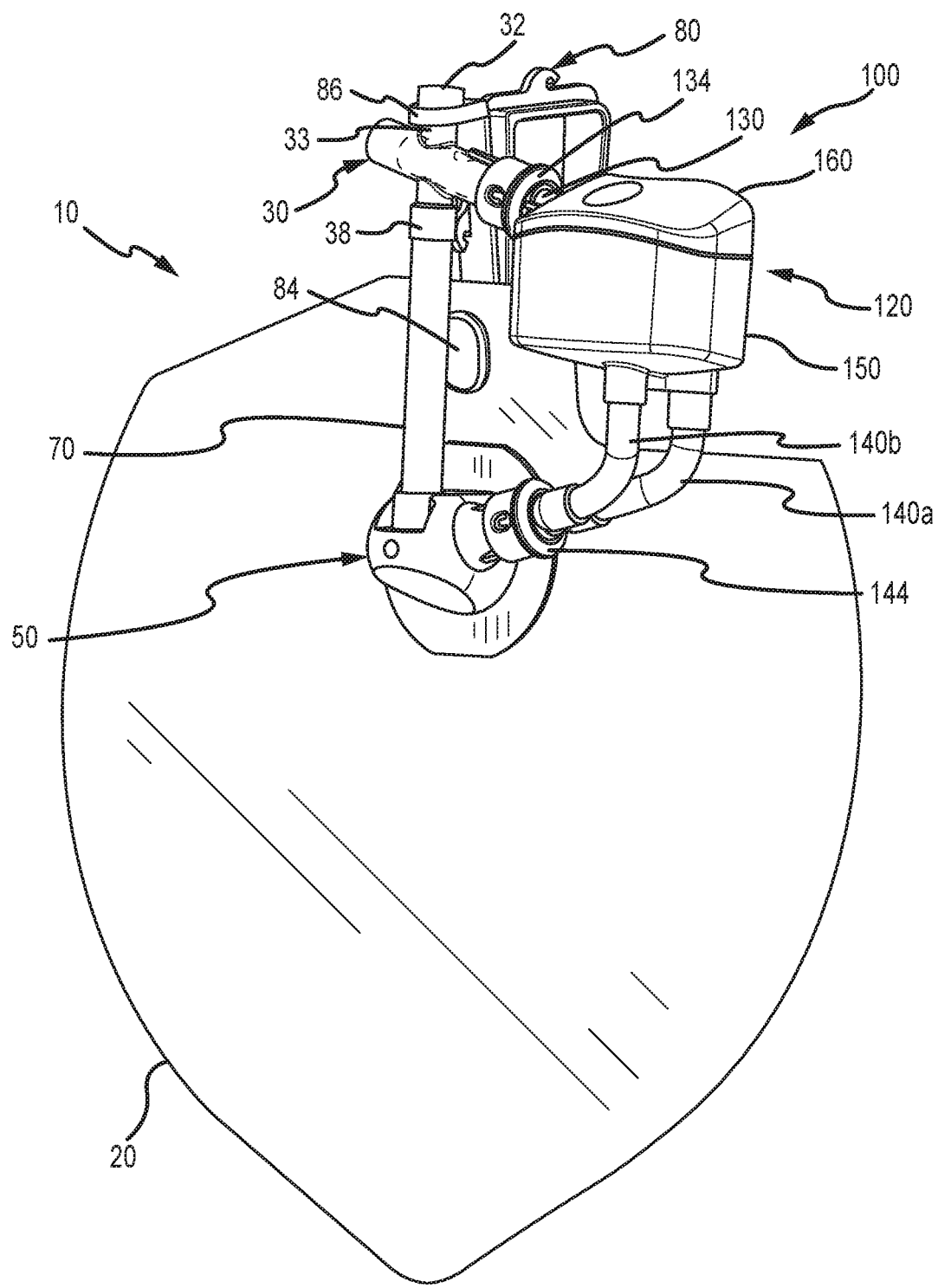
FIG. 2 illustrates the first urine collection device and second urine collection device of the embodiment of FIG. 1, as interconnected for use.

As shown in FIG. 2, the first urine collection device 10 and second urine collection device 100 may be provided so that in the second mode of operation noted above, when the first interconnection member 134 is interconnected to diverter 30 and the second interconnection member 144 is interconnected to reservoir interface 50, with the first flow control member of diverter 30 in the second position, the inlet port 32 and second passageway of diverter 30 are fluidly interconnected to the internal chamber of cartridge 120 via tubular inlet member 130. Further, in the second mode of operation, with the second flow control member of the reservoir interface 50 in the second position, the collection reservoir 20 and passageway of reservoir interface 50 are fluidly interconnected to the internal chamber of cartridge 120 via at least one or both of outlet members 140a, 140b.

With further reference to FIG. 1, monitoring device 200 may comprise an interface portion 210 that is provided for physical interconnection and disconnection of the second urine collection device 100. More particularly, the interface portion 210 may comprise a recessed portion 212 configured to receive a projecting portion 122 of the cartridge 120 of the second urine collection device 100. In one arrangement, the recessed portion 212 and projecting portion 122 may comprise complimentary, or conformal, columnar configurations. In that regard, the cartridge 120 may have a front portion 123 having a first width and the projecting portion 122 may extend rearwardly from the front portion 123 and have a reduced, second width for insert positioning in to the recessed portion 212 of monitoring device 200. As shown, the front portion 123 and projecting portion 122 may be provided so that cartridge 120 is of a T-shaped configuration.

As will be further described, monitoring device 200 may comprise one or more light sources (not shown in FIG. 1) internally located on a first side of the recessed portion 212 (e.g. behind panel portion 214a), and a light detector array (not shown in FIG. 1) located on an opposing second side of the recessed portion 212 (e.g. behind panel portion 214b), wherein light signals may be emitted by the light source(s) across the projecting portion 122 of cartridge 120 for detection at the light detector array. In some implementations at least two light sources (e.g. two laser diode light sources) may be disposed in vertically offset relation on the first side of the recessed portion 212 to emit fan beam light signals. In turn, the light detector array may comprise a charge coupled device that is vertically oriented on the second side of the recessed portion 212 for light detection along the height of a pixel array.

To facilitate light detection at the light detector array, at least a portion of each side wall on each side of the projecting portion 122 of cartridge 120 may be light transmissive. For example, opposing sidewall portions (i.e. sidewall portions that face one another on different sides of the projecting portion 122) may be light transmissive. Further, a front face of or substantially all of the sidewalls of cartridge 120 may be light transmissive to facilitate visual observation of the patient urine collected therein, and optional volumetric gradation markings may be provided on the cartridge 120 (e.g. on the front face thereof).

The light detector array may output signals indicative of magnitudes of light detected along a height of the light detector array (e.g. light detected at each pixel location of a pixel array). In turn, the output signals may be used by monitoring device 200 for monitoring a level and/or volume of urine collected within the internal chamber of cartridge 120. In that regard, the monitoring device 200 may comprise onboard logic for processing the light detector array output signals. For example, the monitoring device 200 may comprise a processor (e.g. a computer microprocessor) for processing the output signals, utilizing pre-programmed instructions/algorithms (e.g. computer software) stored in a non-transitory memory of monitoring device 200. Pursuant to processing of the output signals, the control logic of the monitoring device 200 may determine/store/output information indicative of a volume and/or level of urine collected in cartridge 120. Further, prior to volume and/or level determinations, the output signals may be initially processed to confirm and/or otherwise register the position of cartridge 120 relative to a predetermined reference datum.

In contemplated arrangements, such information may be stored in a memory of monitoring device 200 and outputted (e.g. displayed) at a user interface 250 of the monitoring device 200. Optionally, and as will be further described, such information may also be outputted to an interconnectable communications network (e.g. a hospital information system) for collection processing, and storage of such information in a computer memory (e.g. in an electronic medical records system). The stored/outputted urine collection information may comprise information indicative of a total volume of urine collected from a given patient over an interval of time (e.g. a continuous period during which a given patient is catheterized for urine collection) and information indicative of a rate of patient urine output, wherein the total volume and rate information is generated pursuant to the collection and discharge of successive amounts of patient urine within the internal chamber of cartridge 120.

In one implementation described hereinbelow, each second urine collection device 100 may be provided with unique identification indicia that may be provided to monitoring device 200 in conjunction with the initiation of a second mode of operation as noted above (e.g. provided automatically or manually). The unique identification indicia may be provided by a machine-readable component (e.g. stored in an electronic component (e.g. an RFID tag, a semiconductor chip, etc.), embedded in a coded marking (e.g. a printed barcode or other coded marking), stored in a magnetic stripe, etc.) provided on or in a direct association with the corresponding second urine collection device 100 for automatic reading by a reader device of monitoring device 200 upon or in conjunction with interconnection of the second urine collection device 100 to monitoring device 200. For example, an RFID tag may be attached to the second urine collection device 100 (e.g. on a back sidewall of cartridge 120), and an RFID reader (e.g. an RFID antenna) may be provided in monitoring device 200 to read data stored in the RFID tag. In some implementations, the unique identification indicia may be utilized by monitoring device 200 to authenticate the second urine collection device and thereby enable monitoring device 200 for use as described herein. In any case, the unique identification indicia may be stored in association with and provided together with the stored/outputted urine collection information.

In turn, the unique identification indicia may be utilized to associate the stored/outputted urine collection information with a given patient and corresponding patient records (e.g. in an electronic medical records system). As will be further described, in some implementations (e.g. when desirable to comply with governmental regulations or industry standards), the unique identification indicia may comprise no patient identification data, and any association between the unique identification indicia and a given patient may be separately realized by a given health care provider, e.g. after data output by monitoring device 200 to an electronic medical records system. In other implementations, the unique identification data and/or additional information stored/outputted by monitoring device 200 may include patient identification data that is outputted with the urine collection information.

To facilitate successive receipt, collection and discharge of urine amounts within cartridge 120, the second urine collection device 100 may include a valve member (not shown in FIG. 1) that may be closed and opened to restrict and permit, respectively, gravity urine flow from the internal chamber of cartridge 120 in to outlet member 140a. In turn, monitoring device 200 may comprise an actuator (e.g. a motor) and an actuation member (not shown in FIG. 1) that may interface with the valve member of the second urine collection device 100 to control the opening and closing of the valve member. For such purposes, control logic of the monitoring device 200 (e.g. one or more microprocessors) may be configured to process the light detector array output signals and provide control signals in response thereto, wherein the control signals may be utilized to control the operation of the actuator to effectuate positioning of the actuation member. By way of example, upon a determination by the control logic that the volume and/or level of urine collected within the chamber of cartridge 120 has reached a first predetermined accumulation amount, the control logic may provide control a first signal to the actuator to provide a first mechanical output and thereby position the actuation member to effectuate opening of the valve member of the second urine collection device so that urine collected within the internal chamber of the cartridge 120 may be discharged via outlet member 140a for collection in collection reservoir 20.

Further, a second control signal may be provided to the actuator to provide a second mechanical output and thereby position the actuation member to effectuate closing of the valve member of the second urine collection device so that another volume of urine may be collected in the internal chamber. For example, upon a determination by the control logic that a predetermined time period has passed since the provision of the first control signal to effectuate opening of the valve member of the second urine collection device (e.g. a predetermined time period sufficient for the first predetermined amount of urine to be discharged from cartridge 120 via gravity fluid flow), and/or upon a determination by the control logic (e.g. utilizing the light detector array output signals) that the previously collected urine has been discharged from the internal volume of cartridge 120 to a predetermined minimum amount (e.g. below a predetermined volume and/or level), control signals may be provided to actuator to effectuate closing of the valve member.

In one arrangement, the cartridge 120 of the second urine collection device may be provided so that the internal volume 124 accommodates a collected urine volume of a second predetermined accumulation amount that is at least about two times the first predetermined accumulation amount. In one implementation, the first and second predetermined accumulation amounts may be established to be 30 ml and 60 ml, respectively. In turn, and as will be further described hereinbelow, the cartridge 120 may be provided with an overflow port disposed to provide for automatic gravity discharge of urine when the accumulated urine in cartridge 120 exceeds the second predetermined accumulation amount. For example, the overflow port may be located to avoid the accumulation of greater than the second predetermined accumulation amount of urine.

Relatedly, and as will be further described, the projection portion 122 of cartridge may be provided to have an internal volume height that is at least as great as a height of the overflow port, relative to a common reference plane that is perpendicular to a longitudinal axis extending through the discharge port of the cartridge, thereby allowing for a determination of urine collection amounts up to at least the second predetermined accumulation amount utilizing the light sources, light detector array and control logic of the monitoring device 200.

The urine output collection and monitoring system 1 may be provided to be fully operable when disposed in a vertical orientation and within a predetermined allowed tilt angle relative to a vertical axis. For example, when the second urine collection apparatus 100 is interconnected to the monitoring device 200 at interface portion 210, a longitudinal axis that extends through the recessed portion 212 and projection portion 122 should be parallel to or within a predetermined acceptable tilt angle relative to a vertical axis. A value indicative of the predetermined acceptable tilt angle may be stored in memory that is accessible by control logic of the monitoring device 200.

In order to detect the orientation of monitoring device 200, and in turn second urine collection device 100 interconnected thereto, monitoring device 200 may include a tilt sensor. For example, the tilt sensor may comprise a multi-dimensional accelerometer (e.g. a three dimensional accelerometer). The tilt sensor may provide an output signal indicative of a detected tilt orientation of the monitoring device 200 (e.g. an indication of one or more tilt angle(s) of monitoring device 200 relative to a vertical axis). In turn, the tilt sensor output signal may be employed by the control logic of monitoring device 200 in processing of the output signals of the light detector array for purposes of determining the level and/or volume of urine collected in the second urine collection device 200. For example, the tilt sensor output signal may be employed with the output signals of the light detector array in a predetermined manner (e.g. utilizing a predetermined algorithm or look-up table) to account for the detected tilt orientation in making collected urine level and/or volumetric determinations.

Additionally, the tilt sensor output signal may be employed by the monitoring device 200, together with a predetermined acceptable tilt angle value, to provide an output signal. For example, if the predetermined acceptable tilt angle is exceeded (e.g. as determined by comparison of the detected tilt angle(s) and predetermined acceptable tilt angle), an output signal may be provided to user interface 250 to alert a user (e.g. via a visible and/or audible alarm signal) and/or an output signal may be provided to various components of monitoring device 200 to suspend certain functionalities of monitoring device 200. In some embodiments, the monitoring device 200 may include a visible bubble level, wherein a user may readily adjust the position of the monitoring device into an acceptable orientation by viewing the bubble level.

Figure 3:
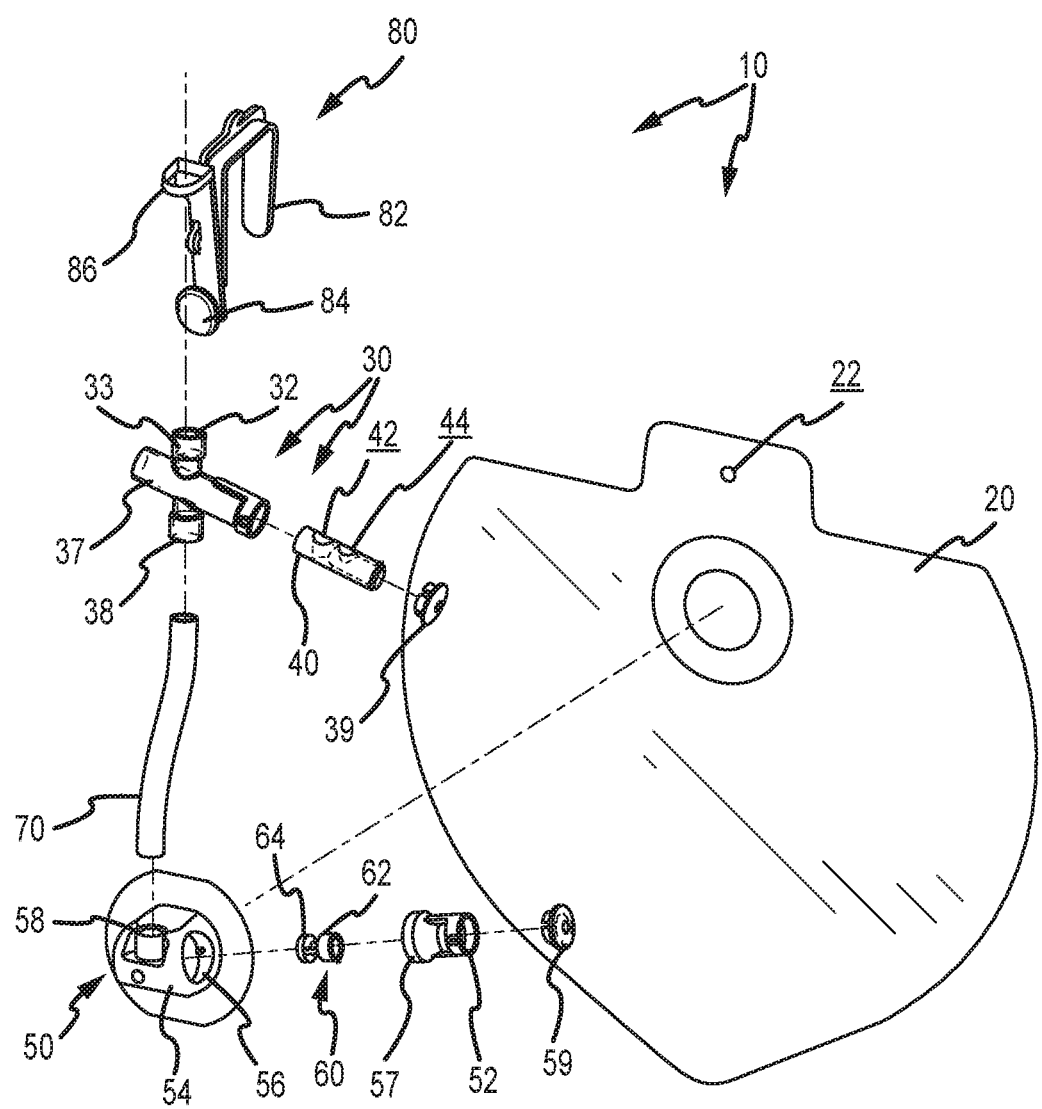
FIG. 3 is an exploded view of the first urine collection device of the embodiment of FIG. 1.
Figure 4:
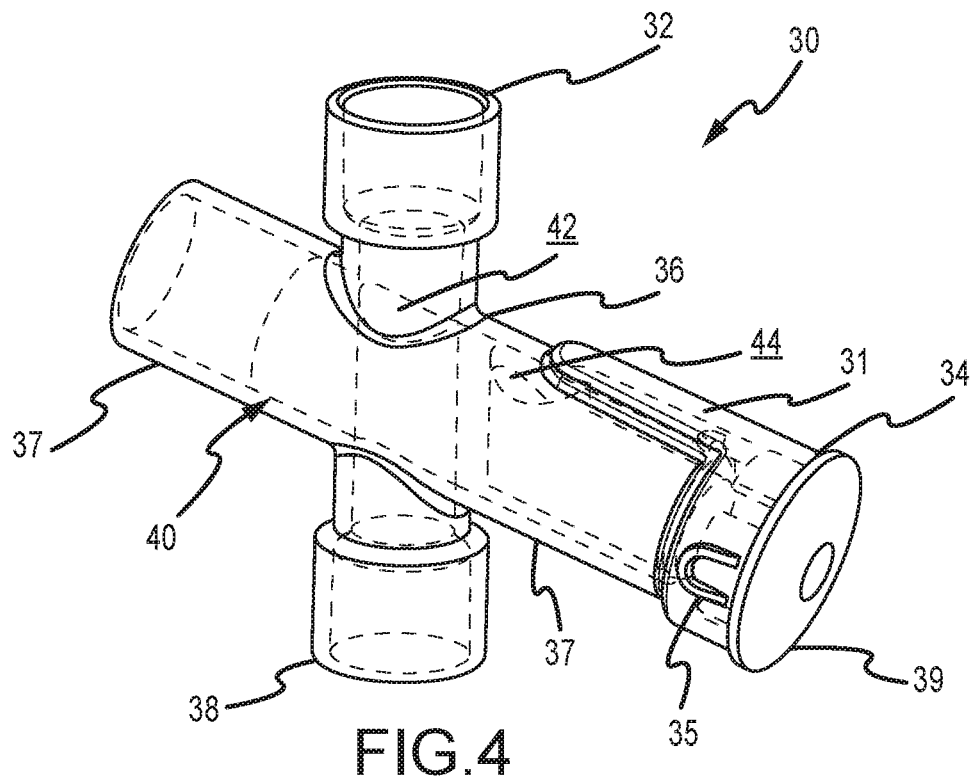
FIG. 4 illustrates a diverter of the first urine collection device of the embodiment of FIG. 1.
Figure 5:
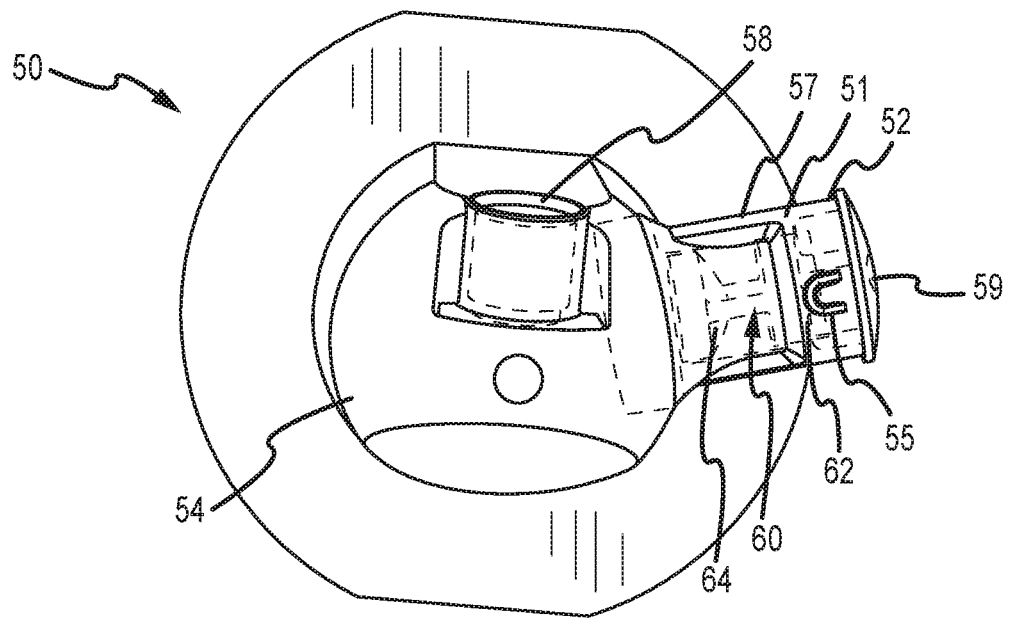
FIG. 5 illustrates a reservoir interface of the first urine collection device of the embodiment of FIG. 1.

Reference is now made to FIGS. 3-5 which further illustrate features of the first urine collection device 10. As shown in FIGS. 3 and 4, the diverter 30 may comprise a diverter housing 36 that defines inlet port 32, outlet port 34 and an interconnection port 38. Further, diverter housing 36 may comprise tubular portions 37 for receipt of cylindrical, first flow control member 40 therewithin. The first flow control member 40 may include a first channel 42 extending therethrough, wherein when the first flow control member 40 is located in the first position for operation in a first mode, as referenced above and shown in FIG. 3, the first channel 42 is located to permit the flow of urine between inlet port 32 and interconnection port 38 via a first passageway that includes the first channel 42. In the illustrated embodiment, the first channel 42 may be of a cylindrical configuration that extends entirely across the first flow control member 40 (e.g. along a first axis that is perpendicular to a center axis of the first flow control member 40). Interconnection port 38 may be fluidly interconnected to a first end of a tubular interconnection member 70 having a second end fluidly interconnected to an interconnection port 58 of reservoir interface 50. As may be appreciated, interconnection member 70 provides for urine flow therethrough in the first mode of operation and accommodates vertically offset positioning of diverter 30 and reservoir interface 50. In turn, gravity urine flow in both the first mode of operation and the second mode of operation is accommodated.

With further reference to FIGS. 3 and 4, first flow control member 40 may also include a second channel 44 extending therethrough, wherein when the first flow control member 40 is positioned in the second position referenced above for operation in a second mode as referenced above e.g. by displacing the first flow control member 40 away from the outlet port 34, the second channel 44 may be located to permit the flow of urine between inlet port 32 and outlet port 34 via a second passageway that includes the second channel 44. In the illustrated embodiment, the second channel 44 may be of an L-shaped configuration that first extends across a portion of the first flow control member 40 and then extends within the first flow control member 40 to an end thereof (e.g. first along a second axis that is perpendicular to the center axis of the first flow control member 40, and then along the center axis of the first flow control member 40).

In one arrangement, the inlet member 130 of the second urine collection device 100 may be provided so that the first end thereof engages and displaces the first flow control member 40 from the first position to the second position described above when the first interconnection member 134 is interconnected at the outlet port 34 of the diverter. For such purposes, the first end of the inlet member 130 may be slidably received within the tubular portion 47 at port 34.

As illustrated by FIG. 4, when the first flow control member 40 is in the first position, as described above, the second passageway of diverter 30 is closed (e.g. the inlet end of the second channel 44 is closed at a wall interface with tubular portion 37). Further, when the first flow control member is in the second position, as described above, the first passageway of diverter 30 is closed (e.g. inlet end of first channel 42 is closed at a wall interface with tubular portion 37).

As shown in FIGS. 3 and 5, reservoir interface 50 may comprise an interface housing 54 having an internal chamber in fluid communication with the collection reservoir 20. Reservoir interface 50 may function as an anti-reflux chamber. The interface housing 54 may define an inlet aperture 56 and the interconnection port 58 referenced hereinabove. The inlet aperture 56 may be configured to fixedly receive a tubular port member 57 therein, wherein the port member 57 defines the passageway and the inlet port 52 of reservoir interface 50 referenced hereinabove. Further, second control member 60 may be seated within the port member 57. In that regard, the second flow control member 60 may be provided so that when the second flow control member 60 is located in the first position, as referenced above and shown in FIG. 5, the second flow control member 60 closes the passageway through the port member 57, and so that when the second flow control member 60 is located in a second position, e.g. by displacing the second flow control member 60 away from the inlet port 52, the second flow control member opens the passageway through port member 57.

In the illustrated arrangement, the second flow control member 60 may include a first end portion 62 having a channel extending therethrough, and a closed second end portion 64. In turn, when the second flow control member 60 is displaced to the second position a portion of the channel of the first end portion 62 is displaced in to the internal chamber of the interface housing 54.

In one arrangement, a tubular portion of Y-member 141 may be provided so that a first end thereof defines outlet port 142 and engages and displaces the second flow control member 60 from the first position to the second position described above when the second interconnection member 144 is interconnected at the inlet port 52 of reservoir interface 50. For such purposes, the first end of the tubular portion of Y-member 141 may be slidably received within the tubular port member 57 at inlet port 52.

Referring now to FIGS. 2 and 3, the first urine collection device 10 may include a hangar member 80 having a downward-oriented first hangar 82 and an upward-oriented second hangar 84. The second hangar 84 includes an enlarged head for positioning through an opening 22 of collection reservoir 20, wherein the collection reservoir 20 may supportably hang from the hangar member 80. Further, hangar member 80 may include a support loop 86 for receiving an upstanding tubular portion 33 of the diverter housing 36 therethrough. The first hangar 82 is provided for supportably hanging the first urine collection device 10 on a support for a first mode of operation (e.g. a support defined by a rolling bedside stand), and for supportably hanging both the first urine collection device 10 and interconnected second urine collection device 100 from a support in a second mode of operation. In the later regard, the first hangar 82 may be of a down-oriented, U-shaped configuration so as to hook over and hang from a complimentarily configured surface region 216 of monitoring device 200 (shown in FIG. 1), as will be further described below. In turn, the monitoring device 200 may be supported by a stand (not shown). More particularly, a rollable support stand may be provided to retainably support the monitoring device 200 at a desired position. For example, a back panel of monitoring device 200 may be provided with securement members to selectively mount monitoring device 200 to a support stand.

As illustrated in FIGS. 1 and 3-5, a removable first cap member 39 may be provided for capping the outlet port 34 of the diverter 30, and a removable second cap member 59 may be provided for capping the inlet port 52 of the reservoir interface 50. The first and second cap members 39, 59, may be disposed in capped relation to the outlet port 34 and inlet port 52, respectively, prior to and during the first mode of operation noted above. In the event that patient urine output monitoring is desired, the first and second cap members 39, 59 may be removed from the outlet port 34 and inlet port 52, respectively, to allow for interconnection and operation of the first urine collection unit 10 and second urine collection unit 100 in the second mode of operation noted above.

As noted above, a first interconnection member 134 may be provided at inlet port 132 of tubular inlet member 130 and a second interconnection member 144 may be provided at the outlet port 142 of the tubular outlet members 140a, 140b. Further, the first interconnection member 134 and the diverter 30 may be provided so that, upon interconnection of the inlet port 132 and outlet port 34, such components are not disconnectable. For example, the first interconnection member 134 and the outlet port 34 may be configured for one-way locking engagement. For such purposes, the first interconnection member 134 may include at least one aperture 135, and preferably at least two apertures 135 disposed to receive at least one spring-loaded tab member 35, and preferably at least two circumferentially offset, spring-loaded tab members 35 provided on a tubular portion 37 of diverter housing 30 upon advancement of the first interconnection member 134 along tubular inlet member 130 and about and along the tubular portion 37 to yield a snap-fit engagement therebetween.

Similarly, the second interconnection member 144 and reservoir interface 50 may be provided so that, upon interconnection of outlet port 142 and inlet port 52, such components are not disconnectable. For example, the second interconnection member 144 and the inlet port 52 may be configured for one-way locking engagement. For such purposes, the second interconnection member 144 may include at least one aperture 145, and preferably at least two apertures 145 disposed to receive at least one spring-loaded tab member 55, and preferably at least circumferentially offset, spring-loaded tab members 55, provided on port member 57 upon advancement of the second interconnection member 144 along the tubular portion of Y-member 141 and about and along port member 57 to yield a snap-fit engagement therebetween.

Optionally, the outlet port 34 of diverter 30 and the inlet port 132 of tubular inlet member 130 may be provided to have first complementary configurations for mating engagement, and the outlet port 142 for the outlet members 140a, 140b and the inlet port 52 of the reservoir interface 50 may be provided to have second complementary configurations for mating engagement. The first complementary configurations and second complementary configurations may be different so as to physically preclude mating engagement of the outlet port 34 of the diverter 30 with the outlet port 142 for the outlet members 140a, 140b, and to preclude mating engagement of the inlet port 132 of the inlet member 130 with the inlet port 52 of the reservoir interface 50.

For example, the inlet member 130 may be provided with at least one outwardly-projecting spline 133 that extends from port 132 along at least a portion of the inlet member 130, and interfacing tubular portion 37 of diverter 30 may be provided with at least one outwardly-projecting channel 31 sized and/or otherwise disposed to slidably receive the spline(s) 133 therewithin, wherein the spline(s) 133 and channel(s) 31 may define first complimentary configurations. Similarly, the tubular portion of Y-member 141 that defines port 142 may be provided with at least one outwardly-projecting spline 143 that extends from port 142 along at least a portion of the tubular portion, and the port member 57 may be provided with at least one outwardly-projecting channel 51 sized and/or otherwise disposed to slidably receive the spline(s) 143 therewithin, wherein the spline(s) 143 and channel(s) 51 may define second complimentary configurations. By different sizing and/or placement of the spline(s) 133 and channel(s) 31, relative to the spline(s) 143 and channel(s) 51, the first complimentary configurations and second complimentary configurations may preclude the undesired interconnection of noted components.

Figure 6:
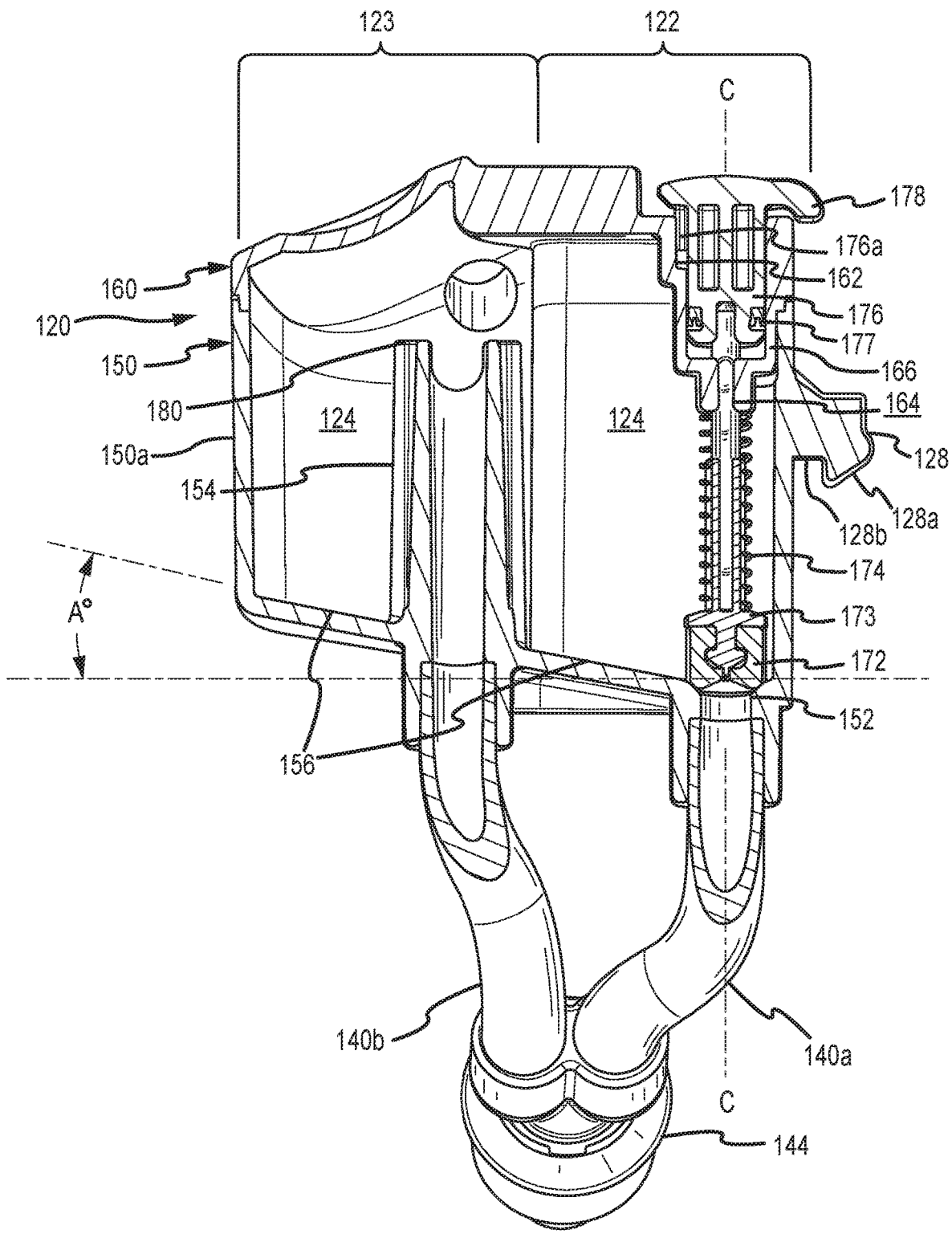
FIG. 6 is a side cross-sectional view of the second urine collection device of the embodiment of FIG. 1 at plane BB shown in FIG. 1.
Figure 7:
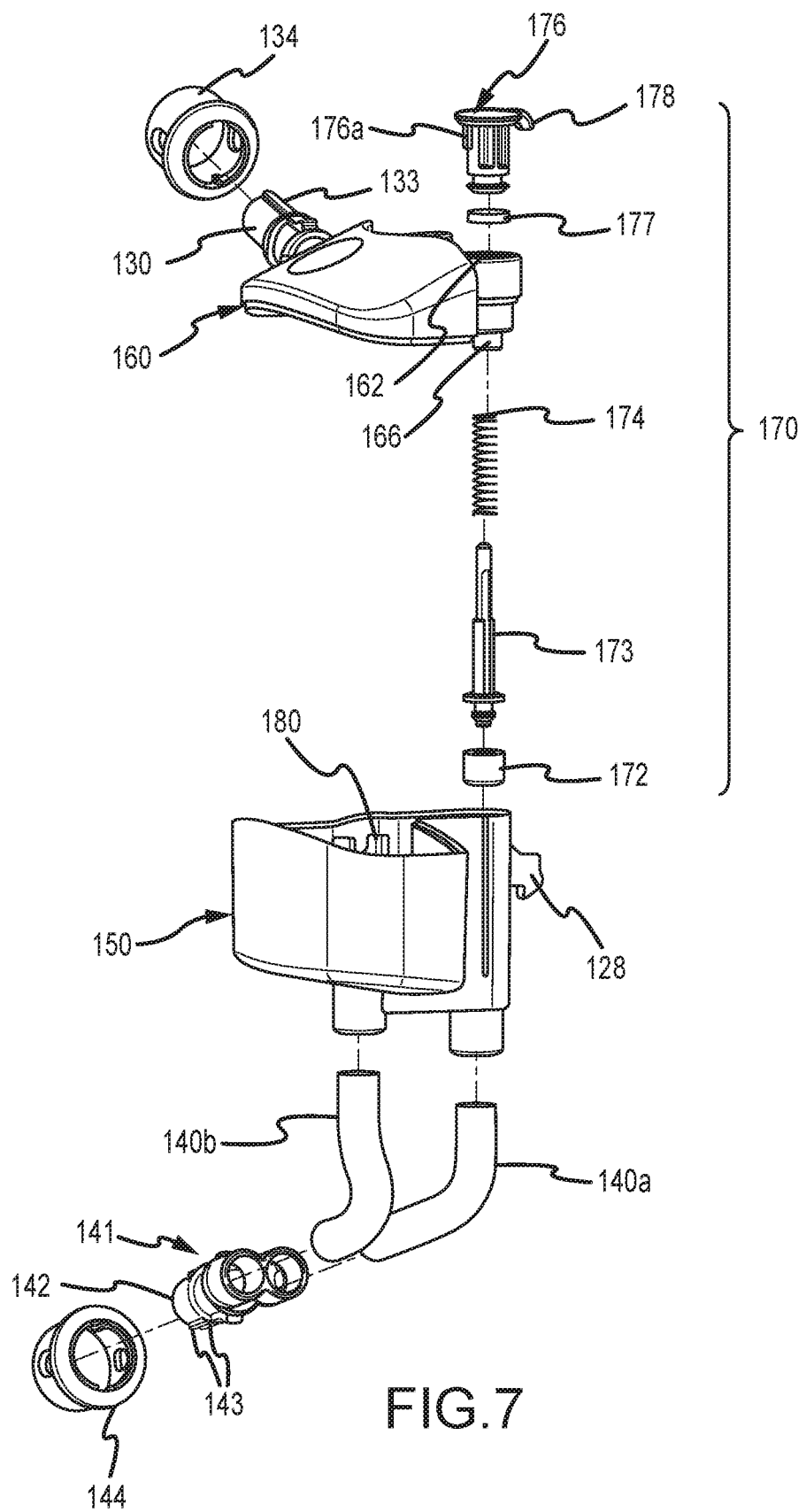
FIG. 7 is an exploded view of the second urine collection device of the embodiment of FIG. 1.

Reference is now made to FIGS. 6 and 7 which illustrate further features of the second urine collection device 100. In particular, FIG. 6 is a cross-sectional view of the second urine collection device 100 at plane BB shown in FIG. 1, and FIG. 7 is an exploded view of the second urine collection device 100. As shown, the cartridge 120 may comprise a bottom member 150, and a top member 160 that may be fixedly interconnected to the bottom member 150 to define the internal volume 124 of cartridge 120 upon assembly of the second urine collection device 100.

The bottom member 150 may include a discharge port 152 to fluidly interconnect the internal volume 124 to the tubular outlet member 140a. As shown in FIG. 6, the discharge port 152 may be located within the projecting portion 122 of cartridge 120. In turn, and as noted above, the second urine collection device 100 may include a valve member 172 that may be provided to selectively open and close the discharge port 152. The valve member 172 may be provided as a component of a discharge valve assembly 170 that is also located in the projecting portion 122 of cartridge 120.

In addition to the valve member 172, the discharge valve assembly 170 may include a piston member 173 interconnected at a bottom end to the valve member 172, a spring member 174 (e.g. a coil spring) positioned about and along the piston member 173, a top end member 176 interconnected to a top end of the piston member 173, and an annular seal member 177 positioned about an annular recess of the top end member 176. As illustrated in FIG. 6, the top end member 176 and seal member 177 may be slidably positioned within a recessed portion 162 of the top member 160, and a top end portion of the piston member 173 may slidably extend through an opening 164 of a hub region 166 of the top member 160 provided below the recessed portion 162. In turn, upon assembly of the cartridge 120, the spring member 174 may be captured in a partially compressed state between the valve member 172 and the hub region 166, wherein the valve member 172 may be biased downward so as to close the discharge port 152.

The top end member 176 may include a projecting arm 178. As noted above and further described below, the monitoring device 200 may include an actuator (e.g. a motor) for providing a first mechanical output to cause an actuation member to engage the arm 178 so as to apply a force (e.g. an upward force) to lift and thereby displace the top end member 176 and seal member 177, together with the interconnected piston member 173 and valve member 172, relative to the bottom member 150 and top member 160 of cartridge 120, and thereby open the discharge port 152 to allow for gravity discharge of accumulated urine within internal chamber 124 via tubular outlet member 140a. As may be appreciated, the actuator of monitoring device 200 may be controlled so as to apply a force to arm 178 via the actuation member, and thereby displace valve member 172 to open discharge port 152, when a predetermined amount of urine has accumulated in the internal volume 124. Further, when the accumulated urine is discharged the actuator may provide a second mechanical output, wherein the force applied to arm 178 by the actuation member may be terminated, thereby allowing the valve member 172 to be biased back to a closed position at discharge port 152 by spring member 174.

The discharge valve assembly 170 may be provided so that the top end member 176 may be manually raised, together with entire discharge valve assembly 170, then rotated from a home position to a rotated position, wherein when the top end member 176 is in the elevated, rotated position, the valve member 172 may be maintained in an open position. In turn, the top end member 176 may be manipulated to manually rotate the top end member 176 back to the home position, wherein the valve member 172 may return to a closed position.

In one approach, the top end member 176 may include at least one projecting rib 176a and the recessed portion 162 may comprise at least one groove sized to slidably receive the rib(s) 176a. In turn, when the top end member 176 is manually raised to at least a predetermined height at which the rib(s) 176a exits the groove(s), the top end member 176 may be rotated and released so that a bottom end of the rib 176a may engage a top surface of top member 160 of cartridge 120 and thereby be maintained in the rotated position with the spring member 174 applying a downward biasing force to the top end member 176. When the top end member 176 is manually rotated back to the home position the rib(s) 176a may realign with the groove(s) of the recessed portion 162, whereupon the top end member 176 may be released so that the top end member 176 may slidably advance back downward into the recessed portion 162 and the valve member 172 will return to a biased closed position at discharge port 152. In some implementations, the second urine collection device 100 and monitoring device 200 may be configured so that, when the top end member 176 retained at the predetermined height, the second urine collection device 100 cannot be interconnected to the monitoring device 200.

To facilitate urine discharge from internal volume 124, all or at least a portion of a bottom surface 156 of the internal volume 124, as defined by bottom member 150, may be of a planar configuration and oriented to extend rearward and downward from a front face 150a of the cartridge 120 at an angle of A°, relative to a reference plane that is perpendicular to a longitudinal axis CC extending through the discharge port 152. The angle A° may be provided to be at least about 11°, and in some embodiments at least 15°. Additional configurations and features of bottom surface 156 are described hereinbelow.

In addition to discharge port 152, the second urine collection device 100 may include an overflow port 180 within the internal volume 124 of the cartridge 120. In the embodiment illustrated in FIG. 6, the overflow port 180 may be defined by an upstanding tubular portion 154 of bottom member 150 that extends upward from the bottom surface 156 thereof. A bottom end of the tubular portion 154 may be interconnected fluidly to the tubular outlet member 140b.

As described above, the overflow port 180 may be provided so that, in the event an amount of urine collected within the cartridge 120 exceeds a second predetermined accumulation amount (e.g. corresponding with the top end of the tubular portion 154), any additional urine accumulating within the cartridge 120 will result in urine flow in to the tubular portion 154 for gravity discharge via tubular outlet member 140b. As further described above, the cartridge 120 and outlet port 180 may be provided so that the second predetermined accumulation amount is at least about two times greater than the first predetermined accumulation amount at which the monitoring device 200 may be provided to effect the automatic opening of valve 172 for urine discharge. In one arrangement, the first predetermined accumulation amount may be established to be about 30 ml and the overflow port 180 may be provided to establish a second predetermined accumulation amount of at least about 60 ml.

The provision of a cartridge 120 and an overflow port 180 as described above facilitates disconnection of the second urine collection device 100 from the monitoring device 200, while maintaining fluid interconnections between the second urine collection device 100, first urine collection device 10 and urinary catheter 400, so that urine collection in the cartridge 120 may be continuously provided during disconnection. Such arrangement facilitates temporary, ambulatory patient activity (e.g. for imaging and/or other medical procedures). Following such disconnection, the second urine collection device 100 may be again interconnected to the monitoring device 200 and unique identification indicia embodied in a machine readable component (e.g. an RFID tag) may be automatically read by a reader device of monitoring device 200 for use as described herein (e.g. to authenticate the second urine collection device 100 and to associate the second urine collection device 100 and subsequent stored and/or outputted data with previously stored and/or outputted data). In turn, the monitoring device 200 may be provided so that, upon such interconnection, the light sources and light detector array of monitoring device 200 are operable so that light detector array provides output signals for processing by the control logic to determine the volume and/or level of urine collected in cartridge 120. After such determination, if or when the accumulated urine volume and/or level exceeds the first predetermined accumulation amount described above, the control logic may provide control signals to effect opening of valve 172 to discharge the accumulated urine.

As may be appreciated, in addition to providing for overflow discharge of collected urine from cartridge 120, overflow port 180 may be provided to also function to allow for gas passage from the internal volume 124 and through the outlet member 140b for venting at the collection reservoir 20 (e.g. via a hydrophobic gas vent). Such venting may reduce pressurization within cartridge 120 during urine accumulation.

As illustrated in FIG. 6, at least a portion of the projecting portion 122 of cartridge 120 may be provided to have an internal volume height that is at least as great as the height of the overflow port 180 relative to a reference plane that extends perpendicular to the longitudinal axis CC extending through the discharge port 152 of the cartridge 120, at or immediately above the discharge port 152. In turn, the light sources and the light detector array of the monitoring device 200 may be provided so that such internal volume of the projecting portion 122 is included within the area across which light signals are provided and detected for urine volume determinations by monitoring device 200.

As further illustrated in FIGS. 6 and 7, the bottom member 150 of the cartridge 120 may include a rearwardly-projecting, downward-oriented hook member 128 to facilitate interconnection of the second urine collection device 10 to the monitoring device 200 in an upright orientation. For example, the hook member 128 may include an angled ramp 128a and adjacent, downward-facing notch 128b for snap-in engagement with complimentary configured ramp of a latch member of monitoring device 200, as will be further described.

As noted above, to facilitate light detection at the light detector array of monitoring device 200, at least a portion of each side wall on each side of the projecting portion 122 of cartridge 120 may be light transmissive. For example, opposing sidewall portions (i.e. sidewall portions that face one another on different sides of the projecting portion 122) may be light transmissive. Further, a front face 150a of the front portion 123 or substantially all of the sidewalls of cartridge 120 may be light transmissive to facilitate visual observation of the patient urine collected therein, and optional volumetric gradation markings may be provided on the cartridge 120 (e.g. on the front face 150a thereof) to facilitate manual logging of patient urine output.

Optionally, internal surfaces of at least opposing sidewall portions of the projecting portion 122 may be hydrophobic to reduce condensation accumulation. In one approach, such surfaces may have a hydrophobic coating applied thereto (e.g. a superhydroscopic coating providing a nanoscopic surface layer). In conjunction with such approach, substantially all of the internal surfaces of the cartridge 120 may be hydrophobic to reduce condensation accumulation, thereby facilitating both automated and manual urine accumulation detection.

Figure 22:
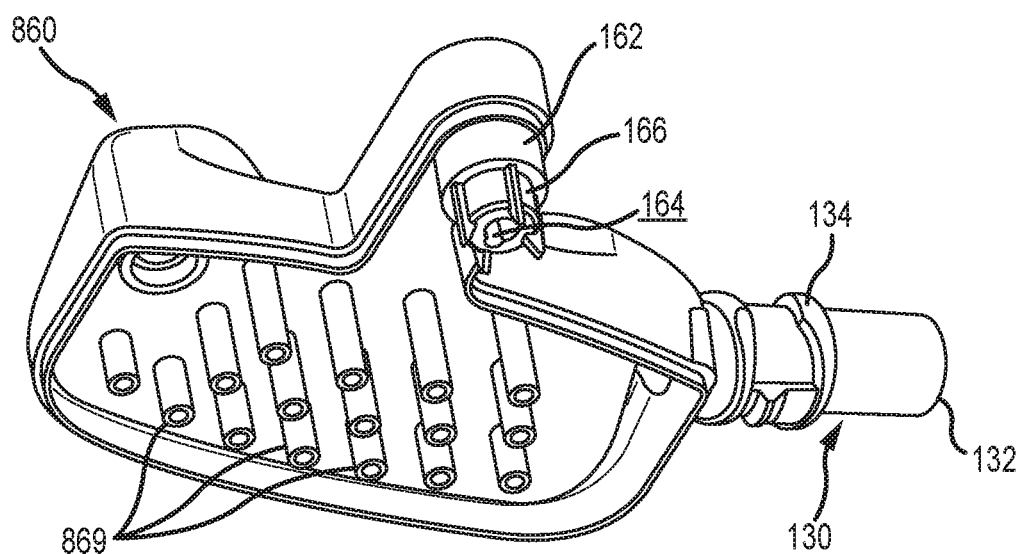
FIG. 22 is a perspective view of an embodiment of a bottom member employable in the cartridge of the second urine collection device of the embodiment of FIG. 1.

Another embodiment of a top member 860 for use in place of top member 160 in cartridge 120 is shown in FIG. 22. As illustrated, the top member 860 may comprise various features as described above in relation to top member 160, and corresponding reference numerals are therefore utilized in relation to such features.

The top member 860 may define an upper surface of the internal volume 124 of cartridge 120 and may comprise one or more nucleation members 869 that project downward in to the internal volume 124 to provide nucleation sites for condensation droplets. In that regard, condensation droplets may readily form on and drop off nucleation members 869 to reduce condensation accumulation on the internal sidewalls of cartridge 120. As shown in FIG. 22, a plurality of nucleation members 869 may be provided to project downward (e.g. in stalactite manner and configuration) within the front portion 123 of the cartridge 120. The nucleation members 869 may be of a tubular configuration to enhance droplet formation on the inner and outer surfaces thereof. Further the nucleation members 869 may taper down from top to the bottom to facilitate droplet release.

Figure 23:
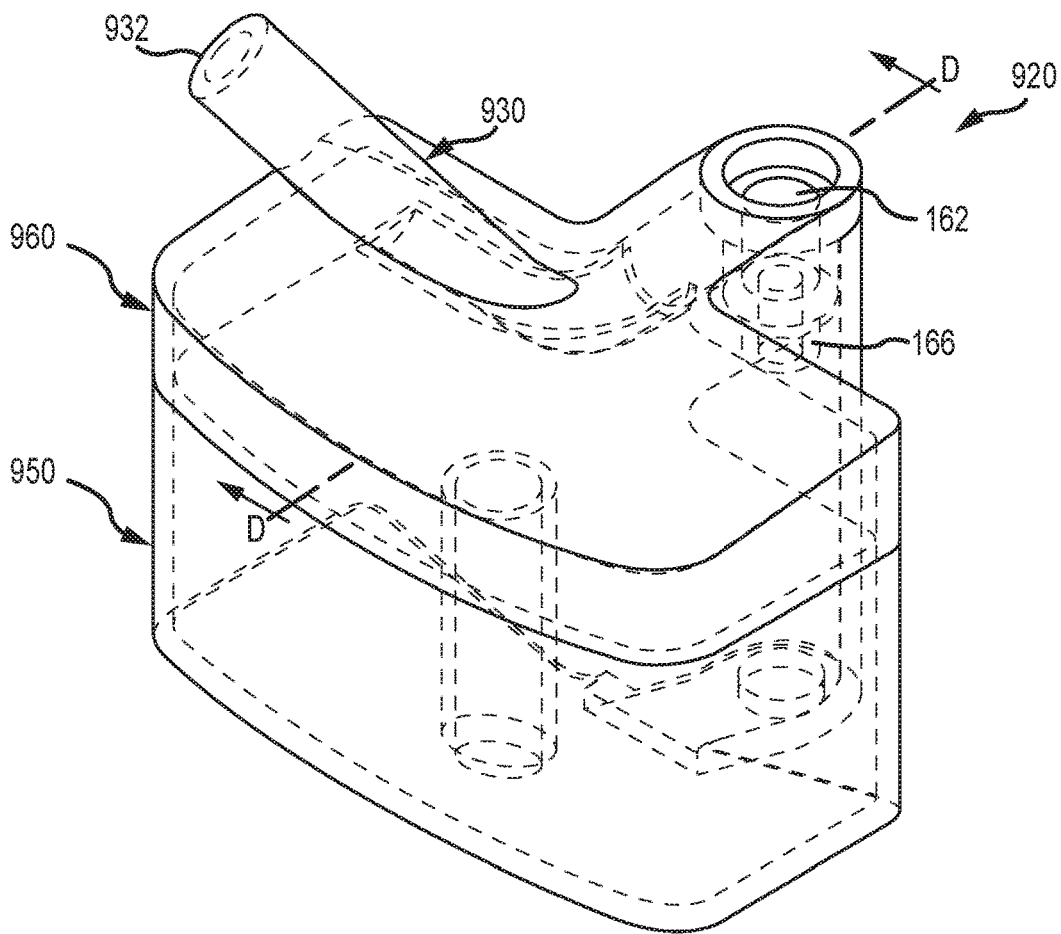
FIG. 23 is a perspective view of an embodiment of a cartridge employable in the second urine collection device of the embodiment of FIG. 1.
Figure 24:
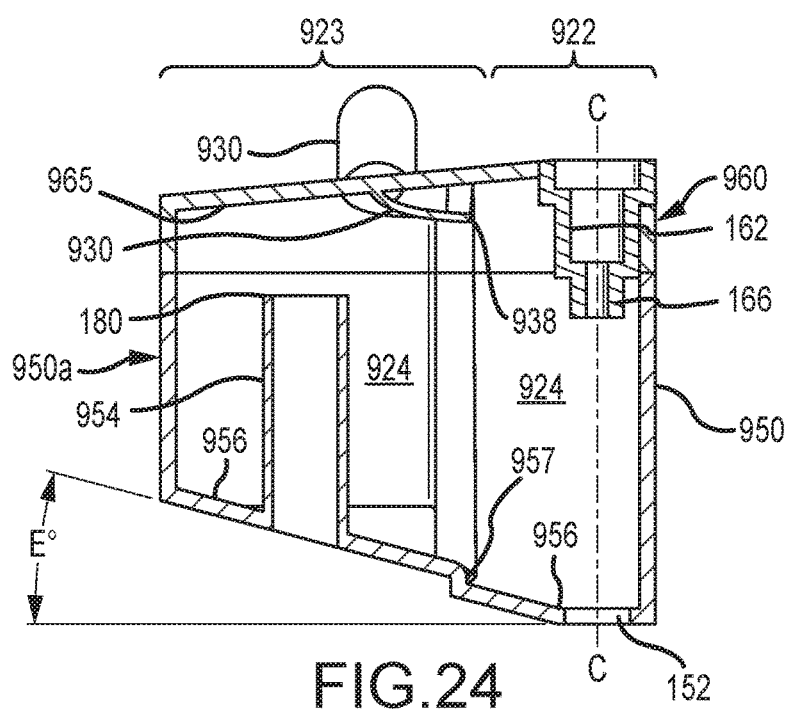
FIG. 24 is a side cross-sectional view of the embodiment of the cartridge of FIG. 23 at plane DD shown in FIG. 23.
Figure 25:
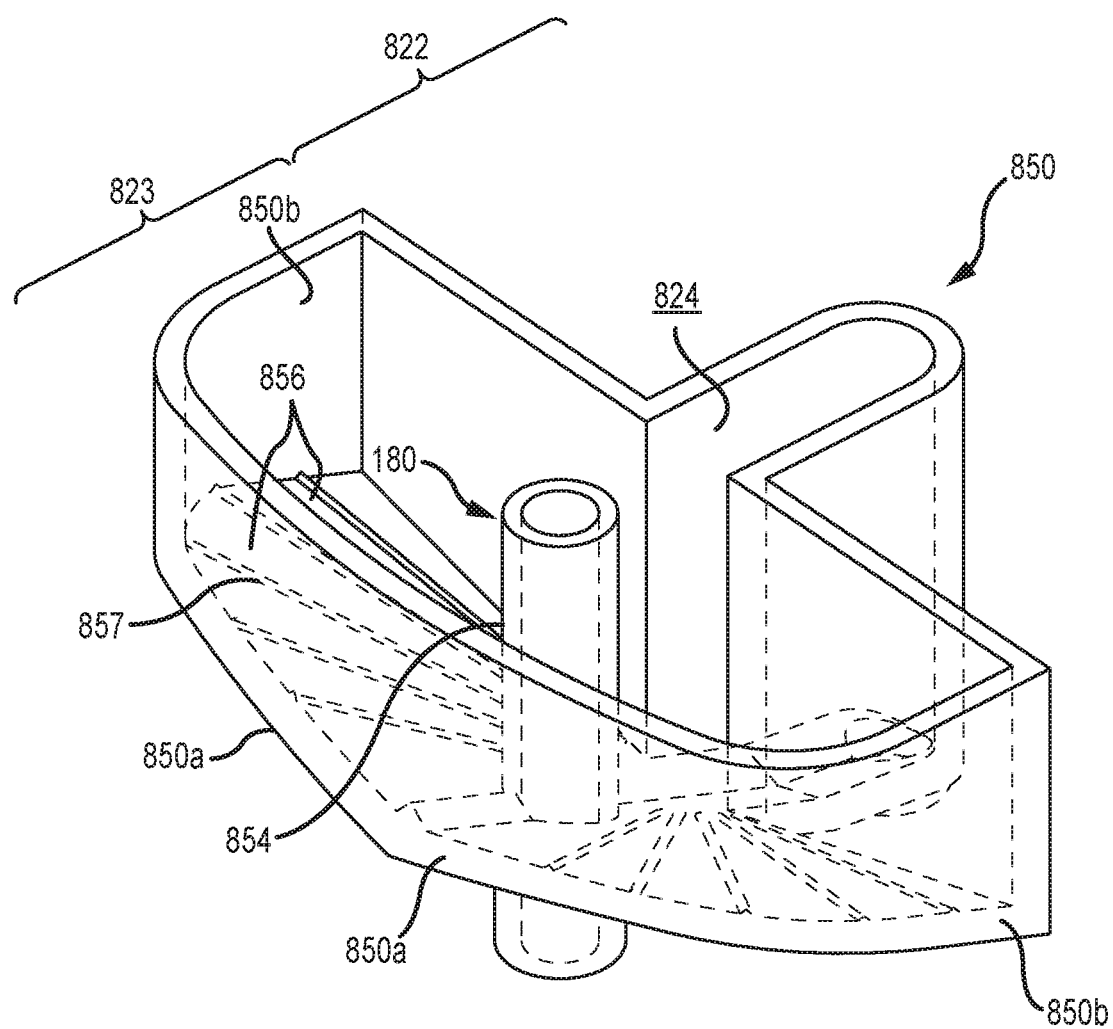
FIG. 25 is a perspective view of another embodiment of a bottom member employable in the cartridge of the second urine collection device of the embodiment of FIG. 1.

Another embodiment of a cartridge 920 for use in place of cartridge 120 is shown in FIGS. 23 and 24. As illustrated, the cartridge 920 may comprise various features as described above in relation to cartridge 120, and corresponding reference numerals are therefore utilized in relation to such features.

The cartridge 920 may include a bottom member 950 and top member 960. The bottom member 950 may define a bottom surface 956 that extends rearward and downward from a front face 950a of a front portion 923 of the cartridge 920 to a projecting portion 922 thereof, thereby facilitating urine accumulation/detection within the projecting portion 922 and urine discharge through discharge port 152. The bottom surface 956 may include a downward step 957 at an interface between the front portion 923 and the projecting portion 922 of the cartridge 920 so as to facilitate urine flow in to and accumulation/detection in the projecting portion 922.

In the front portion 923 and projecting portion 922 of cartridge 920, the bottom surface 956 may extend rearward and downward at an angle of E° relative to a reference plane that is perpendicular to a longitudinal axis CC extending through the discharge port 152. Bottom surface 956 may be provided so that E°≥11°, and in some embodiments E°≥15°. At the downward step 957, the bottom surface 956 may extend downward at an angle of at least 45° relative to such reference plane (e.g. an angle of about 90° relative to the reference plane in the embodiment illustrated in FIG. 24).

As shown in FIGS. 23 and 24, the cartridge 920 may include a tubular inlet member 930 having an inlet port 932 at a first end and an outlet port 938 at a second end. The tubular inlet member 930 may include an external portion that extends upward and away from the top member 960 of the cartridge 920 (e.g. an acute angle) to the inlet port 932 at the first end, and an internal portion that extends within the internal volume 924 to direct urine flow toward the projecting portion 922. In particular, and as shown in FIGS. 23 and 24, the external portion and internal portion of the tubular inlet member 930 may be adjoined and fluidly interconnected in the front portion 923 of the cartridge 920, wherein the internal portion is configured to direct urine flow away from the overflow port 180 (e.g. a top end of an upstanding tubular member 954 defined by bottom member 950) and towards the projecting portion 922. As shown, the internal portion of the inlet member 930 may extend along a top surface 965 of the internal volume 924 of the cartridge 920, as defined by top member 960, with the outlet end 938 of inlet member 930 located at or adjacent to an interface between the front portion 923 and projecting portion 922 of the cartridge 920.

An additional embodiment of a bottom member 850 for use place of bottom member 150 in cartridge 120 is illustrated in FIGS. 25-29. As illustrated, the bottom member 850 may comprise various features as described above in relation to bottom member 150 and corresponding reference numerals are therefore utilized in relation to such features.

As shown, the bottom member 850 may define a bottom surface 856 of an internal volume 824. The bottom surface 856 may extend rearward and downward in front portion 823 of the cartridge 120 to a projecting portion 822 of the cartridge 120. The bottom surface 856 may include a plurality of grooves or raised landings 857 in the front portion 823 so as to facilitate urine flow from the front portion 823 to the projecting portion 822, thereby facilitating urine accumulation and detection in the projecting portion 822.

In the front portion 823 and projecting portion 822 the bottom surface 856 may extend rearward and downward at an angle of G° relative to a reference plane that extends perpendicular to a longitudinal axis CC extending through the discharge port 152 in the projecting portion 822. Bottom surface 856 may be provided so that G°≥11°, and in some embodiments G°≥15°.

As best shown in FIG. 26, the landings and/or grooves 857 may extend rearward along the bottom surface 856 in the front portion 823 toward the projecting portion 822 in a converging manner, e. g. toward a center axis JJ of the bottom surface 856 that extends through the front portion 823 and projecting portion 822. As illustrated, the grooves and/or landings 857 may define a spoke-like pattern centered on a surface region at an interface between the front portion 823 and the projecting portion 822.

As shown in FIGS. 26 and 27, bottom surface 856 may be provided with a raised surface portion 858 extending between the front face 850a and the upstanding tubular member 854 defining the overflow port 180 in the front portion 823, so as to direct urine flow around the upstanding tubular member 854 to the projecting portion 822. As shown in FIG. 27, the raised surface portion 858 may have an inverted V-shaped configuration and may extend along the center axis JJ of the bottom surface 856 of the bottom member 850.

As further illustrated by FIGS. 25-29, the bottom surface 856 defined by the bottom member 850 may be of a sloped, V-shaped configuration. In particular, bottom surface 856 may be provided to extend rearward and downward from the front face 850a of the front portion 823 to the projecting portion 822 at an angle of G°, where G°≥11°, and in some embodiments G°≥15° and bottom surface 856 may be further provided to extend downward from opposing side faces 850b of the front portion 823 toward the center axis JJ of the bottom surface 856 at an angle of H°, where H°≥11°, and in some embodiments H°≥15°. The bottom surface 856 may be provided so that G°≥H°. For example, in one embodiment the bottom surface 856 may be provided so that G°=20° and H°=15°.

It is contemplated that the monitoring device 200 may be supported by a stand (not shown) so that, when the second urine collection device 100 is supportably interconnected to the monitoring device 200, the longitudinal axis CC referenced above is preferably oriented substantially vertical. Further, in contemplated arrangements, the first urine collection device 10 and second urine collection device 100 may be provided so that, upon interconnection therebetween and to monitoring device 200 for second mode operation, the interconnected tubular portion 37 of diverter 30 and tubular inlet member 130 are angled downwardly relative to a horizontal plane, at an angle that is greater than a predetermined acceptable tilt angle, to facilitate gravity urine flow from inlet port 32 in to cartridge 120, and the interconnected tubular outlet members 140a, 140b and Y-member 141 are angled downwardly, relative to a horizontal plane, at an angle that is greater than a predetermined acceptable tilt angle, to facilitate gravity urine flow from the cartridge 120 in to the collection reservoir 20.

Figure 8A:
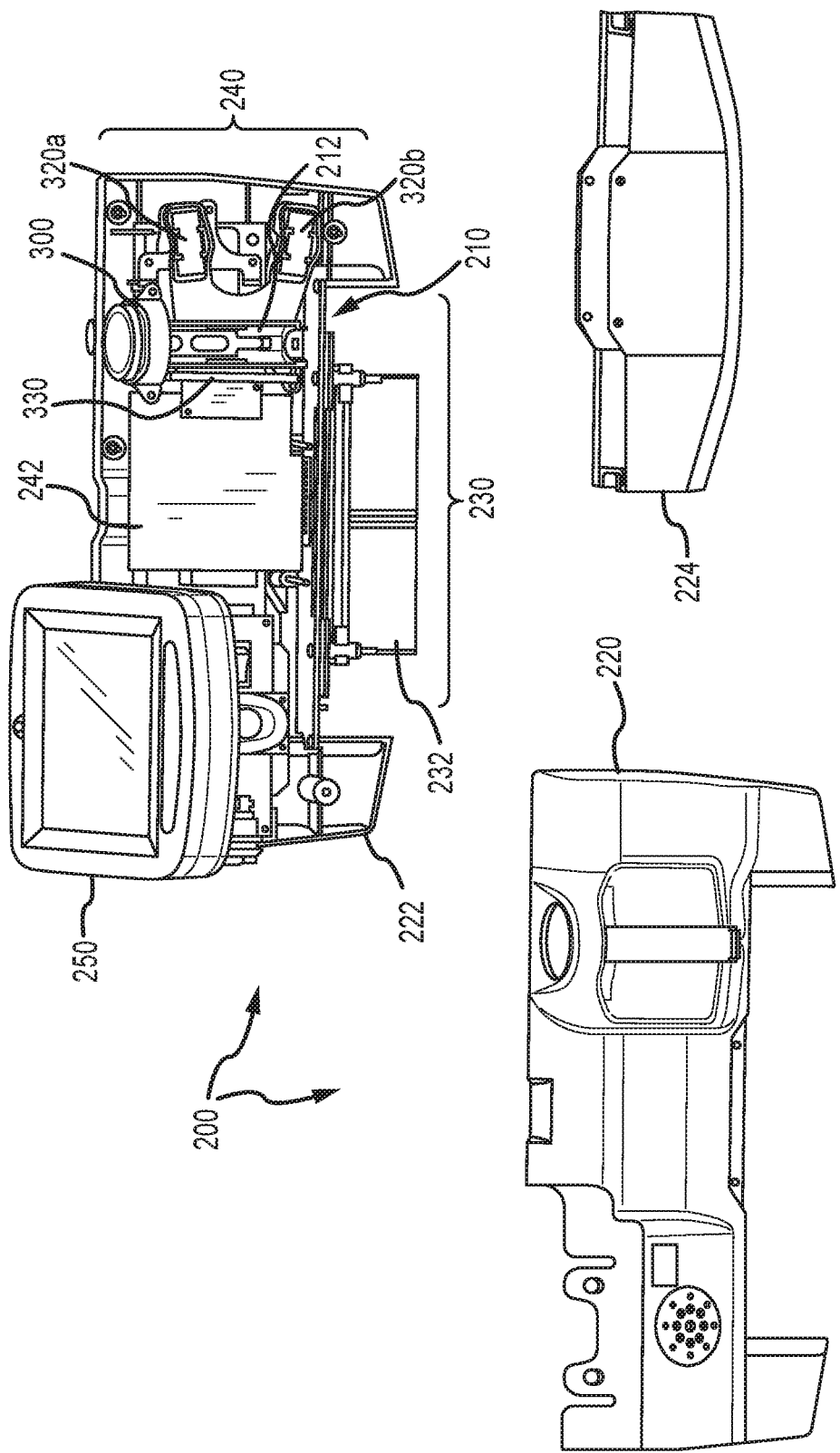
FIG. 8A illustrates housing members and interface components of the monitoring device of the embodiment of FIG. 1, wherein such interface components operatively interface with the second urine collection device of the embodiment of FIG. 1.

Reference is now made to FIG. 8A which illustrates a front housing member 220, a rear housing member 222 and a bottom housing member 224 of monitoring device 200, as well as various componentry housed within an embodiment of the monitoring device 200. In particular, a bottom housing 230 of monitoring device 200 may house power componentry, including for example one or more batteries 232 (e.g. rechargeable batteries). The bottom housing portion 230 may be provided for separate accessibility via removal of the bottom housing member 224 for servicing of the batteries 232. For example, depleted batteries 232 (e.g. having a low charge) can be readily removed (e.g. for recharging at a separate charging station) and replaced by charged batteries 232. To facilitate handling, a plurality of batteries 232 may be physically interconnected in a battery pack module. An upper housing portion 240 may house various components that interface with the second urine collection device 100 at the interface portion 210 of the monitoring device 200, as well as control logic (e.g. one or more microprocessors), memory and additional components operatively interconnected in one or more printed circuit board assemblies (PCBA) (e.g. a measurement PCBA 242) for communicating and processing sensor, input, output control and additional signals, including for example input and output signals communicated via user interface 250, and for providing power signals.

Figure 8B:
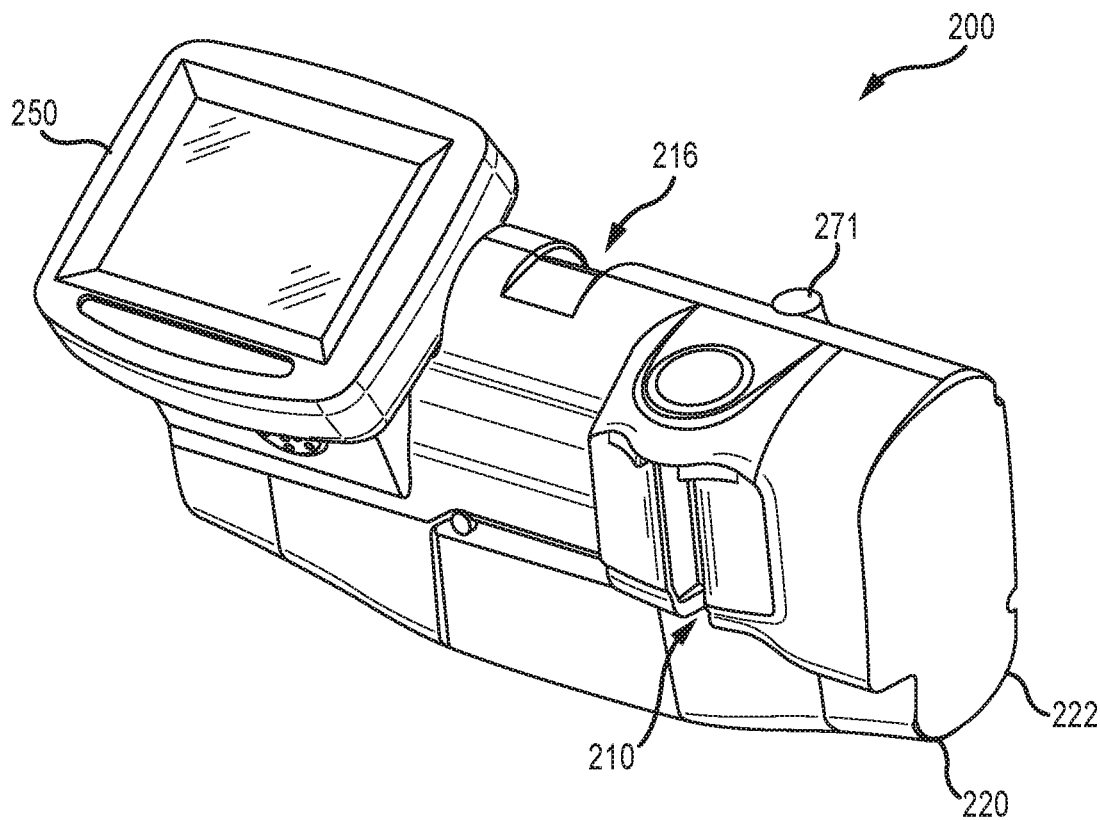
FIG. 8B is a perspective view of the monitoring device of the embodiment of FIG. 1.
Figure 8C:
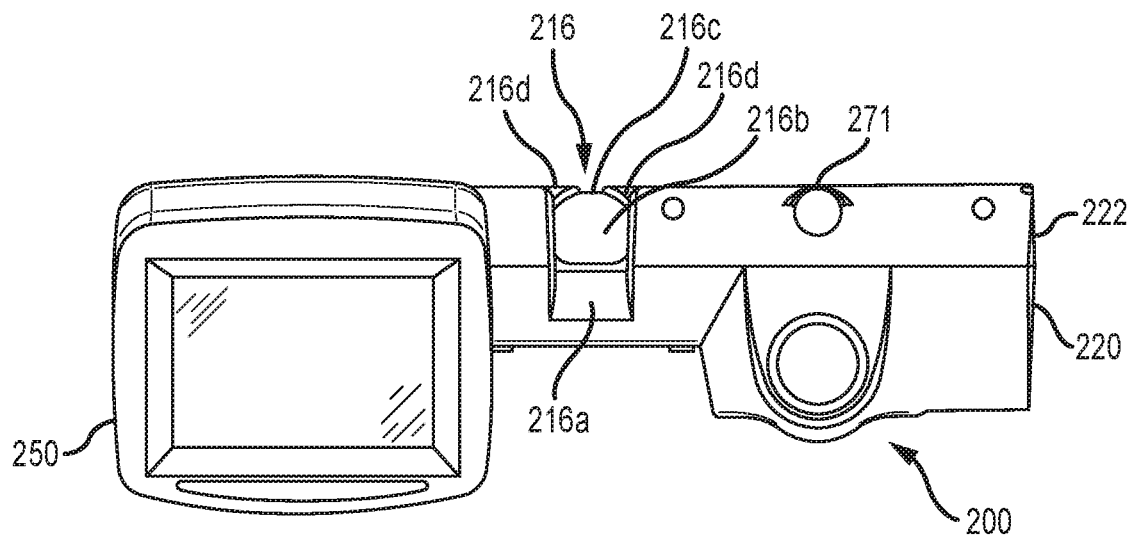
FIG. 8C is a top view of the monitoring device of the embodiment of FIG. 1.

As shown in FIGS. 8B and 8C, and noted above, the monitoring device 200 may include a surface region 216 configured to receive the first hangar 82 of the hangar member 80 of the first urine collection device 10 shown in FIGS. 2 and 3, including in particular, when the first urine collection device 10 and second urine collection device 100 are interconnected and the second urine collection device 100 is interconnected to monitoring device 200 for urine output monitoring. More particularly, the surface region 216 may include an upwardly-angled front face 216a, and an adjoining, downwardly-angled rear face 216b that extends to a slot 216c. The front face 216a and rear face 216b combinatively define a length, or thickness, that is less than width of the U-shaped opening of the first hangar 84. The slot 216c may be sized to receive and restrict side-to-side movement of first hangar 82 when hangar member 80 is employed to support, or hang, the first urine collection device 10 on the monitoring device 200. As illustrated in FIG. 8c, angled guide members 216d may be provided on each side of slot 216c to define a truncated, V-shaped configuration for receiving and guiding first hangar 82 in to the slot 216c. Further, such V-shaped configuration may facilitate interconnection of the cartridge 120 of the second urine collection device 100 to the monitoring device 200. For example, a user may initially position the first hangar 82 to supportably hang on the second urine collection device 100, then the user may swing the cartridge 120 into an interconnected position at the interface portion 210 of the monitoring device 200.

With further reference to FIGS. 8B and 8C, and as noted above, the monitoring device 200 may include a bubble level 271. As illustrated, the bubble level 271 may be disposed on a top surface of the monitoring device 200 to facilitate ready observation by a user.

Returning now to FIG. 8A, interface components that may be located at the interface portion 210 may include a support member 300 that may be supportably and fixedly interconnected to the rear housing member 222 and/or front housing member 220. The support member 330 may be provided to support and locate light sources 320a, 320b (e.g. laser diodes) on a first side of the recessed portion 212, and to engage and thereby locate a light detector array 330 (e.g. a charge coupled device array) on an opposing, second side of the recessed portion 212, wherein such components may be utilized for detecting a volume and/or level of urine accumulated within the second urine collection device 100, as described above.

Figure 9:
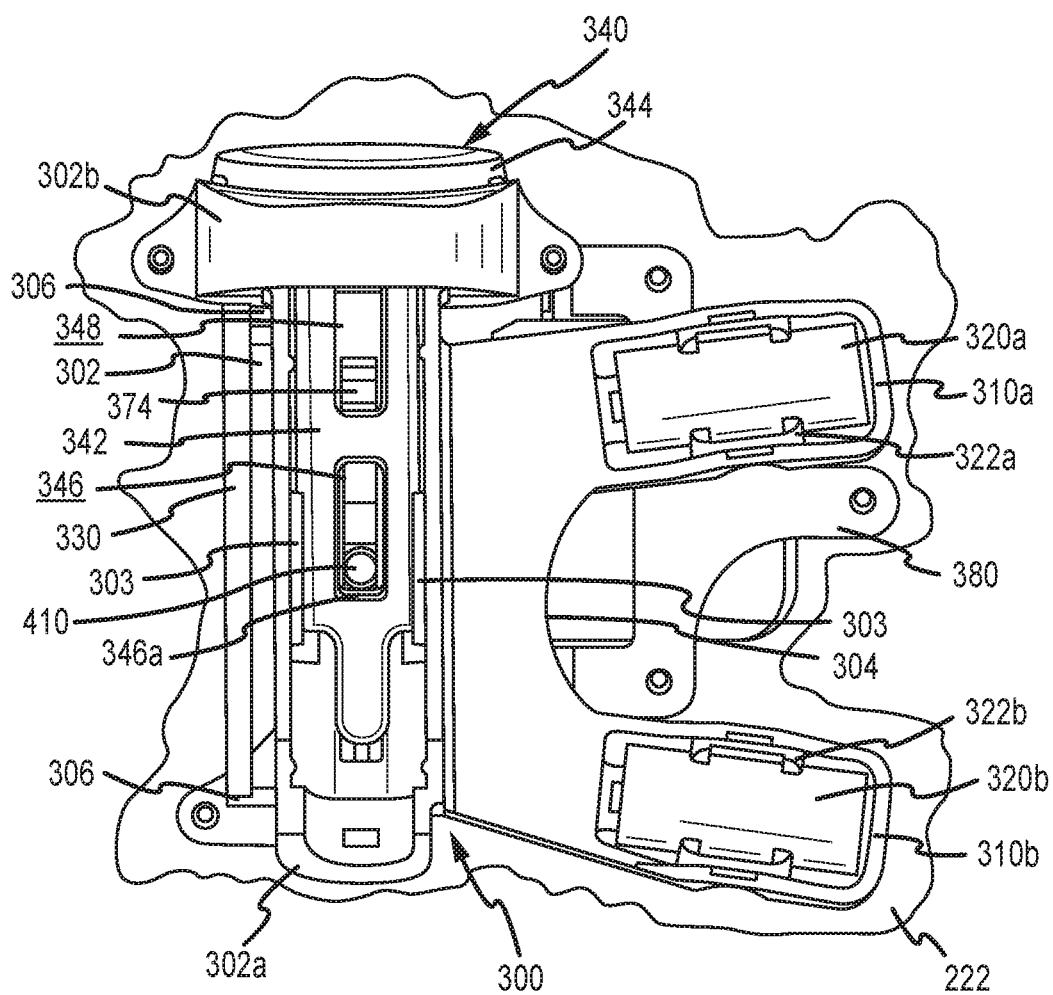
FIG. 9 is a front cutaway illustration of a support member and additional interface component of the monitoring device of the embodiment of FIG. 1, wherein such interface components operatively interface with the second urine collection device of the embodiment of FIG. 1.

For example, and as shown in the cutaway illustration of FIG. 9, the support member 300 may include an upright frame portion 302 defining a recess at a front face of the support member 300 for receiving the projecting portion 122 of the cartridge 120 therewithin, and a laterally projecting portion 304 to support and locate light sources 320a, 320b on a first side of the recessed portion 212. The support member may also include one or more projecting members 306 to engage and thereby locate a light detector array 330 (e.g. a CCD array) on an opposing, second side of the recessed portion 212.

Figure 10:
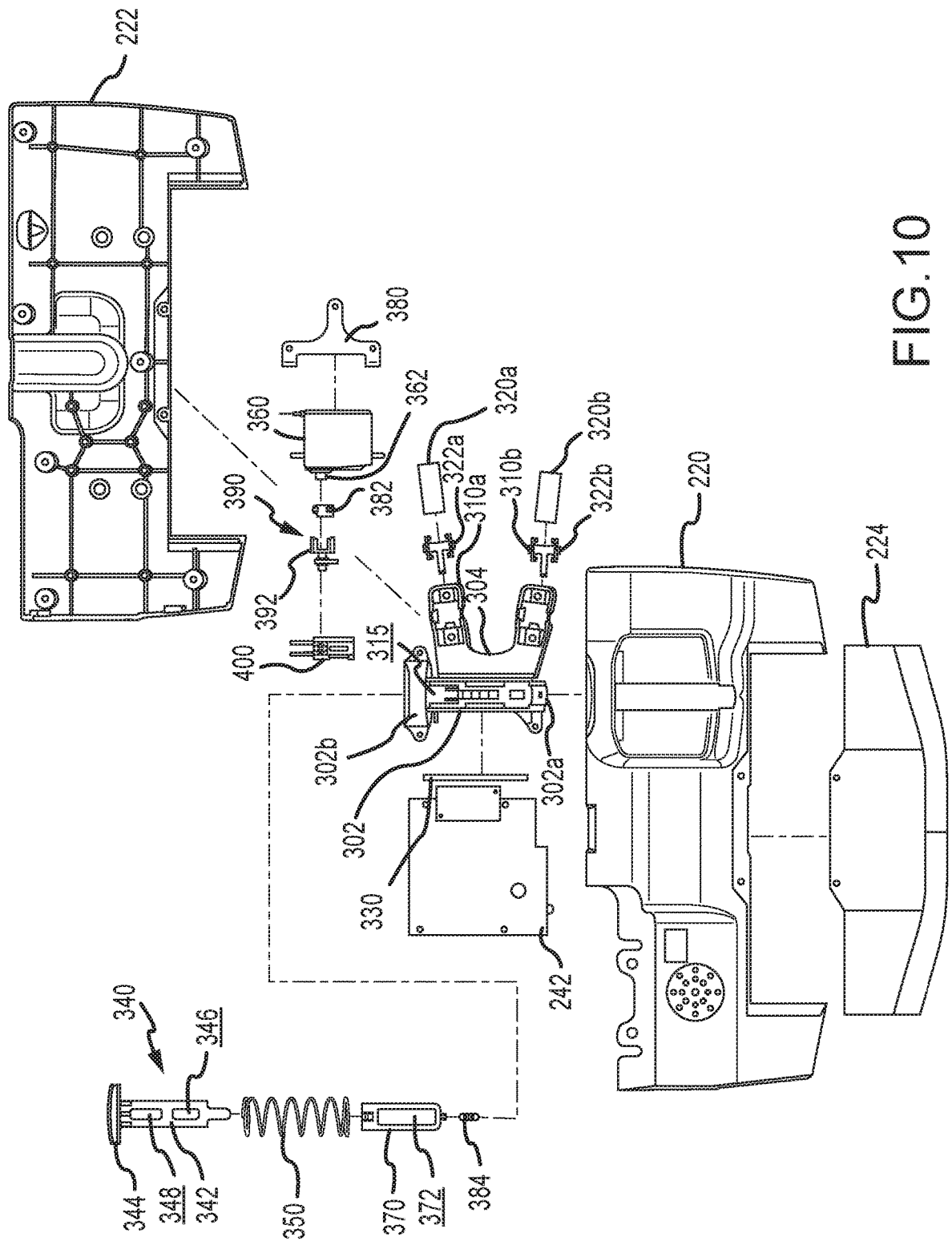
FIG. 10 is a front exploded view of interface components of the monitoring device of the urine collection system embodiment of FIG. 1, wherein such interface components operatively interface with the second urine collection device of the embodiment of FIG. 1.

As shown in FIGS. 9 and 10, the light sources 320a, 320b may be supportably positioned in corresponding clips 322a, 322b which may be supportably interconnected to corresponding frame regions 310a, 310b of the laterally projecting portion 304 of support member 300. Similarly, light detection array 330 may be engaged and located by projecting members 306 (e.g. posts) of support member 300. Such an approach facilitates interconnection of the noted components to the support member 300 prior to assembly in to the rear housing member 222 and/or front housing member 220.

In some implementations, clips 322a, 322b and corresponding frame regions 310a, 310b may be configured to allow for rotative and set positioning of light sources 320a, 320b about corresponding upright axes to facilitate desired positioning relative to the light detection array 330. In particular, clips 322a, 322b may be provided with outwardly-projecting side hinges that may be received by slots of upstanding hubs provided by the frame regions 310a, 310b. Each of the clips 322a, 322b may be of a saddle-like configuration, wherein opposing cantle members of the clips 322a, 322b may be configured to receive the light sources 320a, 320b for snap-fit engagement therebetween. The clips 322a, 322b, together with light sources 320a, 320b supported thereby, respectively, may be rotated into a desired orientation relative to the light detector array 330. When so located, set screws may be advanced through two spaced and threaded openings provided in each of the frame regions 310a, 310b to engage backside portions of the light sources 320a, 320b and/or a projecting member of the clips 322a, 322b. As may be appreciated, the described arrangement allows for the light detector array 330 to be supportably disposed on support member 300, and for the light sources 320a, 320b to be supportably disposed on the support member 330 and rotatably positioned and set in a desired orientation relative to light detection array 330, prior to positioning of such interconnected components into the rear housing member 222 and/or front housing member 222.

Additional interface features and componentry located at the interface portion 210 of monitoring device 200 may provide for mechanical support and interconnection/disconnection of the second urine collection device 100 to/from the monitoring device 200. In that regard, the support member 300 may be provided to engage and at least partially support the cartridge 120 of the second urine collection device 100. For example, and as shown in FIGS. 9 and 11, the upright frame portion 302 may define one or more shelf-like support surfaces 302a at the bottom of the recess for supportably engaging a portion of a bottom surface of the projecting portion 122 of cartridge 120.

Figure 11:
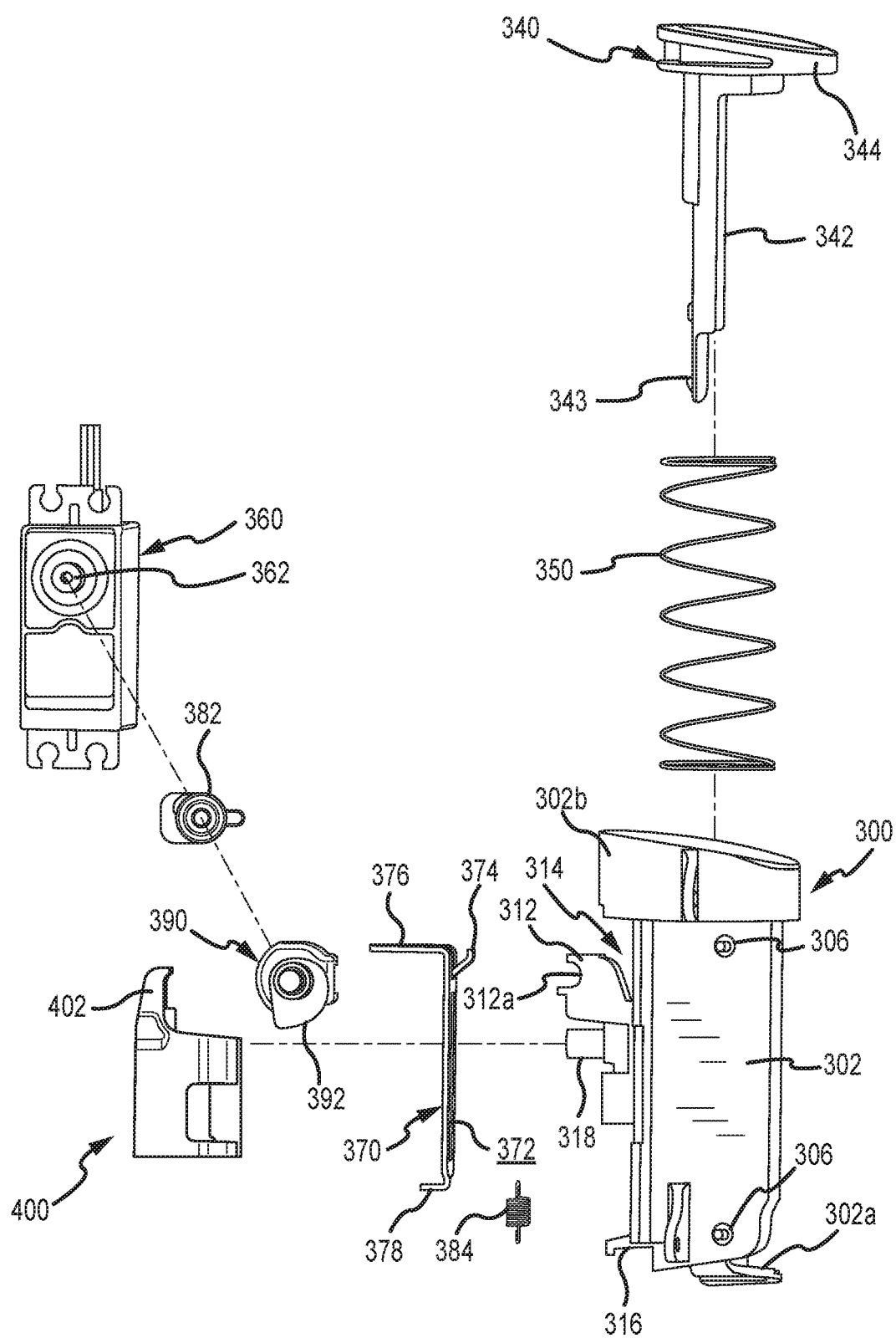
FIG. 11 is a side exploded view of interface components of the monitoring device of the urine collection system embodiment of FIG. 1, wherein such interface components operatively interface with the second urine collection device of the embodiment of FIG. 1.

Further, as shown in FIGS. 9-11, the monitoring device 200 may include a latch member 340 for latching engagement with the downward-oriented hook member 128 provided on the back side of the projecting portion 122 of cartridge 120. The latch member 340 may be supported and located by the support member 300. For example, the latch member 340 may include an elongated portion 342 that may be slidably disposed along the upright frame portion 302 of support member 300 at the back of the recess, and an enlarged head portion 344 that may be supported at a ring-shaped, top end 302b of the upright frame portion 302. The upright frame portion 302 may include flanges 303 to define slide channels for opposing side edges of the elongated portion 342 of latch member 340.

With reference to FIGS. 10 and 11, a latch spring 350 may be located about the elongated portion 342 of the latch member 340 and captured between the enlarged head portion 344 and the top end 302b of the upright frame portion 302. As will be further described, the latch spring 350 may be provided to bias the latch member 340 upward, wherein a bottom slot 346 of the latch member 340 may be provided to receive the hook member 128 of cartridge 120 therethrough for latching engagement.

In that regard, and with further reference to FIG. 9, the monitoring device 200 may include a limit switch 410 disposed in aligned relation with a portion of the bottom slot 346 of the latch member 340. In turn, when the hook member 128 of cartridge 120 is received through the bottom slot 346 for latched engagement and interconnection of the second urine collection device 100 with monitoring device 200, the limit switch 410 is engaged by the hook member 128 (e.g. depressed against a spring bias) so as to close or activate the limit switch 410, wherein the interconnected presence of the second urine collection device 100 is automatically detected by monitoring device 200. In turn, various functionalities of monitoring device 200 are enabled. In some implementations, upon activation of limit switch 410 and authentication of second urine collection device 100 (e.g. via automatic reading of unique identification indicia from a machine-readable component provided thereupon) monitoring device 200 may be automatically enabled to perform urine volume and/or level monitoring operations as described herein.

FIGS. 10 and 11 further illustrate that monitoring device 200 may comprise components for automated control of the valve member 172 of the second urine collection device 100 via mechanical interface with the arm 178 of the top end member 176 of the valve assembly 170 described above. In particular, and as described above, the monitoring device 210 may include an actuator 360 (e.g. a servo motor) to provide a mechanical output that is communicated to an actuation member 370 so as to lift the valve member 172 of the second urine collection device 100 to open the discharge port 152. The actuator 360 may be supportably interconnected to the rear housing member 222 and/or front housing member 220 rearward of the support member 300. For example, as illustrated in FIGS. 9 and 10, a bracket member 380 may be utilized to supportably and fixedly interconnect actuator 360 to the rear housing member 222.

The actuator 360 (e.g. a servo motor) may include an output shaft 362 that may be reciprocally rotated in a first direction and an opposite second direction (e.g. counter-clockwise and clockwise). A cam member 390 may be interconnected to the output shaft 362 of actuator 360 for co-driven rotation therewith. Optionally, the cam member 390 may be supported separately from the actuator 360. In turn, an adapter 382 may be interconnected to the output shaft 362 and disposed to operatively interface with the cam member 390. In such arrangements, the cam member 390 may be supported by support member 300.

The cam member 390 may include a peripheral cam surface 392 having a spiral configuration. The actuator 360, the cam member 390, and the actuation member 370 may be located so that, upon driven counter-clockwise rotation and clockwise rotation of output shaft 362, the cam member 390 may co-rotate so that the cam surface 392 thereof may engage the actuation member 370 so as to raise and lower the actuation member 370, respectively. In that regard, the support member 300 may be further provided to locate the actuation member 370 for operative interface with both the cam member 390 and with the arm 178 of the top member 176 of the valve assembly 170 of the second urine collection device 100 when the second urine collection device 100 is interconnected to the monitoring device 200.

Figure 12:
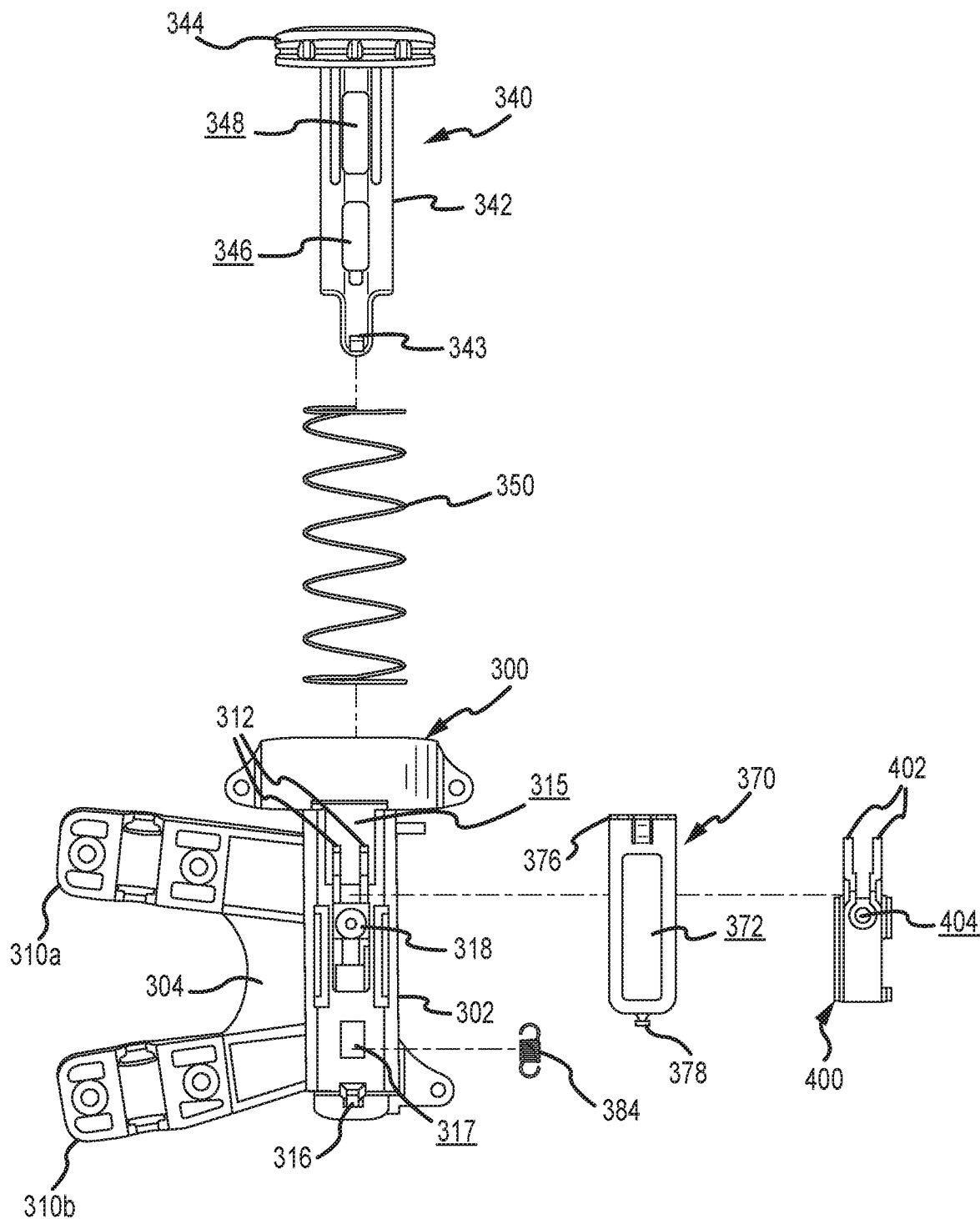
FIG. 12 is a rear exploded view of interface components of the monitoring device of the urine collection system embodiment of FIG. 1, wherein such interface components operatively interface with the second urine collection device of the embodiment of FIG. 1.

To further describe such functionality, reference is now made to FIGS. 11 and 12. To locate actuation member 370 and support cam member 390, the support member 300 may include a pair of rearwardly-projecting support arms 312. The support arms 312 may define a notch region 314 between the support arms 312 and upright frame portion 302 for receiving and thereby locating the actuation member 370. In the later regard, the actuation member 370 may include an aperture 372 for receiving the support arms 312 therethrough, wherein a surface of the actuation member 370 located at the top of the aperture 372 may supportably engage top surfaces of the support arms 312 in the notch region 314.

As shown in FIG. 11, actuation member 370 may include a forwardly-projecting first lift arm 374, and as shown in FIG. 12 the support member 300 may include a top window 315 through the upright frame portion 302 for receiving the first lift arm 374 therethrough when the actuation member 370 is supportably located over support arms 312. Relatedly, and as shown in FIGS. 9, 10 and 12, the latch member 340 may be provided with an upper slot 348 for receiving the first lift arm 374 of actuation member 370 therethrough when the actuation member 370 is supportably located over support arms 312.

Returning now to FIGS. 11 and 12, actuation member 370 may further comprise a rearwardly-projecting, second lift arm 376 disposed for engagement with the cam surface 392 of cam member 390 so as to translate the rotational output of actuator 360 to vertical displacement of the actuation member 370. For example, in relation to the position of the cam member 390 and the position of the actuation member 370 shown in FIG. 11, counter-clockwise rotation of cam member 390 (e.g. a 180° rotation) will lift the actuation member 370 from a home position to a raised position via contact interface between second lift arm 376 and cam surface 392, and subsequent clockwise rotation of cam member 390 (e.g. a 180° rotation) will lower the actuation member 370 from the raised position to the home position.

In the later regard, to facilitate return positioning of actuation member 370 from the raised position to the lower, home position, monitoring device 200 may include a return spring 384 interconnected between a rearwardly projecting anchor arm 378 of support member 300 and a rearwardly projecting, bottom arm 316 of actuation member 370. Such components may be provided so that the return spring 384 provides a biasing force to facilitate the return of actuation member 370 from the raised position to the lower, home position (e.g. in conjunction with clockwise rotation of cam member 390.)

With further reference to FIGS. 11 and 12, monitoring device 200 may be provided with features to reduce side-loading forces that act upon actuator 360 via output shaft 362. In particular, the support arms 312 of support member 300 may include arcuate recesses 312a sized for positioning under and about shaft portions of cam member 390 that are located on opposing sides of a projection portion that extends away from the shaft portions and defines the peripheral, spiral-configured cam surface 392. The arcuate recesses 312a of support arms 312 may be provided to absorb both vertical loads and horizontal loads in a first direction.

Additionally, in order to absorb horizontal loads in a second direction, opposite to the first direction, monitoring device 200 may include an auxiliary support member 400 that may be supportably interconnected to the support member 300. For example, support member 300 may include a tubular, standoff 318 projecting rearwardly and through which a connection member (e.g. a threaded carrier screw or the like) may be located, wherein the connection member may further extend into a hole 404 (e.g. a threaded opening of auxiliary support member 400). As shown in FIGS. 11 and 12, to provide for horizontal load absorption in the second direction, the auxiliary support member 400 may include one or a pair of upstanding arms 402.

As noted above, latch member 340 may be provided for latching engagement with the downward-oriented, hook member 128 of cartridge 120 of the second urine collection device 400. In that regard, a catch member 343 may project rearwardly at a bottom end of the elongated portion 342 of the latch member 340 (See FIG. 11) for positioning within a bottom window 317 located at a bottom end of the upright frame portion 302 of the support member 300 (See FIG. 12). When the latch member 340 is so located, the latch spring 350 acts to bias the latch member 340 upward.

As shown in FIG. 9, a bottom slot 346 may be provided through the elongated portion 342 of the latch member 340 to receive the hook member 128 of cartridge 120 in latched engagement. In that regard, a surface of latch member 340 at the bottom of slot 346 may define an angled ramp 346a. Further, and described above in relation to FIG. 6, the hook member 128 may include a complimentary angled ramp 128a to cooperate with the angled ramp 346a of latch member 340, wherein upon advancement of the hook member 128 the angled ramp 128a thereof may engage the angled ramp 346a at the bottom of slot 346 of the latch member 340 so as to displace the latch member 340 downward against the spring bias of latch spring 350 until the angled ramp 128a of hook member 128 is advanced through the slot 346, at which point the latch member 340 may spring back upward so as to latch within the downward-facing notch 128b of the downward-oriented hook member 128.

Figure 13:
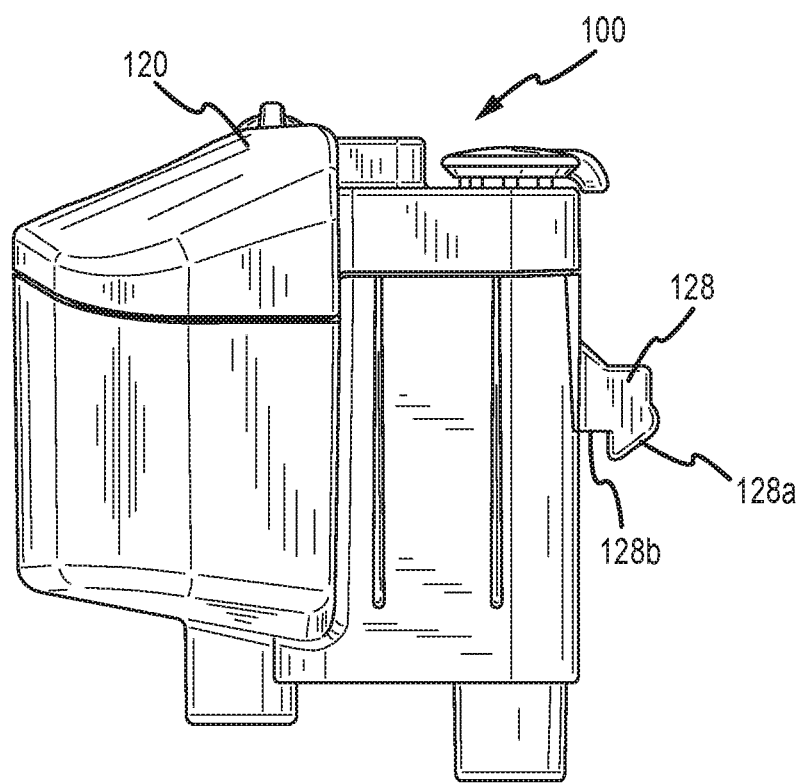
FIG. 13 is a side view of the second urine collection device of the embodiment of FIG. 1.
Figure 14:
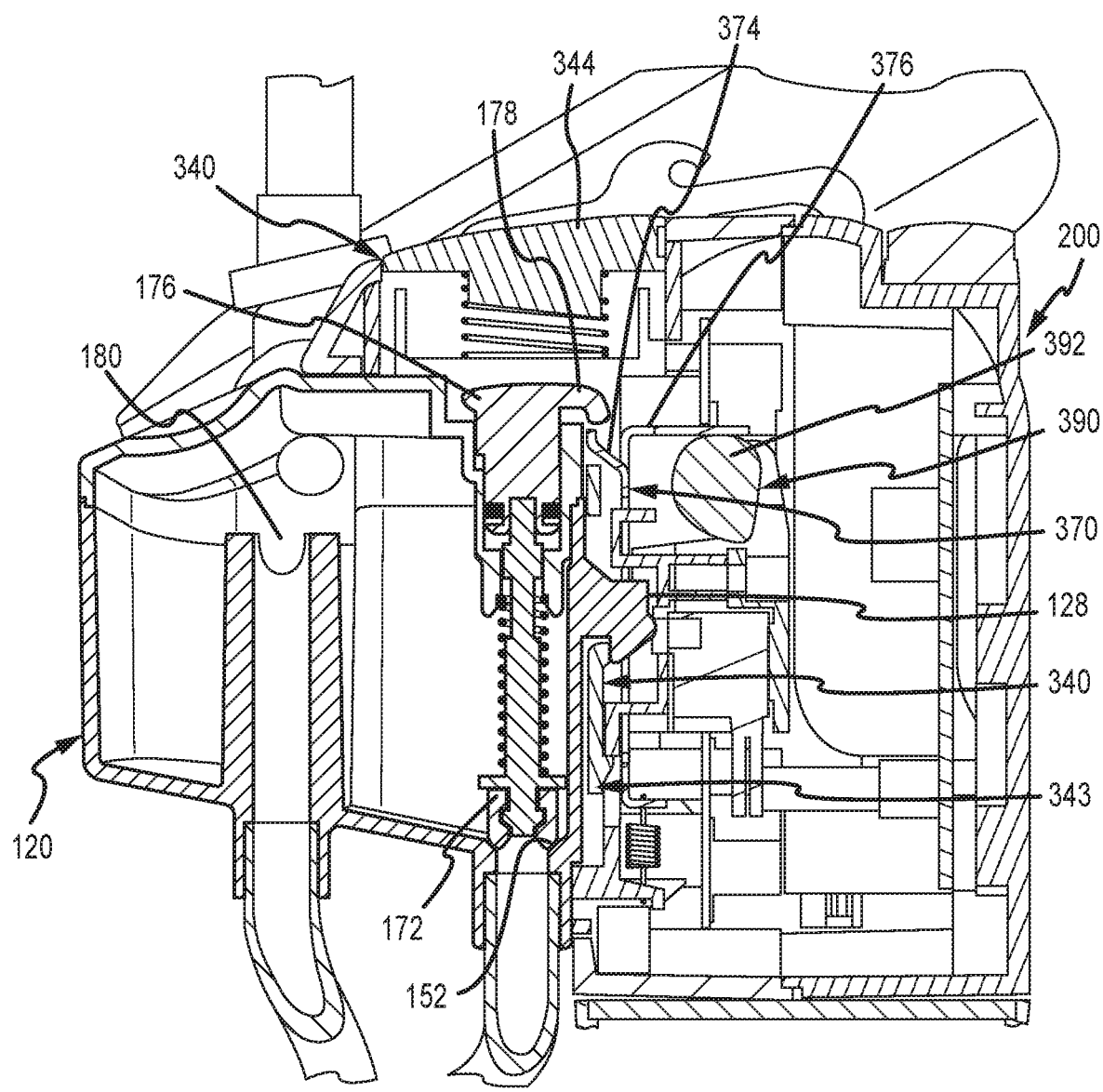
FIG. 14 is a side cross sectional view of the second urine collection device interconnected to the monitoring device of the urine collection system of the embodiment of FIG. 1.

To facilitate a further understanding of the latching interface, reference is now made to FIGS. 13 and 14. FIG. 13 illustrates a side view of the cartridge 120 of the second urine collection device 100. FIG. 14 illustrates a cross sectional view of the cartridge 120 interconnected to the monitoring device 200. As shown in FIG. 14, the downward-oriented hook member 128 of the cartridge 120 is in latched engagement with the latch member 340. As further shown, the forwardly-projecting first lift arm 374 of actuation member 370 is disposed immediately under and adjacent to the arm 178 of the top member 176 of the valve assembly 170 of the second urine collection device 100, and the top end member 176 is not manually accessible by a user. Further, the rearwardly-projecting, second lift arm 376 of the actuation member 370 is disposed immediately over the cam surface 392 of cam member 390. In such position, upon rotation of cam member 390 the cam surface 392 may function to lift the second lift arm 376 and the first lift arm 374 so as to engage the arm 178 of the top end member 176 and thereby lift valve 172 upward to open discharge port 152. In turn, upon counter rotation of the cam member 390, the valve 172 may be lowered vertically to close the discharge port 152.

As may be appreciated, the latch member 340 may be engaged by a user for manual disconnection of the second urine collection device 100 from monitoring device 200. In particular, a user may push downward on the enlarged head portion 344, against the spring force of latch spring 350, so as to position the top slot 348 of latch member 340 for retracted, clear passage of the hook member 128 of cartridge 120 therethrough. For example, a user may push down on the enlarged head portion 344 with one hand, while grasping and retracting cartridge 120 laterally away from the monitoring device 200 with the other hand.

Figure 15:
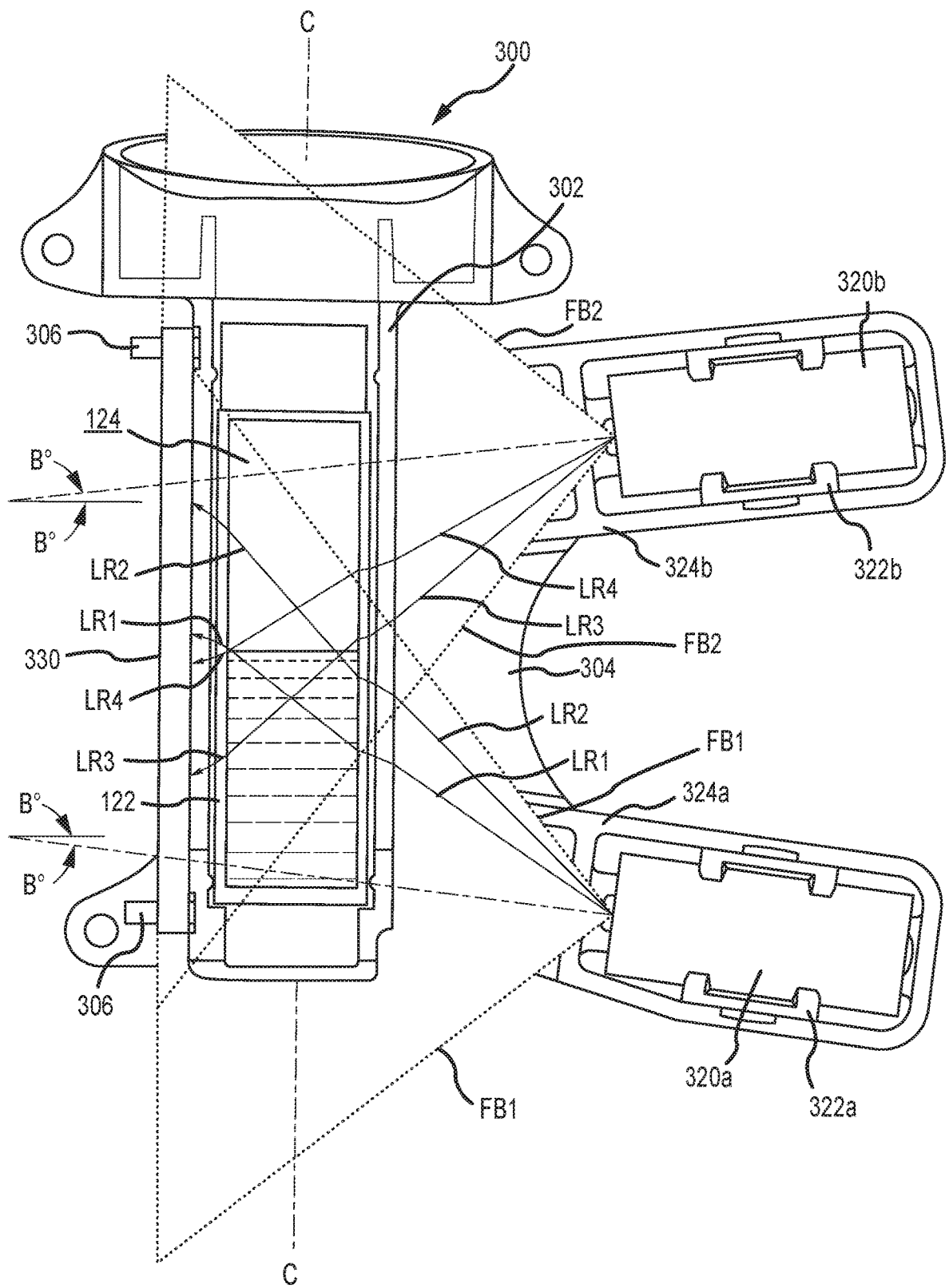
FIG. 15 is a front view of a support member, light sources and a light detector array of the monitoring device of the embodiment of FIG. 1, in operative association with a projecting portion of a cartridge of the second urine collection device of the embodiment of FIG. 1.

Reference is now made to FIG. 15, which illustrates a cross-sectional view of the projecting portion 122 of the cartridge 120 of second urine collection device 100, as located within the recess defined by the upright frame portion 302 at the front face of the support member 300 of monitoring device 200. A volume of collected urine is shown within the projecting portion 122 of the internal volume 124 of the cartridge 120. FIG. 15 also illustrates light sources 320a, 320b supportably positioned in clips 322a, 322b which are supportably interconnected to corresponding frame regions 310a, 310b, respectively, of the laterally projecting portion 304 of support member 300 on one side of the upright frame portion 302 and projecting portion 122. Further, light detector array 330 is shown supportably located on posts 306 of the support member 300 on a second side of the upright frame portion 302 and projecting portion 122.

In the illustrated embodiment, light sources 320a, 320b (e.g. laser diodes) may be provided to emit corresponding first and second fan beam light signals (FB1, FB2), wherein the light sources 320a, 320b may be located at different heights (e.g. vertically offset) and the fan beam light signals FB1, FB2 may be provided for detection along a height of the light detector array 330 that may at least encompass and may be greater than a predetermined height of the internal volume 124 of projecting portion 122 within which urine may accumulate during use. For example, the height may be greater than a height of the overflow port 180 of the cartridge 120, e.g. relative to a reference plane that extends perpendicular to the longitudinal axis CC, at or immediately above the discharge port 152.

In contemplated arrangements, the light sources 320a, 320b may be laser diodes having corresponding center wavelengths within a desired range of sensitivity of the light detection array 330. For example, in some embodiments laser diodes may be employed that have center wavelengths within a wavelength range of 620 nm to 750 nm.

As further illustrated in FIG. 15, bottom light source 320a may be angled upward and top light source 320b may be angled downward, e.g. relative to longitudinal axis CC. More particularly, light sources 320a, 320b may be provided so that a center axis of the first fan beam light signal FB1 and/or second fan beam light signal, FB2 is oriented at an acute angle of at least B° relative to reference planes that extend perpendicular to the longitudinal axis CC. In some implementations, the light sources 320a, 320b may be provided so that B° is greater than a predetermined allowed tilt angle. For example, where a predetermined acceptable tilt angle is 10°, B° may be established to be greater than 10° (e.g. 11°). The light sources 320a, 320b may angled at acute angles which are the same or different.

As noted above, the light detector array 330 may be comprise a charge coupled device. In contemplated arrangements, a charge coupled device comprising a pixel array of M×N in width and height may be employed, wherein M may be 1 or more and N may be greater than at least 600. For example, in one implementation, a pixel array of 1×768 pixels may be employed. As may be appreciated, one or a plurality of adjacent pixels may define different ones of a plurality of pixel locations along the height of the light detection array 330. In that regard, when the projecting portion 122 is located in the recessed portion 212 of monitoring device 200, each of the pixel locations may be disposed in known or determinable spatial relation to and along the height of the projecting portion 122.

The light detector array 330 may be operable to provide light detection output signals indicative of magnitudes of light received at each of a plurality of different pixel locations along the height of the light detection array 330. In turn, such output signals may be utilized by at least one processor to determine a surface position of urine collected within the cartridge 120 of the second urine collection device 100.

In one approach, it has been recognized that, for the portion of a fan beam light signal FB1 or FB2 that passes through the surface of collected urine, the magnitude of light received at the detector array 330 is less than the magnitude of light detected at detector 330 for one or more adjacent portions of the fan light beam signal FB1 or FB2. For example, in relation to the first fan beam light signal FB1 of light source 320a shown in FIG. 15, the portion of the first fan beam light signal FB1 between light rays LR1 and LR2 will yield a lower detected magnitude at light detector 330 than the portions of the first fan beam light signal FB1 below array light ray LR1 and above light ray LR2. Similarly, in relation to the second fan beam light signal FB2 of light source 320b shown in FIG. 15, the portion of the second fan beam light signal FB2 between light rays LR3 and LR4 will yield a lower detected magnitude at light detector 330 than the portions of the second fan beam light signal FB2 below light ray LR3 and above light ray LR4.

In turn, processing of the output signals of the light detector array 330 by one or more processor(s) of the monitoring device 200 may entail a comparison of values indicative of magnitudes of detected light at each of a plurality of pixels along at least a portion of the height of the light detector array 330 to one or more predetermined reference value(s) to identify one or a plurality of pixel locations at which the detected magnitude is less than the predetermined reference value(s). The identified one or plurality of pixel locations may be utilized by the processor(s) to determine the location or level of the surface of collected urine and/or the volume of collected urine.

Such determination may be made based upon predetermined correlations between each of a first portion, or continuum, of the plurality of pixel locations of the light detector array 330 and a spatial height within the internal volume 124 of the projecting portion 122 for the first fan beam light signal FB1, and/or predetermined correlations between each of a second portion, or continuum, of the plurality of pixel locations of the light detector array and a spatial height within the internal volume 124 of the projecting portion 122 for the second fan beam light signal FB2. In one approach, each pixel location along the height of the light detector array 330 may have a corresponding predetermined volume and/or level value associated therewith and stored by the monitoring device. In turn, for an identified pixel location(s), the corresponding predetermined volume and/or level value(s) may be utilized to establish the determined volume and/or level of collected urine.

As shown in FIG. 15, the predetermined correlations may account for light refraction at the various interfaces along the light propagation continuum of fan beam light signals FB1, FB2. By way of example, and as shown in FIG. 15, light rays LR1, LR2, LR3 and LR4 are each refracted at the various interfaces, and such refraction may be accounted for by the predetermined correlations.

Similarly, predetermined correlations may also be established to account for tilting of the monitoring device 200 within a predetermined acceptable tilt angle. In that regard, the processors(s) of monitoring device 200 may be operable to utilize a tilt sensor output signal to obtain a tilt angle measure that may be utilized to account for the tilting effect in collected urine volume determinations as otherwise described herein.

Figure 32A:
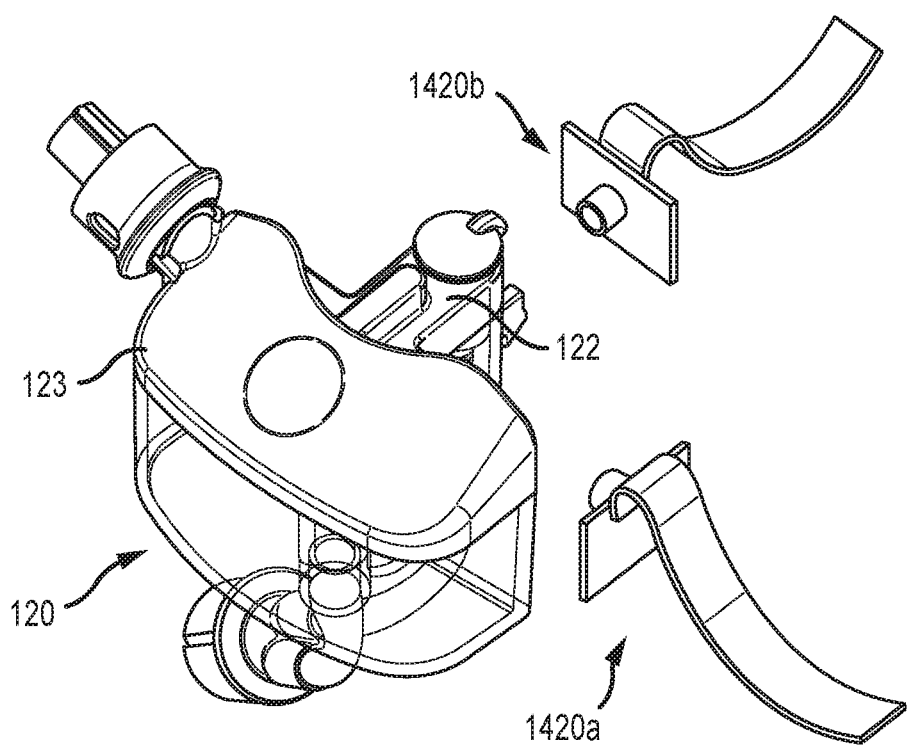
FIG. 32A is a perspective view of the second urine collection device of the embodiment shown in FIG. 1 positioned relative to first and second imaging devices of another embodiment of a monitoring device.
Figure 32B:
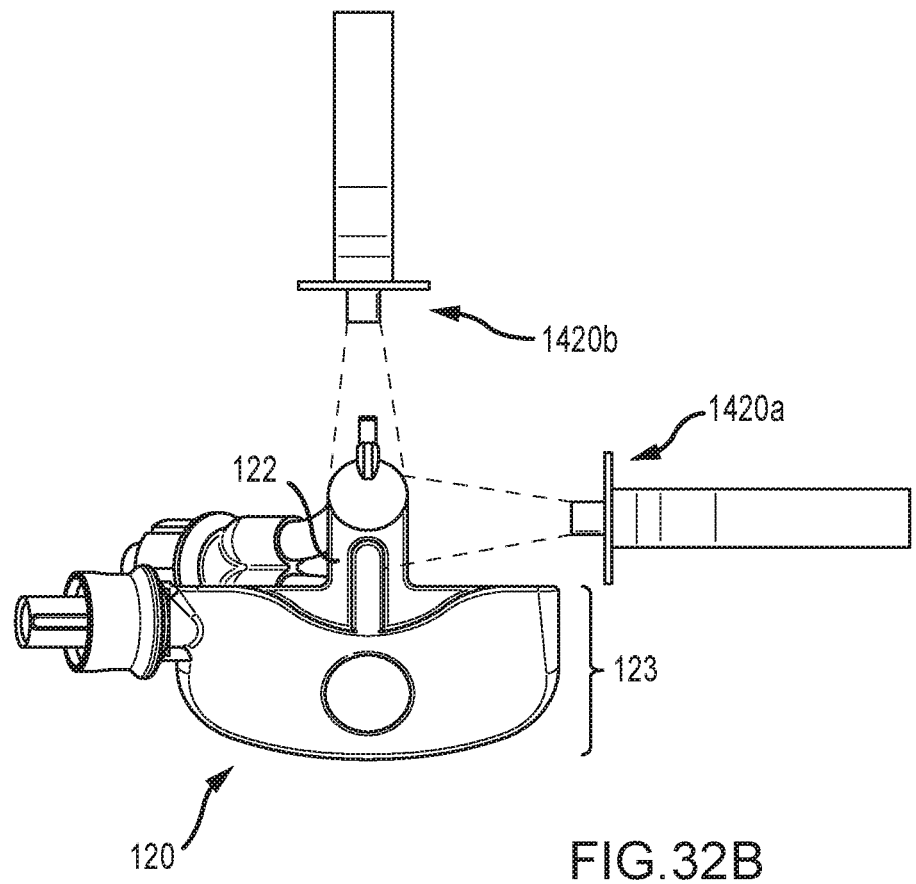
FIG. 32B is a top view of the second urine collection device of the embodiment shown in FIG. 1 as positioned relative to the first and second imaging devices of FIG. 32A.

Reference is now made to FIGS. 32A and 32B, which illustrate the cartridge 120 of the second urine collection device 100 positioned relative to a first imaging device 1420a and a second imaging device 1420b comprising a modified embodiment of the monitoring device 200 otherwise described herein. In the modified monitoring device the light sources 320a, 320b and light detector array 330 may be replaced by the first imaging device 1420a and second imaging device 1420b, and the processor(s) comprising the monitoring device 200 may be operable to process digital image data output from the first imaging device 1420a and second imaging device 1420b to provide accumulated urine volume and/or level determinations, and to provide control signals for operation of the actuator 360 to affect automated discharge and accumulation of urine, as described herein.

The first imaging device 1420a and second imaging device 1420b may be disposed on a first side and on a back side of the recessed portion 212 of the monitoring device 200 described above (e.g. orthogonally positioned as illustrated), respectively. As shown, the first imaging device 1420a may have a corresponding imaging field that encompasses at least a portion of a side wall of the projecting portion 122 of the cartridge 120, wherein the first imaging device 1420a may provide side view digital image data of the projecting portion 122 as urine is accumulated in the cartridge 120. Further, the second imaging device 1420b may have a corresponding imaging field that encompasses at least a portion of a back wall of the projecting portion 122 of the cartridge 120, wherein the second imaging device 1420b may provide back view digital image data of the projecting portion 122 as urine is accumulated within the cartridge 120. The digital imaging data provided by each of the first and second imaging devices 1420a, 1420b may comprise a series of digital image data frames that are outputted on a continuous basis (e.g. a video data stream) or predetermined periodic basis during operational use of the monitoring device 200.

The digital image data output by each of the first and second imaging devices 1420a, 1420b may be processed to determine a location of the surface of accumulated urine within cartridge 120 relative to a predetermined reference datum (e.g. a level and an angle of the surface relative to the reference datum). In turn, corresponding first and second location indicator values may be generated and utilized by the processor(s) to determine a volume and/or level of urine collected, wherein such volume determination may be outputted and stored by the monitoring device 200 as otherwise described. Further, based upon a comparison of the determined volume and/or level and one or more predetermined values, the processor(s) may provide control signals to actuator 360 affect the automated discharge and accumulation of urine from the second urine collection device 100, as otherwise described herein.

Figure 16:
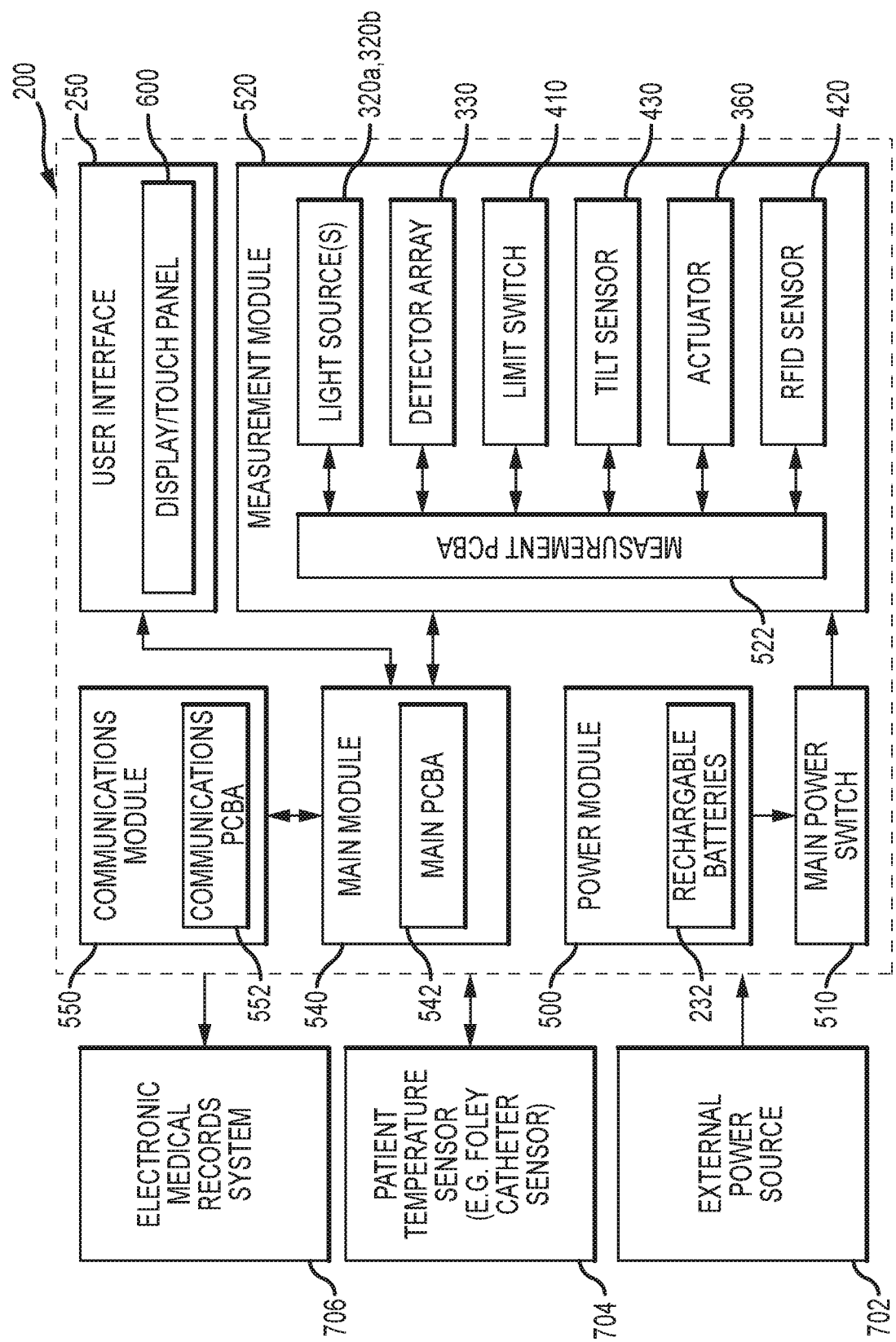
FIG. 16 schematically illustrates electrical signal and power interconnections between various components of the monitoring device of the system embodiment of FIG. 1, and additional external components.

Reference is now made to FIG. 16 which schematically illustrates electrical signal and power interconnections between various components housed within monitoring device 200, as well as operative interconnections with external components. As shown, monitoring device 200 may include a power module 500 that includes rechargeable batteries 232 and that is selectively interconnectable to an external power source 702 for recharging of the batteries 232. For example, power module 500 may include a port (e.g. accessible on a back side of the monitoring device 200) to receive a plug-in power cord to interface the power module 500 with a 100 VAC to 240 VAC external power source 702, wherein the power module 500 may provide a DC signal (e.g. 9 VDC signal) for battery charging. Monitoring device 200 may further include a main power switch 510 selectively positionable in on/off positions by a user for controlling the delivery of a power signal from the batteries 232 of the power module 500 to other components of the monitoring device 200. As shown in FIG. 1, main power switch 510 may be located below user interface 250 of the monitoring device 200.

With further reference to FIG. 16, the power signal may be provided to a measurement module 520 which includes a measurement PCBA (printed circuit board assembly) 522 that provides the power signal to a main module 540 which includes a main PCBA 542. The measurement PCBA 522 includes one or more microprocessor(s) and associated memory components, and interfaces with a number of components discussed below. The main PCBA 542 includes one or more microprocessor(s) and associated memory components for processing signals from measurement module 520, user input signals from the user interface 250, and patient temperature signals from an external patient temperature sensor 704, and for providing control, power and output signals to the measurement module 520, the user interface 250, and a communications module 550 that includes a communications PCBA 552 comprising one or more microprocessor(s) and associated memory components. While the measurement module 520, main module 540 and communications module 550 are shown to have separate PCBA's, two or more of such modules may be consolidated so that the functionalities thereof are provided by a single PCBA.

Measurement module 520 may include the light sources 320a, 320b and the light detector array 330 for use in determining the level and/or volume of urine collected in the second urine collection device 200, as described above. The microprocessor(s) and associated memory component(s) of the measurement PCBA 522 may be configured to process the light detector array output signals to determine and store patient urine output information, including for example a total volume of urine collected from a given patient over an interval of time (e.g. a continuous time period during which the patient is catheterized) and/or a current urine flow rate. Further, the microprocessor(s) and associated memory component(s) of the measurement PCBA 522 may be configured to process the light detector array output signals to determine and store current urine volume data (e.g. indicative of a volume of urine present in the second urine collection device 100) and/or current urine level data for use in controlling the actuator 360 (e.g. a motor), and in turn, valve 172 of the second urine collection device 100 as otherwise described herein.

The stored patient urine output information and current urine volume data may be provided via output signals to the main PCBA 542. In turn, the main PCBA 542 may provide output signals comprising the patient urine output information to the user interface 250 for output at a display 500 (e.g. a touch panel display) and to the communications module 550 for receipt by the communications PCBA 552. The communications PCBA may then output the patient urine output information to an electronic medical records (EMR) system 706. In that regard, the communications PCBA 552 may be provided to output the patient urine output information via one or more networking modalities, such as serial output port (e.g. an RS-232 compliant port), or Ethernet port, or via Wi-Fi. For example, as shown in FIG. 1, a communications output port 554 may be provided on a side of the monitoring device 200 adjacent to the user interface 250.

The measurement module 520 may also include automated reader device, e.g. an RFID reader 420, for use in obtaining unique identification indicia from machine readable component, e.g. an RFID tag, located on second urine collection device 100 (e.g. located on a back surface of the cartridge 120), as described above. In turn, the unique identification indicia data may be processed and/or stored at the measurement PCBA 522 or main PCBA 542, and associated or included with the corresponding patient urine output information, wherein the unique identification indicia data may be provided as a part of or in association with the corresponding patient urine output and temperature information (e.g. without inclusion of patient identification information) to the user interface 250 and to communications module 550 for export to an electronic medical records system 706.

In the later regard, the electronic medical records system 706 may be provided to associate the unique identification indicia data, and corresponding patient urine output and temperature information with a specific patient. In turn, such information may be stored in the electronic medical records system 706 in associated relation to the patient and corresponding patient records. The electronic medical records system 706 may be further provided so that if a given second urine collection device 100 is disconnected from a given monitoring device 200 and subsequently reconnected to the same or a different monitoring device 200, the unique identification indicia data that is provided with the subsequent patient urine output and temperature information may be utilized to associate such data with a specific patient for storage in the electronic medical records system 706 in associated relation to the patient and corresponding patient records, together with previously stored patient urine output and temperature information, thereby facilitating the maintenance of a complete patient urine output and temperature record for time periods during which a given second urine collection device 100 is interconnected to a monitoring device 200 for patient urine output and temperature monitoring.

In some implementations, machine readable components, e.g. RFID tags, may be utilized that include not only unique identification indicia data, but additionally predetermined hash data generated from processing of the unique identification indicia data utilizing a predetermined hashing algorithm. In turn, both the unique identification indicia data and predetermined hash data may be obtained by the reader device f monitoring device 200, e.g. RFID sensor 420, and processed at measurement PCBA 522 or main PCBA. In particular, the predetermined hashing algorithm may be stored and utilized by a processor at the main PCBA 542 and/or at measurement PCBA 522 to process the unique identification indicia data according to the predetermined hashing algorithm to obtain a hash value which may then be compared to the predetermined hash value to establish a match and thereby authenticate the corresponding urine collection device for use. In the event of a match failure, such failure may indicate that a given urine collection device interconnected to monitoring device 200 is not authorized for use with the monitoring device 200. In turn, main PCBA 542 may be provided to preclude operation of various components of monitoring device 200, and to provide output signals to user interface 250 so as to provide an indication at the display 252 that the monitoring device 200 is unable to recognize and/or otherwise operatively interface with the urine collection device that is interconnected to the monitoring device 200.

The measurement module 520 may further include the actuator 360 (e.g. a servo motor) to control the valve member 172 of the second urine collection device 100 to accumulate and discharge successive volumes of urine collected at the second urine collection device 100, as discussed above. In that regard, the main PCBA 542 or measurement PCBA 522 may utilize the current urine volume or level data received from measurement module 520 to generate control signals that are provided to the actuator 360 to control the operation thereof. For example, the current urine volume or level data may include a present volume or level value indicative of a volume or level of urine present in the cartridge 120 of the second urine collection 100, and the microprocessor(s) of main PCBA 542 or measurement PCBA 522 may compare such present volume or level value to a stored, first predetermined accumulation amount, wherein if the present volume value is greater than or equal to the first predetermined accumulation amount, a processor of the main PCBA 542 or measurement PCBA 522 provides a first control signal to operate the actuator 360 to open valve 176 of the second urine collection device 100 to allow urine discharge from cartridge 120 (e.g. via gravity flow). In turn, a second control signal may be provided by main PCBA 542 or measurement PCBA 522 to actuator 360 to operate the motor 360 so as to close valve 176 (e.g. via the spring bias described above). For example, after valve opening, a second control signal may be provided after a predetermined time period that is determined to be sufficient to allow the collected urine volume to discharge (e.g. via gravity flow). In other approaches the light detector array output signals may be utilized or another sensor may be utilized to determine when the collected urine has been sufficiently discharged from cartridge 120 (e.g. to the predetermined minimum amount described above), whereupon the second control signal may be provided.

Measurement module 520 may also include a tilt sensor 430 (e.g. a multi-dimensional accelerometer) for detecting an orientation of monitoring device 200 and providing an output signal indicative thereof, as described above. The tilt sensor output signal may be employed by the measurement PCBA 522 to account for the detected tilt in processing of the light detector array output signals as described herein.

Further, the tilt sensor output signal may be utilized by main PCBA 542 to generate a user alert output signal and/or control signals. In that regard, a user output signal may be provided to user interface 250 to cause an audible and/or visual output signal to be provided.

Measurement module 520 may also include limit switch 420 to detect interconnection of second urine collection device 100 to monitoring device 200, as described above. In that regard, the measurement module 520 may be provided so that, upon detection of the interconnected presence of the second urine collection device 100, a corresponding signal may be provided by measurement PCBA 522 to main PCBA 542. In turn, the main PCBA 542 may provide control signals to initiate and control operations of various components of the monitoring device 200, including for example light source(s) 320a, 320b, the light detector array 330, the tilt sensor 430, the actuator 360 and/or the RFID sensor 420 of the measurement module 520, as well as the user interface 250 and/or communications module 550.

As noted above, the main module 540 may be interconnected with a patient temperature sensor 704, wherein the main PCBA 542 may receive temperature sensor output signals from the patient temperature sensor 604 that are indicative of the temperature of a patient. The main PCBA 542 may utilize the patient temperature sensor output signals to determine patient temperature information that may be stored and outputted by the module 540 as a part of the patient urine output information that is provided to the user interface 250 and to communications module 550 for export to an electronic medical records system 706.

As shown in FIG. 1, monitoring device 200 may include a temperature sensor input port 556 located on a side of the monitoring device 200 adjacent to the communications output port 554 and user interface 250. In some embodiments, the patient temperature sensor 704 may be provided to sense a temperature indicative of patient's core body temperature. In one approach, the patient temperature sensor 704 may be incorporated in to the urinary catheter 400 to sense the temperature of urine in a patient's bladder. In particular, urinary catheter 400 may be an in-dwelling catheter that includes a built in temperature-sensing thermistor having a pre-attached or attachable output cable. For example, the 400 Series™ Foley catheter products marketed by C. R. Bard, Inc. may be employed.

Figure 17:
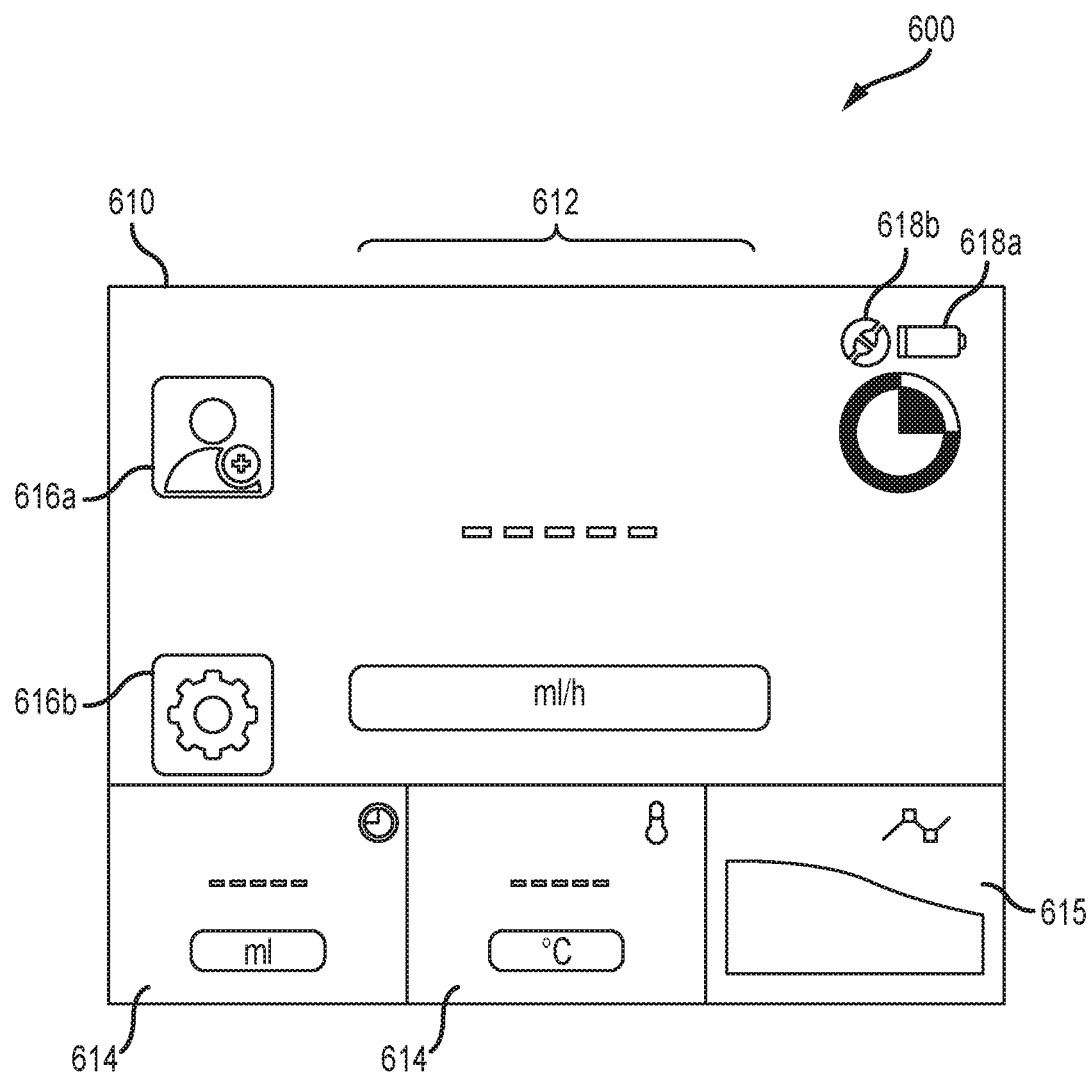
FIG. 17 illustrates a screen displayable at a touch panel display of the monitoring device of the embodiment of FIG. 1.

As noted above, user interface 250 may include a display 600 in the form of a touch panel display. For further description, reference is now made to FIG. 17, which illustrates a touch panel display 600 that provides a display region for displaying a plurality of screens that may be navigated via user touch panel input and facilitated by intuitive icons. In particular, FIG. 17 illustrates a primary screen 610 having a primary display region 612 and a plurality of secondary display regions 614. The primary screen 610 may be displayed upon start-up and during time periods that touch panel display 600 is in a primary display mode. The primary display region 612 and secondary display regions 614 may display a plurality of parameters corresponding with a plurality of types of clinical data that are monitored at the measurement module 520 and/or main module 540 and updated at the touch panel display 600 on an ongoing and periodic basis. Such parameters may include parameters represented by human-readable characters (e.g. alphanumeric characters) indicative of a magnitude of a monitored total volume of urine output collected over a time interval ("interval volume"), a monitored urine output flow rate ("flow rate"), and/or a monitored patient temperature ("temperature"). Each of these parameter measures may be included in or based upon the patient urine output information and patient temperature information generated/stored at the measurement module 520 and/or main module 540, and provided to the user interface 250 by the main module 540, as described above. In that regard, the main module 540 may be provided to execute preprogrammed instructions at one or more microprocessors to generate and store the noted parameters, as well as additional related data referenced hereinbelow, as patient urine output information and patient temperature information. Further, the user interface 250 and/or module 540 may be provided so that the displayed parameter measures are periodically updated while a given second urine collection device 100 is operatively interconnected to monitoring device 200 and to a given patient for urine output monitoring and urine collection by a corresponding first urine collection device 1, as described above.

The primary screen 610 may be provided to prominently display a selectable "primary" parameter in the primary display region 612, e.g. centered in a top portion of the touch panel display 600. "Secondary" parameters may be displayed in the secondary display regions 614, e.g. in a row across a bottom portion of the touch panel display 600. The primary parameter may be displayed in a primary, or first, display size, while the secondary parameters may be displayed in a secondary display, or second, size that is less than the primary display size. For example, the primary display size may be at least 150% of the secondary display size, and in some implementations, the primary display size may be at least 200% of the secondary display size.

The primary parameter displayed in the primary display region 612 may be provided to allow additional related data and settings to be accessed. In particular, touch panel input at the primary display region 612 will allow the additional data and settings related to the primary parameter to be accessed and established via additional screens, as will be further discussed below.

To enable a given secondary parameter to become the primary parameter displayed in the primary display region 612, a user may touch the corresponding secondary display region 614 that displays the given secondary parameter. In turn, such secondary parameter will become the primary parameter displayed in the primary display region 612 and the previous primary parameter will be displayed as a secondary parameter in one of the secondary display regions 614.

With specific reference to the primary screen 610 illustrated in FIG. 17, the primary display region 612 is shown as displaying a flow rate in a unit volume per unit time measure (e.g. ml/h). Further, two secondary display regions 614 are shown as displaying an interval volume in a volume unit measure (e.g. ml), and a temperature in a degrees unit measure (e.g. ° C.). As further illustrated, for each of the three parameters displayed in the primary display region 612 and secondary display regions 614, (i.e. a flow rate, an interval volume and a temperature), such regions each display a different icon that corresponds with the given displayed parameter and that is utilized in conjunction with the given parameter on the various screens described herein. Additionally, adjacent to the secondary display regions 614, the primary screen 610 may include a "graphics" icon button 615 for touch screen selection to access additional screens displaying one or more of the noted parameters graphically as a function of time (e.g. urine output flow rate and/or measured patient temperature as a function of time), as further described below.

As shown in FIG. 17, a plurality of function icon buttons 616a and 616b corresponding with a plurality of different functions may be displayed on primary screen 610, e.g. in a column on a left side of the primary display region 612. Such function icon buttons 616a and 616b may correspond with different data input and/or output functions, wherein upon touch panel selection of a given one of the function icon buttons 616a or 616b a corresponding data input and/or output function is enabled so that the display 600 exits the primary display mode and a corresponding function-related data input and/or output screen may be displayed on touch panel display 600.

In the primary screen 610 of FIG. 17, function icon button 616a may be an "add patient" icon button selectable to access a screen to initiate a urine output monitoring procedure for a given patient, as further described below. Additionally, function icon button 616b may be a "settings" icon button selectable to access one or more screens to review and establish one or more system settings, including for example a current date and time setting screen, a data communications state setting screen (i.e. to turn on/off data communications from communications module 550 to an electronic medical records system 706), and a settings reset screen (i.e. to reset all settings of user interface 250 to factory default values).

As further shown in FIG. 17, a plurality of status indicator icons 618a and 618b may be displayed on primary screen 610, e.g. displayed to the upper right of primary display region 612. For example, status indicator icon 618a may be a "battery charge" icon to pictorially indicate a remaining charge level of batteries 232, and status indicator 618b may be a "connectivity" icon to pictorially indicate the state of connectivity between monitoring device 200 and an electronic medical records system 706 (e.g. on or off).

Figure 18:
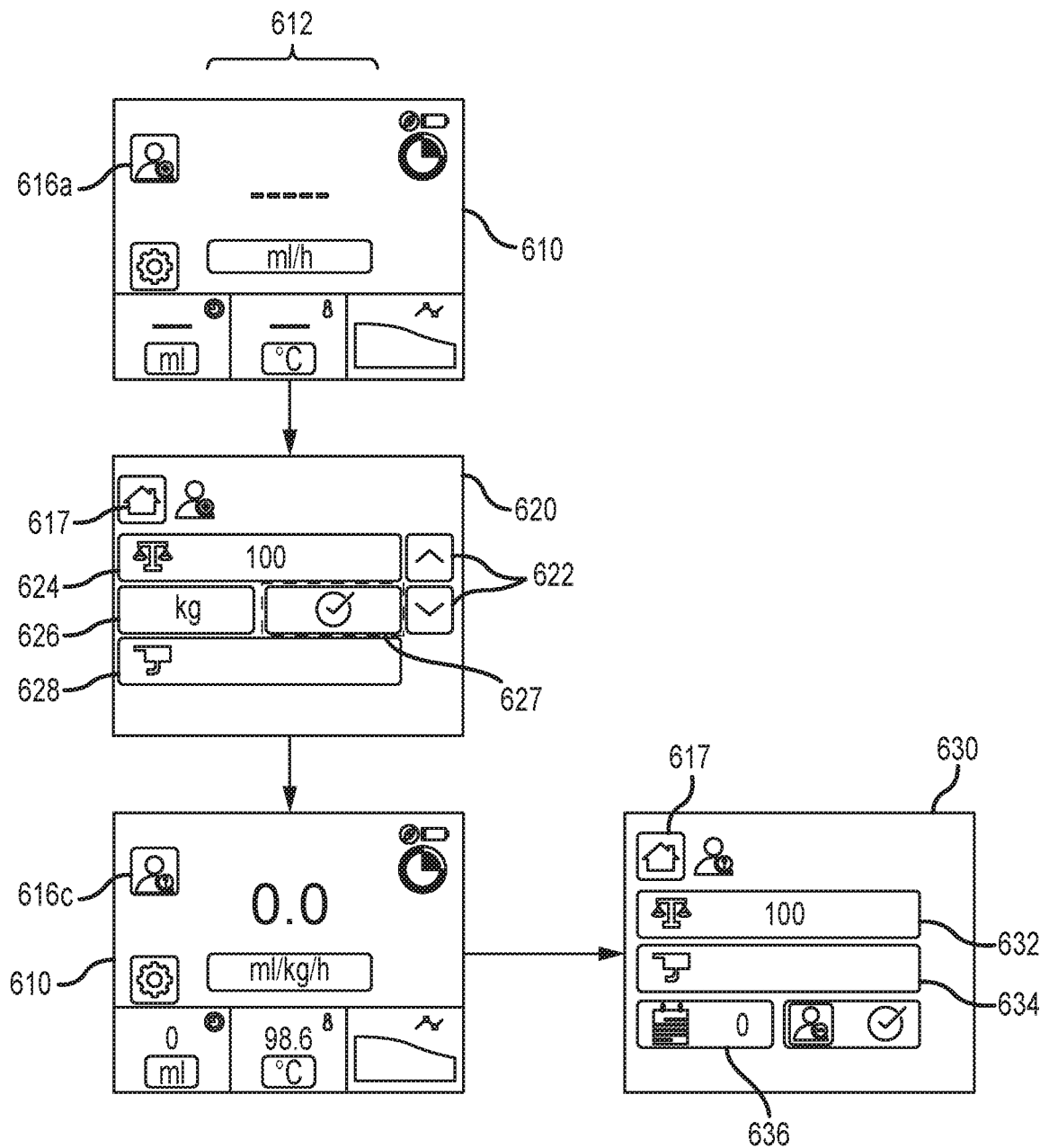
FIG. 18 illustrates another screen displayable at a touch panel display of the monitoring device of the embodiment of FIG. 1.

FIG. 18 is now referenced in relation to the use of touch panel display 600 to initiate a urine output monitoring procedure for a given patient. As shown, the "add patient" function icon button 616a displayed in primary screen 610 may be selected via touch panel input, wherein the touch panel display 600 may exit the primary display mode and patient weight entry screen 620 may be presented by touch panel display 600. Screen 620 may be utilized to enter a patient weight via touch panel upward and downward adjustment toggle buttons 622, wherein the patient weight may be displayed in a weight display region 624 together with a corresponding icon. Touch panel weight unit button 626 may be utilized to establish and display the desired weight unit measure for entry of the patient weight (e.g. kg or lb.). To accept an entered weight value, touch panel check button 627 may be utilized. Upon entry of a given patient's weight, the total volume of urine output collected over a time interval parameter, and the urine output flow rate parameter, will each be provided on a calculated, unit weight normalized basis, as further described below. Optionally, to disable such weight normalized calculations, the touch panel toggle button 622 for downward adjustment may be repeatedly pressed until a non-numerical indication is displayed in weight display region 624, e.g. a hyphen or series of hyphens, wherein the noted interval volume and flow rate parameters, as well as any related or derivative data provided at touch panel 600, will be presented without weight normalization.

With further reference to patient weight entry screen 620, the unique identification indicia corresponding with a specific second urine collection 100 utilized for the given urine output monitoring procedure may be displayed in ID display region 628 together with a corresponding icon. As described above, the unique identification indicia may be established by obtainment of data from an RFID tag located on second urine collection device 100 and provided to the user interface 250 by the main module 640 as part of or in association with the patient urine output information.

To initiate a given urine output monitoring procedure, a "home" icon button 617 on patient weight entry screen 620 may be selected by touch panel input. Upon such selection, primary screen 610 will again be displayed, with primary and secondary display regions 612, 614 populated with unit measure indicators for the displayed parameters. As shown in primary display region 612, if a patient weight has been entered via screen 620, the flow rate may be reported in a unit volume per unit patient weight per unit time measure (e.g. ml/kg/hr.), and as shown in one of the secondary display regions 614, the interval volume may be reported in a unit volume per unit weight measure (e.g. ml/kg).

As further shown in FIG. 18, after initiation of a case, primary screen 610 may display a case information function icon button 616c that may be selected via touch panel input to exit the primary display mode and thereby access a case information screen 630. Screen 630 may include a weight display region 632 that displays the entered patient weight and the corresponding icon, and an ID display region 634 that displays the unique identification indicia and the corresponding icon. Further, the case information screen 630 may include a cumulative time display region 636 and corresponding icon, wherein the display region 636 displays a value of the cumulative time that a given second urine collection device 100 has been interconnected to monitoring device 200. To return to the primary screen 610 the home icon button 617 may be utilized.

Figure 19:
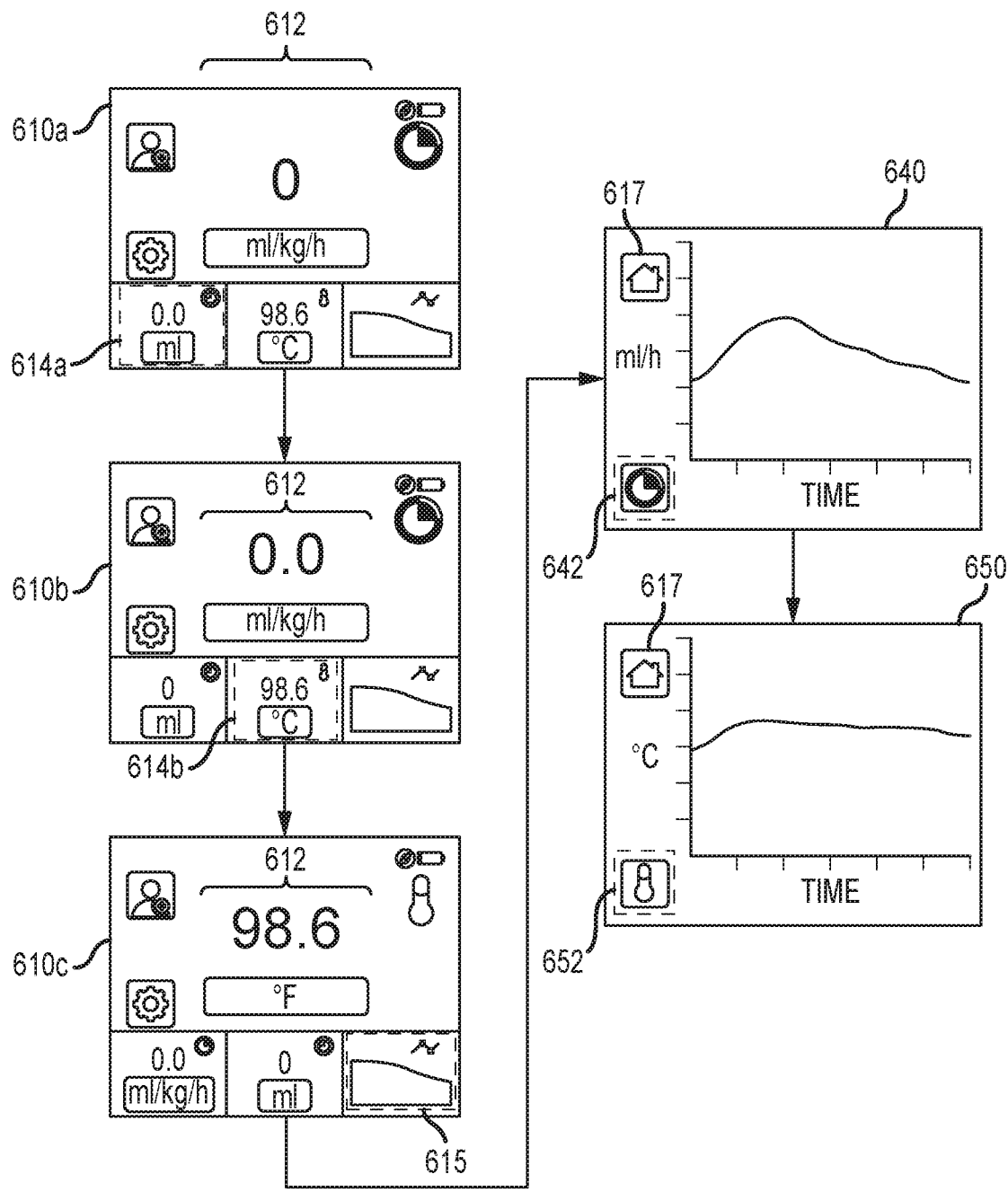
FIG. 19 illustrates another screen displayable at a touch panel display of the monitoring device of the embodiment of FIG. 1.

Reference is now made to FIG. 19 which illustrates primary screen 610 in three different display configurations, i.e. with different ones of the interval volume, flow rate and temperature parameters having been selected as the primary parameter for display in the primary display region 612. In the first display configuration 610a, the interval volume parameter is the primary parameter displayed in primary display region 612. As shown, by touch panel selection of the flow rate parameter displayed in secondary display region 614a of the first display configuration 610a, a second display configuration 610b may be provided in which the flow rate parameter is the primary parameter displayed in the primary display region 612. As further illustrated, by touch panel selection of the temperature parameter displayed in secondary display region 614b of the second display configuration 610b, a third display configuration 610c may be provided in which the temperature parameter is the primary parameter displayed in the primary display region 612.

As further shown, in FIG. 19, the graphics icon button 615 may be selected via touch panel input to access flow rate graph screen 640 and temperature graph screen 650. In particular, screen 640 may provide a graphical representation of urine output flow rate as a function of time, wherein the graphical representation may comprise a majority of screen 640. In turn, flow rate graph screen 640 may provide a patient temperature icon button 642 for touch screen selection to access temperature graph screen 650. Screen 650 may present a graphical representation of patient temperature as a function of time, wherein the graphical representation may comprise a majority of screen 650. In turn, temperature graph screen 650 may include a urine output flow rate button 652 for touch screen selection to return to screen 640. To return to the primary screen 610, flow rate graph screen 640 and temperature graph screen 650 may each include the home icon button 617 for touch screen selection by user.

Figure 20:
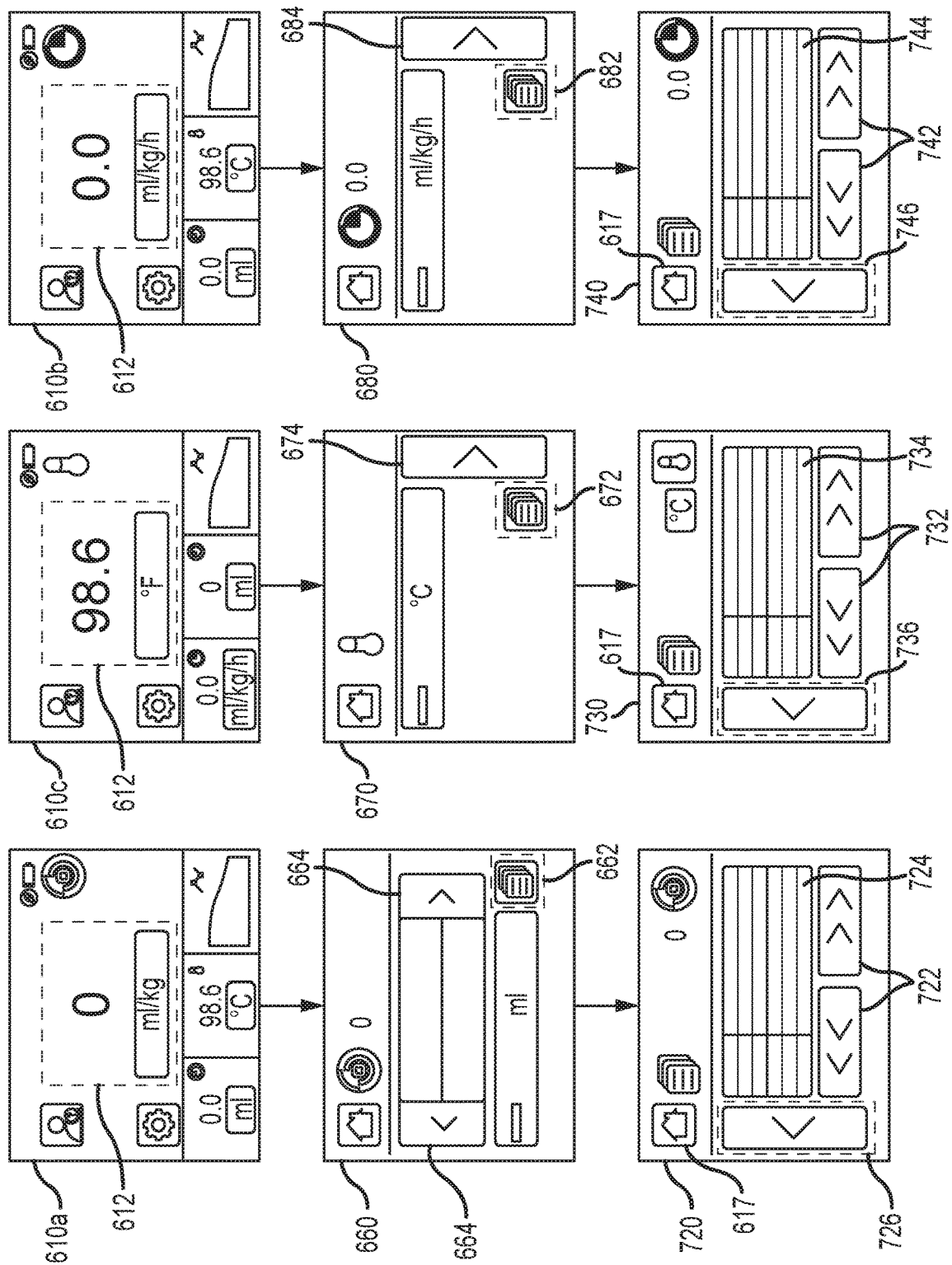
FIG. 20 illustrates another screen displayable at a touch panel display of the monitoring device of the embodiment of FIG. 1.

Reference is now made to FIG. 20, which illustrates the use of the three display configurations of primary screen 610 discussed above (i.e. in relation to FIG. 19) to access parameter-specific screens 660, 670 and 680, as well as parameter-specific, patient data history screens 720, 730 and 740. In particular, in each of the display configurations 610a, 610b and 610c, the touch panel primary display region 612 may be utilized (i.e. via touch panel input) to access parameter-specific screens 660, 670 and 680, corresponding with interval volume, temperature and flow rate parameters, respectively. In turn, for each of the interval volume, temperature and flow rate parameters, by touch panel selection of a data history icon button 662, 672 or 682, on parameter-specific screens 660, 670 or 680, respectively, a corresponding patient data history screen 720, 730 or 740 may be accessed which provides historical, time period-based data (e.g. hourly data) for the given parameter. As shown, each of the patient data history screens 720, 730 and 740 include scroll forward and backward buttons 722, 732 and 742 to display the desired hourly data for the given parameter in hourly measurement display regions 724, 734 and 744.

Additionally, each of the patient data history screens 720, 730 and 740 include the home icon button 617 that may be utilized to return to the corresponding of primary screen configuration 610a, 610b and 610c, respectively, for the corresponding active parameter. Further, the patient data history screens 720, 730 and 740 each include a "return" button 726, 736 and 746 that may be utilized to return to the prior corresponding parameter-specific screen, 660, 670 or 680, respectively.

In some embodiments, data history icon button 662, 672 and/or 682 may be provided for touch panel selection on primary screen 610, e.g. display configurations 610a, 610b, and/or 610c, respectively, to directly access patient data history screen 720, 730 and/or 740, respectively, providing historical, time period-based data (e.g. hourly data) for the given parameter and having additional functionality as discussed above. By way of example, data history icon button 662, 672 and 682, may be provided and displayed as a function icon button on primary screen 610, e.g. display configurations 610, 610b, and 610c, respectively, and may provide the corresponding data output function of providing direct access to patient data history screen 720, 730, and 740, respectively, which provide patient data historical, time period-based data (e.g. hourly data) for the given parameter.

As shown in FIG. 20, the parameter-specific screen 660, 670 and 680 may each include one or more toggle buttons 664, 674 and 684, respectively, that may be utilized to access additional data input and/or output screens corresponding with the given parameter. By way of example, toggle button 674 on the temperature parameter-specific screen 680 may be utilized to access one or more screens employable to establish one or more temperature alarm settings, e.g. an upper temperature threshold and a lower temperature threshold wherein if the monitored patient temperature is above the upper temperature threshold or below the lower temperature threshold a temperature alarm icon may be displayed on the touch panel display 600 and/or an audible alarm may be provided by the user interface 250. Similarly, toggle button 684 on the flow rate parameter-specific screen 680 may be utilized to access one or more screens employable to establish one or more urine output alarm settings, e.g. one or more upper and/or lower urine output per time period threshold settings, wherein if the monitored urine output is above an upper threshold or below a lower threshold a urine output alarm icon may be displayed on the touch panel display 600 and/or an audible alarm may be provided by the user interface 250.

Figure 21:
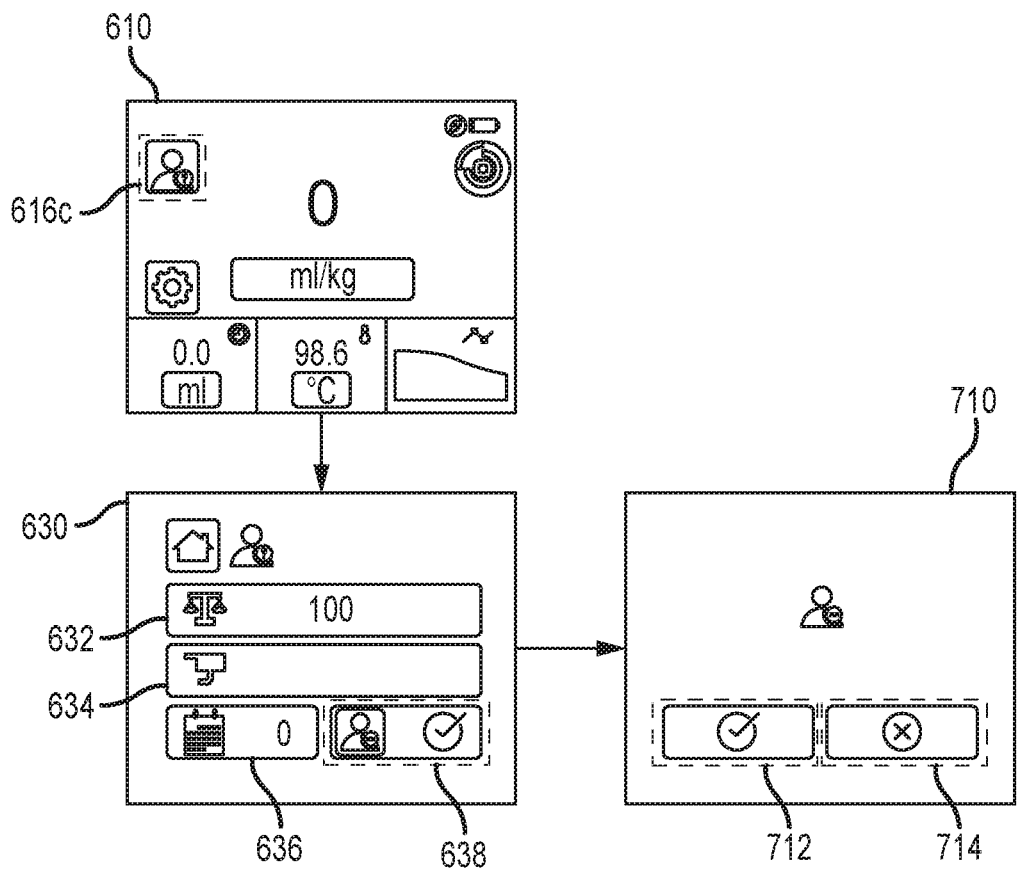
FIG. 21 illustrates another screen displayable at a touch panel display of the monitoring device of the embodiment of FIG. 1.

Reference is now made to FIG. 21, which illustrates the use of primary screen 610 to end a given patient urine output monitoring procedure. In particular, case information function icon button 616c may be selected by touch panel input to access case information screen 630, as described above. In turn, and "end case" check button 638 may be utilized by a user to indicate that the given patient urine collection procedure is to be terminated. In turn, upon touch panel input utilizing end case check button 638, an end case screen 710 may be displayed. As shown, the end case screen 710 may provide a confirm end case button 712 and a cancel end case button 714. The confirm end case button 712 may be utilized to confirm the termination of the given procedure, while the cancel end case button 714 may be utilized to cancel the termination process and thereby continue with patent urine output monitoring.

As may be appreciated, the various functionalities of the touch panel display 600 of user interface 250 described above may be provided via operative interface with the main module 540, wherein the patient urine output information and patient temperature information are determined by the measurement module 520 and/or main module 540, and provided by the main module 540 to the touch panel display 600 on an ongoing, periodic basis and/or in response to user input instructions at the touch panel display 600.

In additional embodiments, features of the first urine collection device 10 and second urine collection device 100 may be consolidated for use with a modified monitoring device 200. For example, in the embodiment shown in FIGS. 30 and 31, a urine output collection monitoring system 1000 may include a disposable urine collection apparatus 1010 and a monitoring device 2000 to which the disposable urine collection apparatus 1010 may be selectively, physically interconnected and disconnected.

The disposable urine collection apparatus 1010 may include a cartridge 1120 fixedly and fluidly interconnected to a collection reservoir 1020. The collection reservoir 1020 may have an internal volume sized to facilitate the accumulation of urine from a catheterized patient over an extended period of time. In that regard, the disposable urine collection apparatus may include a tubular inlet member 1170 having an inlet port 1172 at a first end for selective interconnection to and disconnection from a urinary catheter 400, and having a second end fluidly interconnected to internal volume 1124 of the cartridge 1120, e.g. via input port 1150. In that regard, cartridge 1120 may function as an anti-reflux chamber. As will be further described, when urine collection apparatus 1010 is fluidly interconnected to a catheterized patient (e.g. via urinary catheter 400), urine may flow through the inlet member 1170 in to cartridge 1120, and then flow from cartridge 1120 in to the collection reservoir 1020 for subsequent disposal.

The collection reservoir 1020 may have an internal volume that may accumulate a urine volume of at least about 1000 ml, and in contemplated embodiments, at least about 2000 ml. Additionally, the collection reservoir 1020 may of a flexible construction, e.g. to facilitate packaging and storage prior to use. Further, the collection reservoir 1020 may be at least partially light transmissive to facilitate visual observation of the quantity of urine accumulated therein. Optionally, volumetric gradation markings may be provided on a front side 1020a of the collection reservoir 1020 to facilitate manual logging of patient urine output. The collection reservoir 1020 may include an aperture 1084 at a top end to facilitate hanging the collection reservoir 1084 on a stand or monitoring device 1200 utilizing features as described above.

The cartridge 1120 may be of a rigid or semi-rigid construction and may be fixedly attached to a back surface 1020b of the collection reservoir 1020 via a peripheral flanged portion 1121. The cartridge 1120 may be at least partially light transmissive to facilitate visual observation of the quantity of urine accumulated therein. Optionally, volumetric gradation markings may be provided on an outward face of the cartridge 1120 to facilitate manual logging of patient urine output.

The disposable urine collection apparatus 1010 may be provided so that successive amounts of patient urine may be collected in cartridge 1120 and discharged from cartridge 1120 to collection reservoir 1020 in either a manual or automated manner. In that regard, the disposable urine collection apparatus 1010 may further include a valve member 1172 positionable to open and close a fluid passageway between the internal volume 1124 of cartridge 1120 and collection reservoir 1020. In the illustrated embodiment, the valve member 1172 may be disposed within a valve housing 1173 and may include an aperture 1172a extending therethrough, wherein when the valve member 1172 is rotatably positioned in an open position the aperture 1172a is located to permit urine flow from the internal volume 1124 of cartridge 1120 therethrough and in to the collection reservoir 1020 via a discharge port 1152 (as shown in FIG. 31). In turn, when the valve member 1172 is rotatably positioned in a closed position the aperture 1172a the valve member 1172 blocks the flow of urine from the internal volume 1124 in to the discharge port 1152 and collection reservoir 1020.

In a first mode of operation, the disposable urine collection apparatus 1010 may be employed in a stand-alone manner, free from interconnection to monitoring device 2000, wherein a user may manually rotate and thereby position the valve member 1172 in the open position for continuous urine flow through the cartridge 1120 in to the collection reservoir 1020. Alternatively, a user may manually, successively rotate and thereby position the valve in the closed position and the open position for the collection and discharge of successive amounts of urine, respectively, thereby allowing for manual logging of total urine flow amounts from which urine flow rate amounts may be manually determined.

In a second mode of operation, the disposable urine collection apparatus 1010 may be interconnected to the monitoring device 1200 for automated control of the valve member 1172 between the closed position and the open position. Further, the monitoring device 1200 may provide an output indicative of a total volume of patient urine collected in cartridge 1120 and discharged from cartridge 1120 to collection reservoir 1020 over a given interval of time, as well as an output indicative of a patient urine output flow rate, as otherwise described hereinabove in relation monitoring device 200. For such purposes, monitoring device 1200 may include a recess 1212 for receiving at least a portion of the cartridge 1120 therein. Further, monitoring device 1200 may include first and second light sources 1310a, 1310b located on one side of the recess 1212 for emitting light signals through the cartridge 1120 for detection on an opposing side of the recess 1212 by a light detector operable as described hereinabove in relation to monitoring device 200.

Additionally, monitoring device 1200 may include an actuator 1360 for providing a first mechanical output and second mechanical output to control positioning of the valve member 1172 between the open position and the closed position in an automated manner. By way of example, the actuator 1360 may provide a first mechanical output to rotate valve member 1172 from the open position to the closed position (e.g. clockwise rotation), and a second mechanical output to rotate the valve member 1172 from the closed position to the open position (e.g. counter clockwise rotation).

As further shown in FIG. 31, the disposable urine collection apparatus 1010 may further include an overflow port 1180 between the internal volume 1124 of cartridge 1120 and the collection reservoir 1020. In that regard, urine collected within the internal volume 1124 may flow in to the collection reservoir 1020 through the overflow port 1180 when the accumulated urine reaches a predetermined volume.

The foregoing description of is not intended to limit the invention to the form disclosed herein. Consequently, variations and modifications commensurate with the above teachings, and skill and knowledge of the relevant art, are within the scope of the present invention. The embodiments described hereinabove are further intended to explain known modes of practicing the invention and to enable others skilled in the art to utilize the invention in such or other embodiments and with various modifications required by the particular application(s) or use(s) of the present invention. It is intended that the appended claims be construed to include alternative embodiments to the extent permitted by the prior art.

What is claimed is:

1. A disposable urine collection apparatus, comprising:
   a first urine collection device, comprising:
      a collection reservoir having an internal volume;
      a diverter having an inlet port and a first flow control member for fluidly interconnecting the inlet port to a first passageway of the diverter in a first position of the first flow control member, and for fluidly interconnecting the inlet port to a second passageway of the diverter in a second position of the first flow control member; and
      a reservoir interface fixedly and fluidly interconnected to the collection reservoir, and fluidly interconnectable to the first passageway of the diverter, wherein when the first flow control member is in the first position the inlet port of the diverter is fluidly interconnected to the collection reservoir via the first passageway of the diverter and the reservoir interface, and wherein the reservoir interface includes a second flow control member for closing a passageway of the reservoir interface in a first position of the second flow control member; and
   a second urine collection device in fluid communication with the first urine collection device, the second urine collection device comprising:
      a cartridge having an internal chamber;
      a tubular inlet member having an inlet port at a first end and a second end fluidly interconnected to the internal chamber of the cartridge, wherein the inlet port of the tubular inlet member is selectively interconnectable to an outlet port of the second passageway of the diverter; and
      a projecting portion designed for removable connection to a light detection monitoring device, the projecting portion comprising an internal volume in fluid connection with the internal chamber of the cartridge.

2. A disposable urine collection apparatus as recited in claim 1, further comprising: at least one tubular outlet member having an outlet port at a first end and a second end fluidly interconnected to the internal chamber of the cartridge, wherein the outlet port of the at least one tubular outlet member is selectively interconnectable to an inlet port of the passageway of the reservoir interface.

3. A disposable urine collection apparatus as recited in claim 2, wherein the inlet port and the second passageway of the diverter are blocked from being fluidly interconnected by the first control member in the first position, and wherein the inlet port and the first passageway of the diverter are blocked from being fluidly interconnected by the first control member in the second position.

4. A disposable urine collection apparatus as recited in claim 2, wherein the diverter and the tubular inlet port of the inlet member are configured so that, upon interconnection of the inlet port of the tubular inlet member and the outlet port of the second passageway of the diverter, the first flow control member is mechanically moved from the first position of the first flow control member to the second position of the first flow control member.

5. A disposable urine collection apparatus as recited in claim 2, wherein the reservoir interface and the outlet port of the at least one tubular outlet member are configured so that, upon interconnection the outlet port of the at least one tubular outlet member and the inlet port of the passageway of the reservoir interface, the second flow control member is mechanically moved from the first position of the second flow control member to a second position of the second flow control member in which the passageway of the reservoir interface is fluidly interconnected to the collection reservoir.

6. A disposable urine collection apparatus as recited in claim 2, wherein the inlet port of the tubular inlet member and the outlet port of the second passageway of the diverter are not disconnectable after interconnection, and wherein the outlet port of the at least one tubular outlet member and the inlet port of the passageway of the reservoir interface are not disconnectable after interconnection.

7. A disposable urine collection apparatus as recited in claim 6, further comprising:
   a first interconnection member provided at the inlet port of the tubular inlet member and configured for locking engagement with the outlet port of the second passageway of the diverter; and
   a second interconnection member provided at the outlet port of the at least one tubular outlet member and configured for locking engagement with the inlet port of the passageway of the reservoir interface.

8. A disposable urine collection apparatus as recited in claim 2, wherein the outlet port of the second passageway of the diverter and the inlet port of the tubular inlet member have first complimentary configurations for mating engagement, wherein the outlet port of the at least one tubular outlet member and the inlet port of the passageway of the reservoir interface have second complementary configurations for mating engagement, and wherein the first and second complimentary configurations are different to physically preclude mating engagement of the outlet port of the second passageway of the diverter with the outlet port of the at least one tubular outlet member, and to preclude mating engagement of the inlet port of the tubular inlet member with the inlet port of the passageway of the reservoir interface.

9. A disposable urine collection apparatus as recited in claim 2, further comprising:
   a second tubular outlet member having a first end fluidly interconnected to the outlet port at the first end of the at least one tubular outlet member, and a second end fluidly interconnected to the internal chamber of the cartridge.

10. A disposable urine collection apparatus as recited in claim 2, wherein the cartridge is of a rigid construction.

11. A disposable urine collection apparatus as recited in claim 2, further comprising:
    a urinary catheter interconnected or interconnectable at a proximal end to the inlet port of the diverter to define a first closed fluid pathway from a distal end of the urinary catheter through the diverter and in to the internal volume of the collection reservoir when the first flow control member is in the first position, and to define a second closed fluid pathway from the distal end of the urinary catheter, through the diverter and the cartridge, and in to the internal volume of the collection reservoir when the first flow control member is in the second position.

12. A disposable urine collection apparatus as recited in claim 1, wherein the first flow control member comprises:
    a first channel configured to fluidly interconnect the inlet port of the diverter and the first passageway of the diverter when the first flow control member is in the first position; and, a second channel configured to fluidly interconnect the inlet port of the diverter and the second passageway of the diverter when the first flow control member is in the second position.

13. A disposable urine collection apparatus as recited in claim 1, wherein the second flow control member comprises:
   a channel configured to fluidly interconnect the inlet port of the passageway of the reservoir interface with the collection reservoir when the second flow control member is in a second position of the second flow control member.

14. A disposable urine collection apparatus as recited in claim 1, further comprising: a urinary catheter interconnected or interconnectable at a proximal end to the inlet port of the diverter.

15. A disposable urine collection apparatus as recited in claim 1, further comprising: a hanger member interconnected or interconnectable to the collection reservoir near a top end of the collection reservoir, wherein the diverter is interconnected or interconnectable to the hanger member.

16. A disposable urine collection apparatus as recited in claim 15, wherein the collection reservoir comprises a flexible bag.

17. A disposable urine collection apparatus as recited in claim 16, wherein the diverter and the reservoir interface are separately defined by a substantially rigid first housing and a substantially rigid second housing, respectively, and further comprising:
   a tubular intermediate member fluidly and fixedly interconnected at a first end to an interconnection port of the first passageway of the diverter, and fluidly and fixedly interconnected at a second end to an interconnection port of the reservoir interface.

18. A disposable urine collection apparatus as recited in claim 17, further comprising:
   a removable first cap member for capping the outlet port of the second passageway of the diverter; and,
   a removable second cap member for capping the inlet port of the passageway of the reservoir interface.

19. A disposable urine collection apparatus, comprising:
a first urine collection device, comprising:
   a collection reservoir having an internal volume;
   a diverter having an inlet port and a first flow control member for fluidly interconnecting the inlet port to a first passageway of the diverter in a first position, and for fluidly interconnecting the inlet port to a second passageway of the diverter in a second position;
   a reservoir interface fixedly and fluidly interconnected to the collection reservoir, and fluidly interconnectable to the first passageway of the diverter, wherein when the first flow control member is in the first position the inlet port of the diverter is fluidly interconnected to the collection reservoir via the first passageway of the diverter and the reservoir interface, and wherein the reservoir interface includes a second flow control member for closing a passageway of the reservoir interface in a first position of the second flow control member; and
a second urine collection device in fluid communication with the first urine collection device, the second urine collection device, comprising:
   a cartridge having an internal chamber;
   a tubular inlet member having an inlet port at a first end and a second end fluidly interconnected to the internal chamber of the cartridge, wherein the inlet port of the tubular inlet member is selectively interconnectable to an outlet port of the second passageway of the diverter;
   at least one tubular outlet member having an outlet port at a first end and a second end fluidly interconnected to the internal chamber of the cartridge, wherein the outlet port of the at least one tubular outlet member is selectively interconnectable to an inlet port of the passageway of the reservoir interface; and
   a projecting portion designed for removable connection to a monitoring device by insertion of the projecting portion into a corresponding recess in the monitoring device, the monitoring device adapted to determine a volume of urine collected in the cartridge by monitoring a surface position of the urine in the projecting portion.

* * * * *